US008858942B2

(12) United States Patent
Cartlidge et al.

(10) Patent No.: US 8,858,942 B2
(45) Date of Patent: *Oct. 14, 2014

(54) ANTIBODIES DIRECTED TO ERBB2

(71) Applicant: MedImmune Limited, Cambridge (GB)

(72) Inventors: Susan Ann Cartlidge, Acton Trussell (GB); Jianying Dong, San Diego, CA (US); Mark Hickinson, Macclesfield (GB); Ian Foltz, British Columbia (CA); Jaspal Singh Kang, British Columbia (CA)

(73) Assignee: MedImmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/710,883

(22) Filed: Dec. 11, 2012

(65) Prior Publication Data

US 2013/0089544 A1 Apr. 11, 2013

Related U.S. Application Data

(63) Continuation of application No. 12/376,196, filed as application No. PCT/US2007/075078 on Aug. 2, 2007, now Pat. No. 8,350,011.

(60) Provisional application No. 60/835,514, filed on Aug. 4, 2006.

(51) Int. Cl.
| C07K 16/28 | (2006.01) |
| A61K 39/395 | (2006.01) |
| C07K 16/40 | (2006.01) |
| C07K 16/32 | (2006.01) |
| A61K 45/06 | (2006.01) |
| C07K 14/71 | (2006.01) |
| A61K 39/00 | (2006.01) |

(52) U.S. Cl.
CPC ............ *C07K 16/40* (2013.01); *C07K 2317/92* (2013.01); *C07K 2317/76* (2013.01); *A61K 39/39558* (2013.01); *C07K 16/32* (2013.01); *A61K 2039/505* (2013.01); *A61K 45/06* (2013.01); *C07K 2317/73* (2013.01); *C07K 2317/33* (2013.01); *C07K 2317/21* (2013.01)
USPC .................. 424/138.1; 424/133.1; 424/142.1; 424/143.1; 424/141.1; 424/155.1; 530/387.3; 530/388.15; 530/388.22; 530/388.8; 530/387.7

(58) Field of Classification Search
None
See application file for complete search history.

(56) References Cited

U.S. PATENT DOCUMENTS

| 6,653,084 B1 | 11/2003 | King et al. |
| 6,987,088 B2 | 1/2006 | Dennis |
| 7,135,174 B2 | 11/2006 | Corvalan et al. |
| 7,244,826 B1 | 7/2007 | Marks |
| 7,306,801 B2 | 12/2007 | Caligiuri et al. |
| 7,777,008 B2 * | 8/2010 | Ponath et al. |

FOREIGN PATENT DOCUMENTS

| EP | 1106183 A2 * | 6/2001 |
| WO | WO 89/06692 | 7/1989 |
| WO | WO 97/00271 | 1/1997 |
| WO | WO 99/55367 | 11/1999 |
| WO | WO 03/048731 | 2/2002 |
| WO | WO 03/006509 A2 | 1/2003 |

OTHER PUBLICATIONS

Lamminmaki et al., Crystal structure of a recombinant anti-estradiol Fab fragment in complex with 17Beta-estradiol, J. Biol. Chem. 276(39):36687-36694, 2001.*
Rudikoff et al., Single amino acid substitution altering antigen-binding specificity, Proc. Natl. Acad. Sci. USA, 79:1979-1983, Mar. 1982.*
Xu et al., Antibody -induced growth inhibtion is mediated through immunochemically and functionally distinct epitopes on the extracellular domain of the c-erbB-2 (HER-2/neu) gene product of p. 185, Int. J. Cancer, 53:401-408, 1993.*
Le et al., HER2 antibodies pertuzumab and trastuzumab differ in their effect on cell signaling and growth inhibtion in breast cancer cells, Proc. Amer. Assoc. Cancer Res., 47(1):902, abstract #3836, Apr. 2006.*
MacCallum et al,, Antibody-antigen interactions: Conact analysis and binding site topography, J. Mol. Biol 262:732, 1996.*
Agus, D B et al., 2003, "Clinical activity in a phase I trial of HER-2-targeted rhuMAb 2C4 (pertuzumab) in patients with advanced solid malignancies (AST)," Program/Preceedings—American Society of Clinical Oncology, vol. 22, p. 192, Abstract No. 771.
Database EMBL (Online), Jan. 8, 1998, "*Homo sapiens* mRNA for immunoglobulin kappa light chain" XP002465474 retrieved from EBI accession No. EMBL:Y14736, Database accession No. Y14736 100% homology with seq. ID 47 & Paterson Trevor et al: "Variation in IgG1 heavy chain allotype does not contribute to differences in biological activity of two human anti-Rhesus (D) monoclonal antibodies", Immunotechnology (Shannon) vol. 4, No. 1, Jun. 1998 pp. 37-47, ISSN: 1380-2933.

(Continued)

*Primary Examiner* — Claire Kaufman

(57) ABSTRACT

The present invention relates to antibodies including human antibodies and antigen-binding portions thereof that specifically bind to ErbB2, preferably human ErbB2. In another embodiment, the antibodies or antigen-binding portions thereof inhibit ErbB2. The invention also relates to antibodies that are chimeric, bispecific, derivatized, single chain antibodies or portions of fusion proteins. The invention also relates to isolated heavy and light chain immunoglobulins or portions thereof derived from human anti-ErbB2 antibodies and nucleic acid molecules encoding such immunoglobulins. The present invention also relates to methods of using the antibodies and compositions for diagnosis and treatment. The invention also provides gene therapy methods using nucleic acid molecules encoding the heavy and/or light immunoglobulin molecules that comprise the human anti-ErbB2 antibodies. The invention also relates to transgenic animals or plants comprising nucleic acid molecules of the present invention.

12 Claims, 9 Drawing Sheets

(56) References Cited

OTHER PUBLICATIONS

Database EMBL (Online), Jan. 8, 1998, "*Homo sapiens* mRNA for immunoglobulin kappa light chain" XP002465474 retrieved from EBI accession No. EMBL:Y14735, Database accession No. Y14735 100% homology with seq. ID 46 & Paterson Trevor et al: "Variation in IgG1 heavy chain allotype does not contribute to differences in biological activity of two human anti-Rhesus (D) monoclonal antibodies", Immunotechnology (Shannon) vol. 4, No. 1, Jun. 1998 pp. 37-47, ISSN: 1380-2933.

International Search Report for corresponding PCT/US2007/070578 dated Jan. 23, 2008.

Kudo, Toshio et al., 1993, "Production of a Human Monoclonal Antibody to a Synthetic Peptide by Active In Vivo Immunization Using a SCID Mouse Grafted with Human Lymphocytes," Journal of Experimental Medicine, 171:327-338.

Lamminnaki et al., Sep. 28, 2001, "Crystal structure of a recombinant anti-estradiol Fab fragment in complex with 17Beta-estradiol," J. Biol. Chem. 276(39):36687-36694.

MacCallum et al., 1996, "Antibody-antigen interactions: contact analysis and binding site topography", J. Mol. Biol. 262:732-745.

Ross, J. S. et al., 2004, "Targeted Therapies for Cancer 2004", American Society for Clinical Pathology, 122:598-609.

Rudikoff et al., Mar. 1992, "Single amino acid substitution altering antigen-binding specificity," Proc. Natl Acad Sci USA, 79:1979-1983.

Saga et al., Feb. 1, 1991, Scintigraphic detection of overexpressed c-erbB-2 protooncogene products by a class-switched murine anti-c-erbB2 protein monoclonal antibody, Cancer Res., 51:990-994.

Yang, X.D. et al, 2001, "Development of ABX-EGF, a fully human anti-EGF receptor monoclonal antibody, for cancer therapy," Crit. Rev. Oncol. Hematol. 38:17-23.

\* cited by examiner

A

B

ANTIBODIES DIRECTED TO ERBB2

CROSS REFERENCE TO RELATED APPLICATIONS

This application is a continuation of U.S. application Ser. No. 12/376,196 filed on Nov. 2, 2009, said application Ser. No. 12/376,196 is a National Stage Application of PCT/US2007/075078 filed on Aug. 2, 2007, said PCT/US2007/075078 claims priority under 35 U.S.C. §119(e) to U.S. Provisional Application No. 60/835,514 filed Aug. 4, 2006. Each of the above listed applications is incorporated by reference herein in its entirety for all purposes.

REFERENCE TO THE SEQUENCE LISTING

This application incorporates by reference a Sequence Listing submitted with this application as text file entitled ERBB2_Sequence_Listing created on Jun. 27, 2012 and having a size of 60.8 kilobytes.

FIELD OF THE INVENTION

The present invention concerns anti-ErbB2 antibodies particularly human antibodies, and methods for making and using anti-ErbB2 antibodies, for example to treat cancer.

BACKGROUND OF THE INVENTION

The ErbB family of receptor tyrosine kinases are important mediators of cell growth, differentiation and survival. The receptor family includes four distinct members including epidermal growth factor receptor (EGFR or ErbB1), HER2 (ErbB2 or p185neu), HER3 (ErbB3) and HER4 (ErbB4).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway (Baselga and Mendelsohn, Pharmac. Ther. 64:127-154 (1994)). Monoclonal antibodies directed against the EGFR or its ligands, TGF-α and EGF, have been evaluated as therapeutic agents in the treatment of such malignancies. See, e.g., Baselga and Mendelsohn, supra; Masui et al. Cancer Research 44:1002-1007 (1984); and Wu et al. J. Clin. Invest. 95:1897-1905 (1995).

The second member of the ErbB family, p185neu, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., Science, 235:177-182 (1987); Slamon et al., Science, 244:707-712 (1989); and U.S. Pat. No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., Science, 229:974 (1985); Yokota et al., Lancet: 1:765-767 (1986); Fukushige et al., Mol Cell Biol., 6:955-958 (1986); Guerin et al., Oncogene Res., 3:21-31 (1988); Cohen et al., Oncogene, 4:81-88 (1989); Yonemura et al., Cancer Res., 51:1034:1034 (1991); Borst et al., Gynecol. Oncol., 38:364 (1990); Weiner et al., Cancer Res., 50:421-425 (1990); Kern et al., Cancer Res., 50:5184 (1990); Park et al., Cancer Res., 49:6605 (1989); Zhau et al., Mol. Carcinog., 3:254-257 (1990); Aasland et al. Br. J. Cancer 57:358-363 (1988); Williams et al. Pathobiology 59:46-52 (1991); and McCann et al., Cancer, 65:88-92 (1990).

ErbB2 may be overexpressed in prostate cancer (Gu et al. Cancer Lett. 99:185-9 (1996); Ross et al. Hum. Pathol. 28:827-33 (1997); Ross et al. Cancer 79:2162-70 (1997); and Sadasivan et al. J. Urol. 150:126-31 (1993)).

Antibodies directed against the rat p185neu and human ErbB2 protein products have been described. Drebin and colleagues have raised antibodies against the rat neu gene product, p185neu. See, for example, Drebin et al., Cell 41:695-706 (1985); Myers et al., Meth. Enzym. 198:277-290 (1991); and WO94/22478. Drebin et al. Oncogene 2:273-277 (1988) report that mixtures of antibodies reactive with two distinct regions of p185neu result in synergistic anti-tumor effects on neu-transformed NIH-3T3 cells implanted into nude mice. See also U.S. Pat. No. 5,824,311 issued Oct. 20, 1998.

Hudziak et al., Mol. Cell. Biol. 9(3):1165-1172 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α. See also U.S. Pat. No. 5,677,171 issued Oct. 14, 1997. The anti-ErbB2 antibodies discussed in Hudziak et al. are further characterized in Fendly et al. Cancer Research 50:1550-1558 (1990); Kotts et al. In vitro 26(3):59A (1990); Sarup et al. Growth Regulation 1:72-82 (1991); Shepard et al. J. Clin. Immunol. 11(3):117-127 (1991); Kumar et al. Mol. Cell. Biol. 11(2):979-986 (1991); Lewis et al. Cancer Immunol. Immunother. 37:255-263 (1993); Pietras et al. Oncogene 9:1829-1838 (1994); Vitetta et al. Cancer Research 54:5301-5309 (1994); Sliwkowski et al. J. Biol. Chem. 269(20):14661-14665 (1994); Scott et al. J. Biol. Chem. 266:14300-5 (1991); D'souza et al. Proc. Natl. Acad. Sci. 91:7202-7206 (1994); Lewis et al. Cancer Research 56:1457-1465 (1996); and Schaefer et al. Oncogene 15:1385-1394 (1997).

A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anti-cancer therapy (Baselga et al., J. Clin. Oncol. 14:737-744 (1996)). HERCEPTIN® received marketing approval from the Food and Drug Administration Sep. 25, 1998 for the treatment of patients with metastatic breast cancer whose tumors overexpress the ErbB2 protein.

Other anti-ErbB2 antibodies with various properties have been described in Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovski et al. PNAS (USA) 88:8691-8695 (1991); Bacus et al. Cancer Research 52:2580-2589 (1992); Xu et al. Int. J. Cancer 53:401-408

(1993); WO94/00136; Kasprzyk et al. Cancer Research 52:2771-2776 (1992); Hancock et al. Cancer Res. 51:4575-4580 (1991); Shawver et al. Cancer Res. 54:1367-1373 (1994); Arteaga et al. Cancer Res. 54:3758-3765 (1994); Harwerth et al. J. Biol. Chem. 267:15160-15167 (1992); U.S. Pat. No. 5,783,186; and Klapper et al. Oncogene 14:2099-2109 (1997).

Homology screening has resulted in the identification of two other ErbB receptor family members; ErbB3 (U.S. Pat. Nos. 5,183,884 and 5,480,968 as well as Kraus et al. PNAS (USA) 86:9193-9197 (1989)) and ErbB4 (EP Pat Appln No 599,274; Plowman et al., Proc. Natl. Acad. Sci. USA, 90:1746-1750 (1993); and Plowman et al., Nature, 366:473-475 (1993)). Both of these receptors display increased expression on at least some breast cancer cell lines.

The ErbB receptors are generally found in various combinations in cells and heterodimerization is thought to increase the diversity of cellular responses to a variety of ErbB ligands (Earp et al. Breast Cancer Research and Treatment 35: 115-132 (1995)). EGFR is bound by at least six different ligands; epidermal growth factor (EGF), transforming growth factor alpha (TGF-$\alpha$), amphiregulin, heparin binding epidermal growth factor (HB-EGF), betacellulin and epiregulin (Groenen et al. Growth Factors 11:235-257 (1994)). A family of heregulin proteins resulting from alternative splicing of a single gene are ligands for ErbB3 and ErbB4. The heregulin family includes alpha, beta and gamma heregulins (Holmes et al., Science, 256:1205-1210 (1992); U.S. Pat. No. 5,641,869; and Schaefer et al. Oncogene 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. Growth Factors 11:235-257 (1994); Lemke, G. Molec. & Cell. Neurosci. 7:247-262 (1996) and Lee et al. Pharm. Rev. 47:51-85 (1995). Recently three additional ErbB ligands were identified; neuregulin-2 (NRG-2) which is reported to bind either ErbB3 or ErbB4 (Chang et al. Nature 387 509-512 (1997); and Carraway et al Nature 387:512-516 (1997)); neuregulin-3 which binds ErbB4 (Zhang et al. PNAS (USA) 94(18):9562-7 (1997)); and neuregulin-4 which binds ErbB4 (Harari et al. Oncogene 18:2681-89 (1999)) HB-EGF, betacellulin and epiregulin also bind to ErbB4. While EGF and TGF$\alpha$ do not bind ErbB2, EGF stimulates EGFR and ErbB2 to form a heterodimer, which activates EGFR and results in transphosphorylation of ErbB2 in the heterodimer. Dimerization and/or transphosphorylation appear to activate the ErbB2 tyrosine kinase. See Earp et al., supra. Likewise, when ErbB3 is co-expressed with ErbB2, an active signaling complex is formed and antibodies directed against ErbB2 are capable of disrupting this complex (Sliwkowski et al., J. Biol. Chem., 269(20):14661-14665 (1994)). Additionally, the affinity of ErbB3 for heregulin (HRG) is increased to a higher affinity state when co-expressed with ErbB2. See also, Levi et al., Journal of Neuroscience 15: 1329-1340 (1995); Morrissey et al., Proc. Natl. Acad. Sci. USA 92: 1431-1435 (1995); and Lewis et al., Cancer Res., 56:1457-1465 (1996) with respect to the ErbB2-ErbB3 protein complex. ErbB4, like ErbB3, forms an active signaling complex with ErbB2 (Carraway and Cantley, Cell 78:5-8 (1994)).

The product of the HER-2/neu proto-oncogene, HER2, is the second member of the human epidermal growth factor receptor (HER) family of tyrosine kinase receptors and has been suggested to be a ligand orphan receptor. Ligand-dependent heterodimerization between HER2 and another HER family member, HER1, HER3 or HER4, activates the HER2 signaling pathway. The intracellular signaling pathway of HER2 is thought to involve ras-MAPK and PI3K pathways, as well as MAPK-independent S6 kinase and phospholipase C-gamma signaling pathways (Graus-Porta et al., Mol Cell Biol. 1995 March; 15(3): 1182-1191; Grant et al., Front Biosci. 2002 Feb. 1; 7:d376-89).

HER2 signaling also effects proangiogenic factors, vascular endothelial growth factor (VEGF) and interleukin-8 (IL-8), and an antiangiogenic factor, thrombospondin-1 (TSP-1). Re-expression of HER2 in MCF-7 and T-47D breast cancer cells that endogenously express low levels of HER2 results in elevated expression of VEGF and IL-8 and decreased expression of TSP-1. Inhibition of HER2 with a humanized anti-HER2 antibody (trastuzumab, or Herceptin®) or a retrovirus-mediated small interfering RNA against HER2 (siHER2) decreases VEGF and IL-8 expression, but increased TSP-1 expression in BT474 breast cancer cells that express high levels of HER2. HER2 signaling therefore influences the equilibrium between pro- and antiangiogenic factors via distinct signaling pathways. Trastuzumab inhibits angiogenesis and tumor growth, at least in part, through activation of the HER2-p38-TSP-1 pathway and inhibition of the HER2—PI3K-AKT-VEGF/IL-8 pathway (Wen et al., Oncogene. 2006 May 22; Epub). Additionally, ErbB2 membrane RTK can confer resistance to taxol-induced apoptosis by directly phosphorylating Cdc2 (Tan et al., Mol. Cell. 2002 May; 9 (5):993-1004).

SUMMARY OF THE INVENTION

Certain embodiments of the invention are described below.

In one embodiment, the invention comprises a targeted binding agent, e.g. a human monoclonal antibody or an antigen-binding portion thereof, that specifically binds to ErbB2. The targeted binding agent can possess at least one of the following properties:
(a) binds to human cells;
(b) binds to cells expressing cynomolgus ErbB2;
(c) competes partially with Herceptin® but does not compete with 2C4;
(d) inhibits ErbB2 phosphorylation in MCF7 cells with a EC50 of less than 50 ng/ml;
(e) inhibits cell proliferation with an EC50 of less than 50 ng/ml in SKBR3 cells;
(f) binds to ErbB2 with a KD of 13.5 nM or less; or
(g) has an off rate (koff) for ErbB2 of 2.14×10-4 s-1 or smaller.

In another embodiment, the targeted binding agent binds ErbB2 with a KD of 13.5 nM or less and inhibits activation of ErbB. In another embodiment, said targeted binding agent is an antibody. In an embodiment, said antibody is a humanized, chimeric or human monoclonal antibody or antigen-binding portion thereof.

In another embodiment, the invention comprises a targeted binding agent, e.g. a humanized, chimeric or human monoclonal antibody or antigen-binding portion thereof, that binds specifically to and inhibits human ErbB2, wherein the targeted binding agent has at least one property selected from the group consisting of:
(a) competes for binding to ErbB2 with an antibody selected from the group consisting of: 1.44.1, 1.140, 1.43, 1.14.1, 1.100.1, 1.96, 1.18.1, 1.20, 1.39, 1.24 and 1.71.3 1.44.1, 1.140, 1.43, 1.14.1, 1.100.1, 1.96, 1.18.1, 1.20, 1.39, 1.24 and 1.71.3;
(b) competes for binding to ErbB2 with an antibody selected from the group consisting of: 1.44.1, 1.140, 1.43, 1.14.1, 1.100.1, 1.96, 1.18.1, 1.20, 1.39, 1.24 and 1.71.3 1.44.1, 1.140, 1.43, 1.14.1, 1.100.1, 1.96, 1.18.1, 1.20, 1.39, 1.24 and 1.71.3;

(c) binds to the same epitope of ErbB2 as an antibody selected from the group consisting of: 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3;

(d) binds to ErbB2 with substantially the same KD as an antibody selected from the group consisting of: 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3; and (e) binds to ErbB2 with substantially the same off rate as an antibody selected from the group consisting of: 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3.

In another embodiment, said binding targeted agent is an antibody. In another embodiment, said antibody is a humanized, chimeric or human monoclonal antibody or antigen-binding portion thereof.

In another embodiment, the invention comprises a targeted binding agent, e.g. a monoclonal antibody or an antigen-binding portion thereof, that specifically binds ErbB2, wherein:

(a) the targeted binding agent comprises the heavy chain CDR1, CDR2 and CDR3 amino acid sequences of an antibody selected from the group consisting of: 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3;

(b) the targeted binding agent comprises the light chain CDR1, CDR2 and CDR3 amino acid sequences of an antibody selected from the group consisting of 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3; and (c) the targeted binding agent comprises a heavy chain of (a) and a light chain of (b); or the targeted binding agent of (c) wherein the heavy chain and light chain CDR amino acid sequences are selected from the same antibody.

In another embodiment, said targeted binding agent is an antibody. In another embodiment, said antibody is a humanized, chimeric or human monoclonal antibody or antigen-binding portion thereof. In another embodiment, the monoclonal antibody or an antigen-binding portion thereof further includes the heavy chain amino acid sequence set forth in SEQ ID NO: 46, the light chain amino acid sequence set forth in SEQ ID NO: 47, or both.

In another embodiment, the monoclonal antibody or an antigen-binding portion thereof of the invention can be from any isotype.

In another embodiment, the human monoclonal antibody or antigen-binding portion thereof of the invention includes a heavy chain that utilizes a human VH 3-21 gene, a human VH 3-7 gene, a human VH 4-31 gene, or a human VH 3-13 gene.

In another embodiment, the human monoclonal antibody or antigen-binding portion thereof of the invention includes a heavy chain that utilizes a human VH 3-21 gene, a human VH 3-7 gene, a human VH 4-31 gene, or a human VH 3-13 gene.

In another embodiment, the human monoclonal antibody or antigen-binding portion thereof of the invention includes a light chain that utilizes a human VK B3 gene, a human VK L1 gene, a human VK A2 gene, or a human VK A1 gene.

In another embodiment, the human monoclonal antibody or antigen-binding portion thereof of the invention includes an antibody or portion further comprises a light chain that utilizes a human VK B3 gene, a human VK L1 gene, a human VK A2 gene, or a human VK A1 gene.

In another embodiment, the VL domain, the VH domain, or both of the human monoclonal antibody or antigen-binding portion thereof of the invention are at least 90% identical in amino acid sequence to the VL domain, VH domain or both, respectively, of monoclonal antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3

In another embodiment, the invention includes a monoclonal antibody or an antigen-binding portion thereof that specifically binds ErbB2, wherein the antibody comprises one or more of an FR1, FR2, FR3 or FR4 amino acid sequence of an antibody selected from the group consisting of: 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3.

In another embodiment, the invention includes a human monoclonal antibody or an antigen-binding portion, wherein the antibody includes (a) a heavy chain amino acid sequence that is at least 90% identical to the heavy chain amino acid sequence of monoclonal antibody 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3;

(b) a light chain amino acid sequence that is at least 90% identical to the light chain amino acid sequence of monoclonal antibody 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3; or both (a) and (b).

In another embodiment, the invention includes a human monoclonal antibody or an antigen-binding portion described herein, wherein said antigen-binding portion is selected from the group consisting of: Fab, Fab', F(ab')2, Fd, Fv, dAb, and complementarity determining region (CDR) fragments, single-chain antibodies (scFv or scFv2), chimeric antibodies, diabodies, dispecific antibodies, and polypeptides that contain at least a portion of an antibody that is sufficient to confer specific antigen binding to the polypeptide In yet another embodiment, the invention includes a composition comprising the targeted binding agent, e.g. an antibody or antigen-binding portion described herein, and a pharmaceutically acceptable carrier. The composition can further include an additional therapeutic or diagnostic agent. In one embodiment, the composition further includes a second antibody that specifically binds ErbB2 wherein said second antibody does not compete for binding to ErbB2 with an antibody selected from the group consisting of: 1.14.1, 1.18.1, 1.20.1, 1.24.3, 1.39.1, 1.71.3, 1.96.2, 1.100.1, and 1.140.1.

In yet another embodiment, the invention includes an isolated cell line that produces the targeted binding agent, antibody or antigen-binding portion described herein or the heavy chain or light chain of said antibody or said portion.

In yet another embodiment, the invention includes an isolated nucleic acid molecule comprising a nucleotide sequence that encodes the heavy chain or an antigen-binding portion thereof, the light chain or an antigen-binding portion thereof, or both. The isolated nucleic acid can include a nucleotide sequence selected from the group consisting of:

(a) the nucleotide sequence of SEQ ID NO:1;
(b) the nucleotide sequence encoding SEQ ID NO:2;
(c) the nucleotide sequence of SEQ ID NO:3;
(d) the nucleotide sequence encoding SEQ ID NO:4;
(e) the nucleotide sequence of SEQ ID NO:5;

(f) the nucleotide sequence encoding SEQ ID NO:6;
(g) the nucleotide sequence of SEQ ID NO:7;
(h) the nucleotide sequence encoding SEQ ID NO:8;
(i) the nucleotide sequence of SEQ ID NO:9;
(j) the nucleotide sequence encoding SEQ ID NO:10;
(k) the nucleotide sequence of SEQ ID NO:11;
(l) the nucleotide sequence encoding SEQ ID NO:12;
(m) the nucleotide sequence of SEQ ID NO:13;
(n) the nucleotide sequence encoding SEQ ID NO:14;
(o) the nucleotide sequence of SEQ ID NO:15;
(p) the nucleotide sequence encoding SEQ ID NO:16;
(q) the nucleotide sequence of SEQ ID NO:17;
(r) the nucleotide sequence encoding SEQ ID NO:18;
(s) the nucleotide sequence of SEQ ID NO:19;
(t) the nucleotide sequence encoding SEQ ID NO:20;
(u) the nucleotide sequence of SEQ ID NO:21;
(v) the nucleotide sequence encoding SEQ ID NO:22;
(w) the nucleotide sequence of SEQ ID NO:23;
(x) the nucleotide sequence encoding SEQ ID NO:24;
(y) the nucleotide sequence of SEQ ID NO:25;
(z) the nucleotide sequence of SEQ ID NO:26;
(aa) the nucleotide sequence of SEQ ID NO:27;
(bb) the nucleotide sequence encoding SEQ ID NO:28;
(cc) the nucleotide sequence of SEQ ID NO:29;
(dd) the nucleotide sequence encoding SEQ ID NO:30;
(ee) the nucleotide sequence of SEQ ID NO:31;
(ff) the nucleotide sequence encoding SEQ ID NO:32;
(gg) the nucleotide sequence of SEQ ID NO:33;
(hh) the nucleotide sequence encoding SEQ ID NO:34;
(ii) the nucleotide sequence of SEQ ID NO:35;
(jj) the nucleotide sequence encoding SEQ ID NO:36;
(kk) the nucleotide sequence of SEQ ID NO:37;
(ll) the nucleotide sequence encoding SEQ ID NO:38;
(mm) the nucleotide sequence of SEQ ID NO:39;
(nn) the nucleotide sequence encoding SEQ ID NO:40;
(oo) the nucleotide sequence of SEQ ID NO:41;
(pp) the nucleotide sequence encoding SEQ ID NO:42;
(qq) the nucleotide sequence of SEQ ID NO:43; and
(rr) the nucleotide sequence encoding SEQ ID NO:44.

The invention further comprises a vector comprising the nucleic acid molecule described herein, wherein the vector optionally comprises an expression control sequence operably linked to the nucleic acid molecule. In another embodiment, the invention includes a host cell comprising the vector or the nucleic acid molecule described herein.

In another embodiment, the invention includes a method for producing the targeted bindging agent, monoclonal antibody or antigen-binding portion described herein comprising the steps of culturing the host cell or the cell line described herein under suitable conditions and recovering said antibody or antigen-binding portion.

The invention further comprises a non-human transgenic animal or transgenic plant comprising the nucleic acid described herein, wherein the non-human transgenic animal or transgenic plant expresses said nucleic acid. The invention also includes a method for isolating an antibody or antigen-binding portion thereof that specifically binds to human ErbB2. The method includes the step of isolating the antibody from the non-human transgenic animal or transgenic plant.

In another embodiment, the invention includes a method for making a human monoclonal antibody that specifically binds to ErbB2, comprising the steps of:
(i) immunizing a non-human transgenic animal that is capable of producing human antibodies with ErbB2, an immunogenic portion of ErbB2 or a cell or tissue expressing ErbB2;
(ii) allowing the transgenic animal to mount an immune response to ErbB2; and
(iii) recovering the antibody.

In another embodiment, the invention includes a method for treating, preventing or alleviating the symptoms of an ErbB2-mediated disorder in a subject in need thereof, comprising the step of administering to said subject a targeted binding agent, an antibody or antigen-binding portion or the composition described herein, wherein said targeted binding agent, antibody or antigen-binding portion inhibit ErbB2.

In yet another aspect, the invention includes a method for treating, preventing or alleviating the symptoms of an ErbB2-mediated disorder such as cancer in a subject in need thereof with a targeted binding agent, e.g. an antibody or antigen-binding portion thereof, that specifically binds to ErbB2 comprising the steps of:
(i) administering an effective amount of an isolated nucleic acid molecule encoding the heavy chain or the antigen-binding portion thereof, an isolated nucleic acid molecule encoding the targeted bind agent, e.g. the light chain or the antigen-binding portion thereof, or both the nucleic acid molecules encoding the light chain and the heavy chain or antigen-binding portions thereof of an antibody; and,
(ii) expressing the nucleic acid molecule.

An ErbB2-mediated disorder can be selected from the group consisting of breast, bladder, lung, head, neck, prostate, stomach, endometrium, salivary gland, lung, kidney, colon, thyroid, pancreatic cancer, and glioblastomas In another embodiment, the invention includes a method of inhibiting proliferation of a cancer cell expressing ErbB2 in a subject in need thereof, the method comprising the step of administering to said subject a targeting binding agent, e.g. an antibody or antigen-binding portion or the composition described herein, wherein said targeted binding agent inhibits ErbB2. In another embodiment, said binding targeted agent is an antibody. In another embodiment, said antibody is a humanized, chimeric or human monoclonal antibody or antigen-binding portion thereof.

In another embodiment, the invention includes a method for inhibiting an ErbB2 activity in a cell, for example, of a subject or cancer cell, expressing ErbB2, comprising contacting the cell with a targeted binding agent or with the composition described herein, wherein the ErbB2 activity in the cell is selected from the group consisting of:
(a) phosphorylation of ErbB2;
(b) activation of the MAPK pathway;
(c) activation of the PI3K pathway;
(d) inhibition of CDC2; and
(e) combinations thereof.

In one embodiment, the phosphorylation of ErbB2 is inhibited by 48 hours. In another embodiment, said binding targeted agent is an antibody. In another embodiment, said antibody is a humanized, chimeric or human monoclonal antibody or antigen-binding portion thereof.

In another embodiment, the invention includes a method for modulating an ErbB2 activity in a cell expressing ErbB2, including contacting the cell with an antibody or antigen-binding portion or with the composition described herein wherein the ErbB2 activity in the cell is activation of the p38-TSP-1 pathway.

In one embodiment an antigen binding site may comprise a heavy chain CDR1, CDR2 and CDR3 and a light chain CDR1, CDR2 and CDR3 of any of antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3 with as many as twenty, sixteen, ten, nine or fewer, e.g. one, two, three, four or five, amino acid additions, substitutions, deletions, and/or insertions within the disclosed CDRs. Such modifications may potentially be made at any residue within the CDRs.

In another embodiment the targeted binding agent or antibody may comprise a sequence comprising any one, two, three, four, five or six of the CDR1, CDR2 or CDR3 sequences as shown in Table 4, 4(a) and/or Table 5. In another embodiment the targeted binding agent or antibody may comprise a sequence comprising a CDR1, CDR2 and CDR3 sequence as shown in Table 4, and/or 4(a). In another embodiment the targeted binding agent or antibody may comprise a sequence comprising a CDR1, CDR2 and CDR3 sequence as shown in Table 5. In another embodiment the targeted binding agent or antibody may comprise a sequence comprising a CDR1, CDR2 and CDR3 sequence as shown in Table 4 or 3(a) and a CDR1, CDR2 and CDR3 sequence as shown in Table 5. It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3, or as defined herein.

In another embodiment the targeted binding agent or antibody may comprise a sequence comprising any one, two, three, four, five or six of the CDR1, CDR2 and CDR3 sequences of any one of the fully human monoclonal antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3, as shown in Table 4, 4(a) or in Table 5. In one embodiment the targeted binding agent or antibody may comprise a sequence comprising a CDR1, CDR2 and CDR3 sequence of fully human monoclonal antibody 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3 as shown in Table 4 and 4(a). In another embodiment the targeted binding agent or antibody may comprise a sequence comprising a CDR1, CDR2 and CDR3 sequence of fully human monoclonal antibody 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3, as shown in Table 5. In another embodiment the targeted binding agent or antibody may comprise a sequence comprising a CDR1, CDR2 and CDR3 sequence of fully human monoclonal antibody 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3 as shown in Table 4 and 4(a), and a CDR1, CDR2 and CDR3 sequence of fully human monoclonal antibody 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3 as shown in Table 5.

DETAILED DESCRIPTION OF THE INVENTION

Definitions and General Techniques

Figure 1:
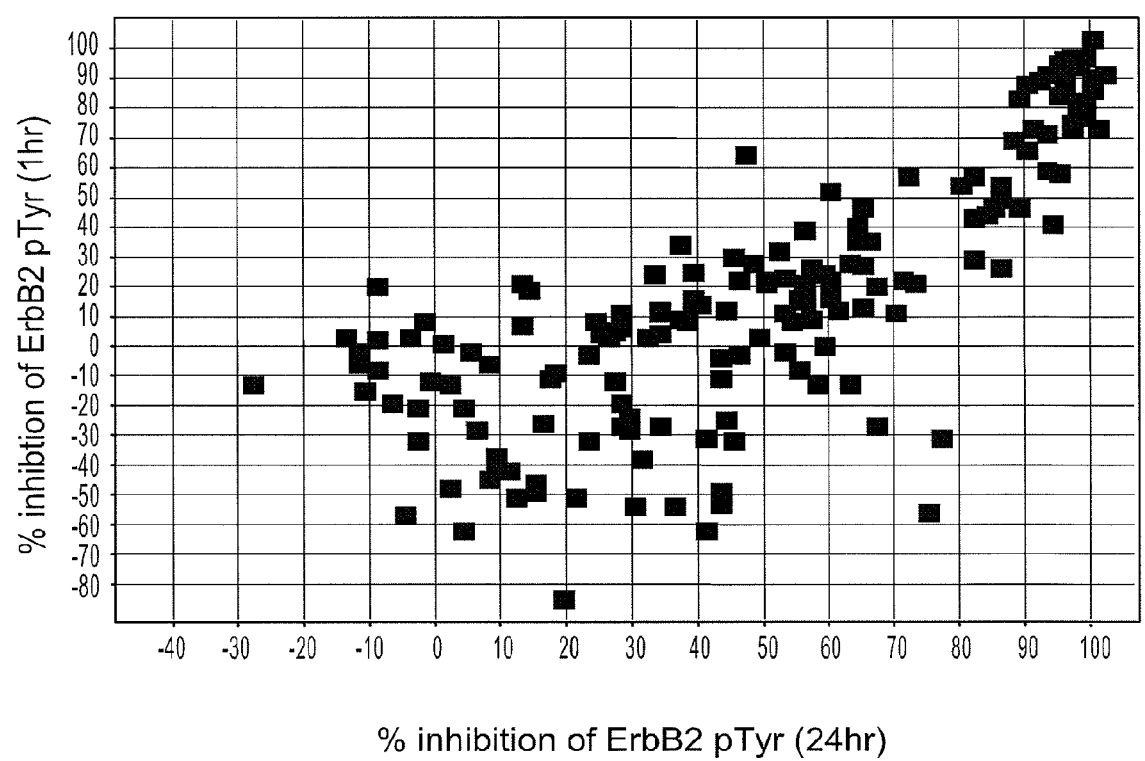
FIG. 1 is a graph depicting the correlation of the effects of 152 hybridoma supernatants on Heregulin-induced ErbB2 phosphorylation in MCF7 cells after 1 hr (Y axis) and 24 hr (X axis) pre-incubation.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of subjects.

Each antibody has been given an identification number that includes either two or three numbers separated by one or two decimal points. In some cases, several clones of one antibody were prepared. A number of clones have different identification numbers although they have the identical nucleic acid and amino acid sequences as the parent sequence, they may also be listed separately. Thus, for example, the nucleic acid and amino acid sequences for:

1.44.1=1.44.2=1.44.3=1.44;
1.124=1.148=1.140=1.140.1;
1.41=1.43=143.1=143.2=1.22.1;
1.14.1=1.14.2=1.14.3=1.14;
1.100.1=1.100.2=1.100.3=1.100;
1.107=1.104=1.128=1.96=1.99=1.96.2;
1.18.1=1.18.2=1.18.3=1.18;
1.20=1.19=1.20.1;
1.39=1.39.1=1.39.2=1.39.3;
1.24=1.22.2=1.71.1=1.24.3;
1.71.2=1.71.3;
are identical.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include an anti-ErbB2 antibody that has been affinity purified using ErbB2, an anti-ErbB2 antibody that has been synthesized by a hybridoma or other cell line in vitro, and a human anti-ErbB2 antibody derived from a transgenic mouse. Targeted binding agents can also be purified using similar techniques described herein.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "modulating" as used herein refers to any amount of inhibition or activation of a pathway.

In certain embodiments, amino acid substitutions to an anti-ErbB2 antibody or antigen-binding portion thereof are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to ErbB2. Analogs can include various muteins of a sequence other than the normally-occurring peptide sequence. For example, single or multiple amino acid substitutions, preferably conservative amino acid substitutions, may be made in the normally-occurring sequence, preferably in the portion of the polypeptide outside the domain(s) forming intermolecular contacts. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al., Nature 354:105 (1991), incorporated herein by reference.

Non-peptide analogs are commonly used in the pharmaceutical industry as drugs with properties analogous to those of the template peptide. These types of non-peptide compound are termed "peptide mimetics" or "peptidomimetics." Fauchere, J. Adv. Drug Res. 15:29 (1986); Veber and Freidinger, TINS p. 392 (1985); and Evans et al., J. Med. Chem. 30:1229 (1987), incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH2NH—, —CH2S—, —CH═CH—(cis and trans), —COCH2—, —CH(OH)CH2—, and —CH2SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, Ann. Rev. Biochem. 61:387 (1992), incorporated herein by reference); for example, by adding internal cysteine residues capable of forming intramolecular disulfide bridges which cyclize the peptide.

Where an "antibody" is referred to herein with respect to the invention, it is normally understood that an antigen-binding portion thereof may also be used. An antigen-binding portion competes with the intact antibody for specific binding. See generally, Fundamental Immunology, Ch. 7 (Paul, W., ed., 2nd ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', F(ab')2, Fd, Fv, dAb, and complementarity determining region (CDR) fragments, single-chain antibodies (scFv or scFv2), chimeric antibodies, diabodies and polypeptides that contain at least a portion of an antibody that is sufficient to confer specific antigen binding to the polypeptide.

From N-terminus to C-terminus, both the mature light and heavy chain variable domains comprise the regions FR1, CDR1, FR2, CDR2, FR3, CDR3 and FR4. The assignment of amino acids to each domain herein is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987) or Chothia et al., Nature 342:878-883 (1989).

As used herein, an antibody that is referred to by number is the same as a monoclonal antibody that is obtained from the hybridoma of the same number. For example, monoclonal antibody 1.18 is the same antibody as one obtained from hybridoma 1*18, or a subclone thereof. Subclones are identified with a further decimal, for example 1.18.1.

As used herein, an Fd fragment means an antibody fragment that consists of the VH and CH1 domains; an Fv fragment consists of the VL and VH domains of a single arm of an antibody; and a dAb fragment (Ward et al., Nature 341:544-546 (1989)) consists of a VH domain.

In some embodiments, the antibody is a single-chain antibody (scFv) in which a VL and VH domains are paired to form a monovalent molecules via a synthetic linker that enables them to be made as a single protein chain. (Bird et al., Science 242:423-426 (1988) and Huston et al., Proc. Natl. Acad. Sci. USA 85:5879-5883 (1988).) In some embodiments, the antibodies are diabodies, i.e., are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., Proc. Natl. Acad. Sci. USA 90:6444-6448 (1993), and Poljak R. J. et al., Structure 2:1121-1123 (1994).) In some embodiments, one or more CDRs from an antibody of the invention may be incorporated into a molecule either covalently or noncovalently to make it an immunoadhesin that specifically binds to ErbB2. In such embodiments, the CDR(s) may be incorporated as part of a larger polypeptide chain, may be covalently linked to another polypeptide chain, or may be incorporated noncovalently.

In embodiments having one or more binding sites, the binding sites may be identical to one another or may be different.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells. These antibodies may be prepared in a variety of ways, as described below.

The term "chimeric antibody" as used herein means an antibody that comprises regions from two or more different antibodies. In one embodiment, one or more of the CDRs of the chimeric antibody are derived from a human anti-ErbB2 antibody. In another embodiment, all of the CDRs are derived from a human anti-ErbB2 antibody. In another embodiment, the CDRs from more than one human anti-ErbB2 antibodies are combined in a chimeric antibody. For instance, a chimeric antibody may comprise a CDR1 from the light chain of a first human anti-ErbB2 antibody, a CDR2 from the light chain of a second human anti-ErbB2 antibody and a CDR3 from the light chain of a third human anti-ErbB2 antibody, and CDRs from the heavy chain may be derived from one or more other anti-ErbB2 antibodies. Further, the framework regions may be derived from one of the anti-ErbB2 antibodies from which one or more of the CDRs are taken or from one or more different human antibodies.

In some embodiments, a chimeric antibody of the invention is a humanized anti-ErbB2 antibody. A humanized anti-ErbB2 antibody of the invention comprises the amino acid sequence of one or more framework regions and/or the amino acid sequence from at least a portion of the constant region of one or more human anti-ErbB2 antibodies of the invention and CDRs derived from a non-human anti-ErbB2 antibody.

An "inhibiting antibody" (also referred to herein as an "antagonist antibody") as used herein means an antibody that inhibits one or more ErbB2 activities by at least about 30% when added to a cell, tissue or organism expressing ErbB2. In some embodiments, the antibody inhibits ErbB2 activity by at least 40%, 50%, 60%, 70%, 80%, 85%, 90%, 95%, 100% or greater than 100%. In some embodiments, the inhibiting antibody is added in the presence of ligand such as heregulin. In some embodiments, an antagonist antibody of the invention decreases at least one activity of ErbB2 by 5-fold.

"Binding fragments" of an antibody are produced by recombinant DNA techniques, or by enzymatic or chemical cleavage of intact antibodies. Binding fragments include Fab, Fab', F(ab')7, Fv, dAb and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. See Bowie et al., Science 253:164 (1991).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al (1990) Nature, 348, 552-554) the Fd fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al., Nature 341, 544-546 (1989), McCafferty et al (1990) Nature, 348, 552-554, Holt et al (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, (1988) Science, 242, 423-426, et al, (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al, Proc. Natl. Acad. Sci. USA 90 6444-6448,). Fv, scFv or diabody molecules may be stabilized by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al, (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

An "inhibiting targeted binding agent" as used herein means a targeted binding agent that inhibits one or more ErbB2 activities by at least about 30% when added to a cell, tissue or organism expressing ErbB2. In some embodiments, the targeted binding agent inhibits ErbB2 activity by at least about 40%, 50%, 60%, 70%, 80%, 85%, 90%, 95%, 100% or greater than 100%. In some embodiments, the inhibiting targeted binding agent is added in the presence of ligand such as heregulin. In some embodiments, the targeted binding agent of the invention decreases at least one activity of ErbB2 by 5-fold.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin. 51:19-26 (1993); Jonsson U. et al., Biotechniques 11:620-627 (1991); Jonsson B. et al., J. Mol. Recognit. 8:125-131 (1995); and Johnsson B. et al., Anal. Biochem. 198:268-277 (1991).

The term "KD" refers to the equilibrium dissociation constant of a particular antibody-antigen interaction.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. An antibody is said to specifically bind an antigen when the dissociation constant is ≤1 mM, preferably ≤100 nM and most preferably ≤10 nM. In certain embodiments, the KD is 1 pM to 500 pM. In other embodiments, the KD is between 500 pM to 1 μM. In other embodiments, the KD is between 1 μM to 100 nM. In other embodiments, the KD is between 100 mM to 10 nM. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 03/48731.

As used herein, the twenty conventional amino acids and their abbreviations follow conventional usage. See Immunology—A Synthesis (2nd Edition, E. S. Golub and D. R. Oren, Eds., Sinauer Associates, Sunderland, Mass. (1991)), incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., Nucl. Acids Res. 14:9081 (1986); Stec et al., J. Am. Chem. Soc. 106:6077 (1984); Stein et al., Nucl. Acids Res. 16:3209 (1988); Zon et al., Anti-Cancer Drug Design 6:539 (1991); Zon et al., Oligonucleotides and Analogues: A Practical Approach, pp. 87-108 (F. Eckstein, Ed., Oxford University Press, Oxford England (1991)); U.S. Pat. No. 5,151,510; Uhlmann and Peyman, Chemical Reviews 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "CDR region" or "CDR" is intended to indicate the hypervariable regions of the heavy and light chains of the immunoglobulin as defined by Kabat et al. 1991 (Kabat, E. A. et al. (1991) Sequences of Proteins of Immunological Interest, 5th Edition. US Department of Health and Human Services, Public Service, NIH, Washington), and later editions, or as defined herein. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974, Amit et al., Science, 233:747-753, 1986, Chothia et al., J. Mol. Biol., 196:901-917, 1987, Chothia et al., Nature, 342:877-883, 1989, Caton et al., J. Immunol., 144:1965-1968, 1990, Sharon et al., PNAS, 87:4814-4817, 1990, Sharon et al., J. Immunol., 144:4863-4869, 1990, Kabat et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

The term "percent sequence identity" in the context of nucleotide sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); incorporated herein by reference). Unless otherwise specified, default parameters for a particular program or algorithm are used. For instance, percent sequence identity between nucleotide sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

As used herein, the terms "percent sequence identity" and "percent sequence homology" are used interchangeably.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, Methods Mol. Biol. 243:307-31 (1994). Examples of groups of amino acids that have side chains with similar chemical properties include 1) aliphatic side chains:

glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256:1443-45 (1992), incorporated herein by reference. A "moderately conservative" replacement is any change having a nonnegative value in the PAM250 log-likelihood matrix.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and a mutein thereof. See, e.g., GCG Version 6.1 (University of Wisconsin, Wis.). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). Another preferred algorithm when comparing a sequence of the invention to a database containing a large number of sequences from different organisms is the computer program BLAST, especially blastp or tblastn, using default parameters as supplied with the programs. See, e.g., Altschul et al., J. Mol. Biol. 215:403-410 (1990); Altschul et al., Nucleic Acids Res. 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., Science 253:164 (1991). Thus, the foregoing examples demonstrate that those of skill in the art can recognize sequence motifs and structural conformations that may be used to define structural and functional domains in accordance with the antibodies described herein.

An antigen binding site is generally formed by the variable heavy (VH) and variable light (VL) immunoglobulin domains, with the antigen-binding interface formed by six surface polypeptide loops, termed complimentarity determining regions (CDRs). There are three CDRs in each VH (HCDR1, HCDR2, HCDR3) and in each VL LCDR1, LCDR2, LCDR3), together with framework regions (FRs).

Typically, a VH domain is paired with a V L domain to provide an antibody antigen-binding site, although a VH or VL domain alone may be used to bind antigen. The VH domain (see Table 4) may be paired with the VL domain (see Table 5), so that an antibody antigen-binding site is formed comprising both the VH and VL domains. Analogous embodiments are provided for the other VH and VL domains disclosed herein. In other embodiments, VH chains in Table 4 are paired with a heterologous VL domain in Table 5. Light-chain promiscuity is well established in the art. Again, analogous embodiments are provided by the invention for the other VH and VL domains disclosed herein. Thus, the VH of the parent or of any of antibodies chain on Table 4 may be paired with the VL of the parent or of any of antibodies on Table 5 or other antibody.

An antigen binding site may comprise a set of H and/or L CDRs of the parent antibody or any of antibodies in Table 1 with as many as twenty, sixteen, ten, nine or fewer, e.g. one, two, three, four or five, amino acid additions, substitutions, deletions, and/or insertions within the disclosed set of H and/or L CDRs. Alternatively, an antigen binding site may comprise a set of H and/or L CDRs of the parent antibody or any of antibodies Table 1 with as many as twenty, sixteen, ten, nine or fewer, e.g. one, two, three, four or five, amino acid substitutions within the disclosed set of H and/or L CDRs. Such modifications may potentially be made at any residue within the set of CDRs.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Brandon and J. Tooze, eds., Garland Publishing, New York, N.Y. (1991)); and Thornton et al., Nature 354:105 (1991), which are each incorporated herein by reference.

A further aspect of the invention is an antibody molecule comprising a VH domain that has at least about 60, 70, 80, 85, 90, 95, 98 or about 99% amino acid sequence identity with a VH domain of any of antibody listed in Table 1, the appended sequence listing, an antibody described herein or with an HCDR (e.g., HCDR1, HCDR2, or HCDR3) shown in Table 4 or Table 4(a). The antibody molecule may optionally also comprise a VL domain that has at least about 60, 70, 80, 85, 90, 95, 98 or about 99% amino acid sequence identity with a VL domain of any of antibody listed in Table 1, the appended sequence listing, an antibody described herein or with an LCDR (e.g., LCDR1, LCDR2, or LCDR3) shown in Table 5. Algorithms that can be used to calculate % identity of two amino acid sequences comprise e.g. BLAST (Altschul et al. (1990) J. Mol. Biol. 215: 405-410), FASTA (Pearson and Lipman (1988) PNAS USA 85: 2444-2448), or the Smith-Waterman algorithm (Smith and Waterman (1981) J. Mol. Biol. 147: 195-197), e.g. employing default parameters.

Furthermore, variants of the VH and VL domains and CDRs of the present invention, including those for which amino acid sequences are set out herein, and which can be employed in targeted binding agents and antibodies for ERBB2 can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralization of an antigen activity relative to known antibodies which are specific for the antigen if the activity is known; specified competitive ability with a known antibody or ligand to the antigen at a specific molar ratio; ability to immunoprecipitate complex; ability to bind to a specified epitope; linear epitope, e.g. peptide sequence identified using peptide-binding scan as described herein, e.g. using peptides screened in linear and/or constrained conformation; conformational epitope, formed by non-continuous residues; ability to modulate a new biological activity of ERBb2, or downstream molecule. Such methods are also provided herein.

Variants of antibody molecules disclosed herein may be produced and used in the present invention. Following the lead of computational chemistry in applying multivariate data analysis techniques to the structure/property-activity relationships (Wold, et al. Multivariate data analysis in chemistry. Chemometries—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al. Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Chose, Arup K. & Viswanadhan, Vellarkad N. Combinatorial Library Design and Evaluation Principles, Software, Tools, and Applications in Drug Discovery). The properties of antibodies can be derived from empirical and theoretical models (for example, analysis of likely contact residues or calculated physicochemical property) of antibody sequence, functional and three-dimensional structures and these properties can be considered singly and in combination.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule using any freely available or commercial package, such as WAM. A protein visualisation and analysis software package, such as Insight II (Accelrys, Inc.) or Deep View may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and/or targeted binding agents generally are available in the art. Variant sequences may be made, with substitutions that may or may not be predicted to have a minimal or beneficial effect on activity, and tested for ability to bind and/or neutralize a target and/or for any other desired property.

Variable domain amino acid sequence variants of any of the VH and VL domains whose sequences are specifically disclosed herein may be employed in accordance with the present invention, as discussed.

As used herein, the terms "label" or "labeled" refers to incorporation of another molecule on the antibody or targeted binding agent. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 32P, 33P, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

As used herein, a "targeted binding agent" is an agent, e.g. antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. As described below, a targeted binding agent may comprise at least one antigen binding domain of an antibody, wherein said domain is fused or contained within a heterologous protein scaffold, e.g. a non-antibody protein scaffold.

Throughout this specification and claims, the word "comprise," or variations such as "comprises" or "comprising," will be understood to imply the inclusion of a stated integer or group of integers but not the exclusion of any other integer or group of integers.

Human Anti-ErbB2 Antibodies and Characterization Thereof

In one embodiment, the invention provides anti-ErbB2 targeted binding agent. In another embodiment, the invention provides anti-ErbB2 antibodies. In some embodiments, the anti-ErbB2 antibodies are human antibodies. In some embodiments, the invention provides anti-ErbB2 antibodies that bind to human ErbB2 without the signal sequence, amino acids 1-22 (Genbank ID: P04626) (SEQ ID NO:45). In some embodiments, human anti-ErbB2 antibodies are produced by immunizing a non-human transgenic animal, e.g., a rodent, whose genome comprises human immunoglobulin genes so that the transgenic animal produces human antibodies.

An anti-ErbB2 antibody of the invention can comprise a human kappa or a human lambda light chain or an amino acid sequence derived therefrom. In some embodiments comprising a kappa light chain, the light chain variable domain (VL) is encoded in part by a human VK1, VK2, or VK4 family gene. In certain embodiments, the light chain utilizes a human VK A1, VK A2, VK B3, or VK L1 gene.

In various embodiments, the light chain variable domain utilizes a human A2 gene and a human JK1 gene; a human L1 gene and a human JK5 gene; a human B3 gene and a human JK3 gene; or a human A1 gene and a human JK4 gene.

In some embodiments, the VL of the ErbB2 antibody comprises one or more amino acid substitutions relative to the germline amino acid sequence of the human gene. In some embodiments, the VL of the anti-ErbB2 antibody comprises 1, 2, 3, 4, 5, 6, 7, 8, 9, 10, 11, 12, or 13 amino acid substitutions relative to the germline amino acid sequence. In some embodiments, the VL of the anti-ErbB2 antibody comprises 0, 1, or 2 amino acid insertions relative to the germline amino acid sequence. In some embodiments, one or more of those substitutions from germline is in the CDR regions of the light chain. In some embodiments, the amino acid substitutions relative to germline are at one or more of the same positions as the substitutions relative to germline in any one or more of the VL of antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3. For example, the VL of an anti-ErbB2 antibody of the invention may contain one or more amino acid substitutions compared to germline found in the VL of antibody 1.14, or there may be one or more of the amino acid substitutions compared to germline found in the VL of antibody 1.18. In some embodiments, the amino acid changes are at one or more of the same positions, but involve a different substitution than in the reference antibody.

In some embodiments, amino acid changes relative to germline occur at one or more of the same positions as in any of the VL of antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3, but the changes may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline is serine, one may conservatively substitute threonine for serine at that position. Conservative amino acid substitutions are discussed supra.

In some embodiments, the light chain of the human anti-ErbB2 antibody comprises the VL amino acid sequence of antibody 1.44.1 (SEQ ID NO:4), 1.140 (SEQ ID NO:8), 1.4-3.1 (SEQ ID NO:12), 1.1-4.1 (SEQ ID NO:16), 1.100.1 (SEQ ID NO:20), 1.9-6.2 (SEQ ID NO:24), 1.1-8.1 (SEQ ID NO:28), 1.2-0.1 (SEQ ID NO:32), 1.3-9.1 (SEQ ID NO:36), 1.2-4.3 (SEQ ID NO:40), 1.7-1.3 (SEQ ID NO:44) or said amino acid sequence having up to 1, 2, 3, 4, 5, 6, 7, 8, 9, 10, 11, 12, or 13 conservative amino acid substitutions and/or a total of up to 3 non-conservative amino acid substitutions.

In certain embodiments, the light chain of the anti-ErbB2 antibody comprises the light chain CDR1, CDR2 and CDR3 regions of an antibody comprising the amino acid sequence of the VL region of an antibody selected from antibody 1.44.1 (SEQ ID NO:4), 1.140 (SEQ ID NO:8), 1.4-3.1 (SEQ ID NO:12), 1.1-4.1 (SEQ ID NO:16), 1.100.1 (SEQ ID NO:20), 1.9-6.2 (SEQ ID NO:24), 1.1-8.1 (SEQ ID NO:28), 1.2-0.1 (SEQ ID NO:32), 1.3-9.1 (SEQ ID NO:36), 1.2-4.3 (SEQ ID NO:40), 1.7-1.3 (SEQ ID NO:44) or said CDR regions each having less than 4 or less than 3 conservative amino acid substitutions and/or a total of three or fewer non-conservative amino acid substitutions.

With regard to the heavy chain, in some embodiments, the variable domain (VH) is encoded in part by a human VH3 or VH4 family gene. In certain embodiments, the heavy chain VH utilizes a human VH3-21, VH3-13, VH4-31, or VH3-7 gene. In various embodiments, the heavy chain VH utilizes a human VH3-21 gene, a human D5-24 gene and a human JH4B gene. In other embodiments, the heavy chain VH utilizes a human VH3-7 gene, and a human JH6; a human VH4-31 gene, a human D3-10 gene and a human JH6B gene; or a human VH3-13 gene, a human D6-19 gene and a human JH6B gene. In some embodiments, the VH sequence of the anti-ErbB2 antibody contains one or more amino acid substitutions, deletions or insertions (additions) relative to the germline amino acid sequence.

In some embodiments, the variable domain of the heavy chain comprises 1, 2, 3, 4, 5, 6, or 7 mutations from the germline amino acid sequence; 0, 1, 2, or 3 of which maybe substitutions. In some embodiments, the variable domain of the heavy chain comprises 0, 1, 2, or 3 additions compared to the germline amino acid sequence. In some embodiments, the mutation(s) are non-conservative substitutions compared to the germline amino acid sequence. In some embodiments, the mutations are in the CDR regions of the heavy chain. In some embodiments, the amino acid changes are made at one or more of the same positions as the mutations from germline in any one or more of the VH of antibodies 1.14.1, 1.18.1, 1.19, 1.20.1, 1.22.1, 1.22.2, 1.24.3, 1.41, 1.43.1, 143.2, 1.44.1, 1.39.1, 1.71.1, 1.71.3, 1.96.2, 1.99, 1.100.1, 1.104, 1.107, 1.124, 1.128, 1.140.1, or 1.148. In other embodiments, the amino acid changes are at one or more of the same positions but involve a different mutation than in the reference antibody.

In some embodiments, the heavy chain comprises the VH amino acid sequence of antibody 1.44.1 (SEQ ID NO:2), 1.140.1 (SEQ ID NO:6), 1.4-3.1 (SEQ ID NO:10), 1.14.1 (SEQ ID NO:14), 1.100.1 (SEQ ID NO:18), 1.9-6.2 (SEQ ID NO:22), 1.1-8.1 (SEQ ID NO:26), 1.2-0.1 (SEQ ID NO:30), 1.3-9.1 (SEQ ID NO:34), 1.2-4.3 (SEQ ID NO:38), 1.7-1.3 (SEQ ID NO:42); or said VH amino acid sequence having up to 1, 2, 3, 4, 6, 8, or conservative amino acid substitutions and/or a total of up to 3 non-conservative amino acid substitutions.

In some embodiments, the heavy chain comprises the heavy chain CDR1, CDR2 and CDR3 regions of antibody 1.14.1, 1.18.1, 1.19, 1.20.1, 1.22.1, 1.22.2, 1.24.3, 1.41, 1.43.1, 143.2, 1.44.1, 1.39.1, 1.71.1, 1.71.3, 1.96.2, 1.99, 1.100.1, 1.104, 1.107, 1.124, 1.128, 1.140.1, or 1.148 or said CDR regions each having less than 5, less than 4, less than 3, or less than 2 conservative amino acid substitutions and/or a total of three or fewer non-conservative amino acid substitutions.

In another embodiment, the antibody comprises the light chain as disclosed above and a heavy chain as disclosed above. In a further embodiment, the light chain CDRs and the heavy chain CDRs are from the same antibody.

One type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to change any potential proteolytic sites in the antibody. Such sites may occur in a CDR or framework region of a variable domain or in the constant domain of an antibody. Substitution of cysteine residues and removal of proteolytic sites may decrease the risk of any heterogeneity in the antibody product and thus increase its homogeneity. Another type of amino acid substitution is to eliminate asparagine-glycine pairs, which form potential deamidation sites, by altering one or both of the residues. Still another type of amino acid substitution is at methionine residues to eliminate oxidation sites.

In some embodiments, the C-terminal lysine of the heavy chain of the anti ErbB2 antibody of the invention is cleaved. In various embodiments of the invention, the heavy and light chains of the anti-ErbB2 antibodies may optionally include a signal sequence.

In one aspect, the invention relates to inhibitory human anti-ErbB2 monoclonal antibodies and the hybridoma cell lines that produce them. Table 1 lists the sequence identifiers (SEQ ID NO:) of the nucleic acids encoding the variable domain of the heavy and light chains, and the corresponding deduced amino acid sequences.

TABLE 1

HUMAN ANTI-ErbB2 ANTIBODIES

SEQUENCE IDENTIFIER (SEQ ID NO:)
Variable Domain-Comprising Portion

| Monoclonal Antibody | Heavy | | Light | |
|---|---|---|---|---|
| | DNA | Protein | DNA | Protein |
| 1.44.1 | 1 | 2 | 3 | 4 |
| 1.140 | 5 | 6 | 7 | 8 |
| 1.43 | 9 | 10 | 11 | 12 |
| 1.14.1 | 13 | 14 | 15 | 16 |
| 1.100.1 | 17 | 18 | 19 | 20 |
| 1.96 | 21 | 22 | 23 | 24 |
| 1.18.1 | 25 | 26 | 27 | 28 |
| 1.20 | 29 | 30 | 31 | 32 |
| 1.39 | 33 | 34 | 35 | 36 |
| 1.24 | 37 | 38 | 39 | 40 |
| 1.71.3 | 41 | 42 | 43 | 44 |

Class and Subclass of Anti-ErbB2 Antibodies

The class and subclass of anti-ErbB2 antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some embodiments, the anti-ErbB2 antibody is a monoclonal antibody. The anti-ErbB2 antibody can be an IgG, an IgM, an IgE, an IgA, or an IgD molecule. In another embodiment, the anti-ErbB2 antibody is an IgG and is an IgG1, IgG2, IgG3, IgG4 subclass. In another preferred embodiment, the antibody is subclass IgG2 (see Kabat et al., (1991) *Sequences of Proteins of Immunological Interest,* 5th edn. US Department of Health and Human Services, Washington, D.C.).

Binding Affinity of Anti-ErbB2 Targeted Binding Agents and Antibodies to ErbB2

In some embodiments of the invention, targeted binding agents and/or anti-ErbB2 antibodies bind to ErbB2 with high affinity. In some embodiments, the targeted binding agent and/or anti-ErbB2 antibody binds to ErbB2 with a $K_D$ of 13.5 $10^{-9}$M or less using high resolution biocore analysis. In still other embodiments, the targeted binding agent and/or antibody binds to ErbB2 with a $K_D$ of $13 \times 10^{-9}$M, $13 \times 10^{-9}$M, $11 \times 10^{-9}$M, $12 \times 10^{-9}$M, $10 \times 10^{-9}$M, $5 \times 10^{-9}$M, $3 \times 10^{-9}$, $2 \times 10^{-9}$, $1 \times 10^{-9}$M or $5 \times 10^{-10}$ M or less using high resolution biocore analysis. In certain embodiments, the targeted binding agent and/or antibody binds to ErbB2 with substantially the same $K_D$ as an antibody selected from 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3. In still another preferred embodiment, the targeted binding agent and/or antibody binds to ErbB2 with substantially the same $K_D$ as an antibody that comprises a heavy chain variable domain having the amino acid sequence of the $V_H$ region found in SEQ ID NO: 2, 6, 10, 14, 18, 22, 26, 30, 34, 38, or 42, a light chain variable domain having the amino acid sequence of the $V_L$ region found in SEQ ID NO: 4, 8, 12, 16, 20, 24, 28, 32, 36, 40, 44, or both.

In another preferred embodiment, the antibody binds to ErbB2 with substantially the same $K_D$ as a targeted binding agent and/or an antibody that comprises the CDR regions of a light chain variable domain having the amino acid sequence of the $V_L$ region found in SEQ ID NO: 4, 8, 12, 16, 20, 24, 28, 32, 36, 40, 44 or that comprises the CDR regions of a heavy chain variable domain having the amino acid sequence the $V_H$ region found in SEQ ID NO: 2, 6, 10, 14, 18, 22, 26, 30, 34, 38, or 42, or both.

In some embodiments, the targeted binding agent and/or anti-ErbB2 antibody has a low dissociation rate constant ($k_{off}$). In some embodiments, the targeted binding agents and/or anti-ErbB2 antibody has a $k_{off}$ of $1.0 \times 10^{-3}$ s-1 or lower or a $k_{off}$ of $5.0 \times 10^{-4}$ s-1 or lower. In other preferred embodiments, the antibody binds to ErbB2 with a $k_{off}$ of $2 \times 10^{-4}$ s-1 or lower. In some embodiments, the $k_{off}$ is substantially the same as an antibody described herein, including an antibody selected from 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3. In some embodiments, the targeted binding agent and/or antibody binds to ErbB2 with substantially the same $k_{off}$ as an antibody that comprises the CDR regions of a heavy chain, or the CDR regions of a light chain from an antibody selected from 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3, or both. In some embodiments, the targeted binding agents and/or antibody binds to ErbB2 with substantially the same $k_{off}$ as an antibody that comprises a heavy chain variable domain having the amino acid sequence of the $V_H$ region found in SEQ ID NO: 2, 6, 10, 14, 18, 22, 26, 30, 34, 38, or 42, a light chain variable domain having the amino acid sequence of the $V_L$ region found in SEQ ID NO: 4, 8, 12, 16, 20, 24, 28, 32, 36, 40, 44 or both.

The binding affinity and dissociation rate of a targeted binding agent and an anti-ErbB2 antibody to ErbB2 can be determined by methods known in the art. The binding affinity can be measured by ELISAs, RIAs, flow cytometry, surface plasmon resonance, such as BIACORE™. The dissociate rate can be measured by surface plasmon resonance. Preferably, the binding affinity and dissociation rate is measured by surface plasmon resonance. More preferably, the binding affinity and dissociation rate are measured using BIACORE™. One can determine whether an antibody has substantially the same $K_D$ as an anti-ErbB2 antibody by using methods known in the art. Example 12 exemplifies a method for determining affinity constants of anti-ErbB2 monoclonal antibodies by flow cytometry.

Identification of ErbB2 Epitopes Recognized by Anti-ErbB2 Antibodies

The invention provides targeted binding agents and/or human anti-ErbB2 monoclonal antibodies that binds to ErbB2 and competes or competes with and/or binds the same epitope as: (a) an antibody selected from 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3; (b) an antibody that comprises a heavy chain variable domain having an amino acid sequence of the variable domain found in SEQ ID NO: 2, 6, 10, 14, 18, 22, 26, 30, 34, 38, or 42, (c) an antibody that comprises a light chain variable domain having an amino acid sequence of the variable domain of SEQ ID NO: 4, 8, 12, 16, 20, 24, 28, 32, 36, 40, 44, or (d) an antibody that comprises both a heavy chain variable domain as defined in (b) and a light chain variable domain as defined in (c). If two antibodies reciprocally compete with each other for binding to ErbB2, they are said to compete.

One can determine whether a targeted binding agent and/or an antibody binds to the same epitope or competes for binding with an anti-ErbB2 antibody by using methods known in the art. In one embodiment, one allows the anti-ErbB2 antibody of the invention to bind to ErbB2 under saturating conditions and then measures the ability of the test antibody to bind to ErbB2. If the test antibody is able to bind to ErbB2 at the same time as the anti-ErbB2 antibody, then the test antibody binds to a different epitope as the anti-ErbB2 antibody. However, if the test antibody is not able to bind to ErbB2 at the same time, then the test antibody binds to the same epitope, an overlapping epitope, or an epitope that is in close proximity to the epitope bound by the human anti-ErbB2 antibody. This experiment can be performed using ELISA, RIA, BIACORE™, or flow cytometry.

To test whether a targeted binding agent and/or an anti-ErbB2 antibody competes with another anti-ErbB2 antibody, one may use the competition method described above in two directions i.e. determining if the reference antibody blocks the test antibody and vice versa. In another embodiment, the experiment is performed using ELISA. Methods of determining $K_D$ are discussed further below.

Inhibition of ErbB2 Activity by Anti-ErbB2 Antibody

In various embodiments, the invention provides targeted binding agents and/or anti-ErbB2 antibodies that inhibits signaling via ErbB2. In one embodiment, the targeted binding agent and/or an anti-ErbB2 antibody inhibits ligand-induced signaling of ErbB2. In one embodiment, the targeted binding agent and/or an anti-ErbB2 antibody inhibits ligand-induced signaling of ErbB2 without blocking the binding of the ligand to ErbB2. In another embodiment, the ErbB2 is human. In another embodiment, the anti-ErbB2 antibody is a human antibody. In some embodiments the ligand is Heregulin-β. The $EC_{50}$ of the targeted binding agent and/or anti-ErbB2 antibody can be measured by detecting the binding of the antibody to the antigen in a direct binding assay monitored by ELISA or RIA, or via cell-based assays such as those described below. In one embodiment, the targeted binding agent and/or antibody or portion thereof inhibits the ligand-induced signaling via the ErbB2 receptor with an $EC_{50}$ of no more than 50 ng/ml, preferably no more than 25 ng/ml, more preferably no more than 10 ng/ml, even more preferably no more than 5 ng/ml. In some embodiments, the targeted binding agent and/or anti-ErbB2 antibody inhibits ligand-induced signaling of ErbB2 by at least 20%, 25%, 30%, 35%, 40%, 45%, 50%, 55%, 60%, 65%, 70%, 75%, 80%, 85%, 90%, 95% or 100%. Measuring inhibition can be accomplished by any means known in the art.

In another embodiment, the invention provides a targeted binding agent and/or an anti-ErbB2 antibody that inhibits phosphorylation of ErbB2. In various embodiments, the $EC_{50}$ of the targeted binding agent and/or antibody is no more than 50 ng/ml, preferably no more than 25 ng/ml, more preferably no more than 10 ng/ml, even more preferably no more than 5 ng/ml. In some embodiments, the targeted binding agents and/or anti-ErbB2 antibody inhibits phosphorylation of ErbB2 by at least 20%, 25%, 30%, 35%, 40%, 45%, 50%, 55%, 60%, 65%, 70%, 75%, 80%, 85%, 90%, 95% or 100%. Examples 4, 9, and 11 exemplify an ErbB2 phosphorylation assay.

In another embodiment, the invention provides a targeted binding agent and/or an anti-ErbB2 antibody that inhibits activation of the MAPK pathway. In various embodiments, the $EC_{50}$ of the targeted binding agent and/or antibody is no more than 50 ng/ml, preferably no more than 25 ng/ml, more preferably no more than 10 ng/ml, even more preferably no more than 5 ng/ml. In some embodiments, the targeted binding agent and/or anti-ErbB2 antibody inhibits phosphorylation of ErbB2 by at least 20%, 25%, 30%, 35%, 40%, 45%, 50%, 55%, 60%, 65%, 70%, 75%, 80%, 85%, 90%, 95% or 100%. Assays for monitoring MAPK pathway activation in a cell are known in the art (see U.S. Patent Application Nos. 20030186382, and 20030096333, herein incorporated by reference in their entireties for all purposes).

In another embodiment, the invention provides a targeted binding agent and/or an anti-ErbB2 antibody that modulates the activity of the p38-TSP-1 pathway. In some embodiments, the targeted binding agent and/or antibody activates the p38-TSP-1 pathway. In other embodiments, the targeted binding agent and/or antibody inhibits the p38-TSP-1 pathway. In various embodiments, the $EC_{50}$ of the targeted binding agent and/or antibody is no more than 50 ng/ml, preferably no more than 25 ng/ml, more preferably no more than 10 ng/ml, even more preferably no more than 5 ng/ml. In some embodiments, the targeted binding agent and/or anti-ErbB2 antibody inhibits phosphorylation of ErbB2 by at least 20%, 25%, 30%, 35%, 40%, 45%, 50%, 55%, 60%, 65%, 70%, 75%, 80%, 85%, 90%, 95% or 100%. Assays for monitoring p38-TSP-1 pathway activation in a cell are known in the art (see U.S. Patent Application Nos. 20060089393 and 20020103253, herein incorporated by reference in their entireties for all purposes).

In another embodiment, the invention provides a targeted binding agent and/or an anti-ErbB2 antibody that inhibits activation of the PI3K pathway. In various embodiments, the $EC_{50}$ of the targeted binding agent and/or antibody is no more than 50 ng/ml, preferably no more than 25 ng/ml, more preferably no more than 10 ng/ml, even more preferably no more than 5 ng/ml. In some embodiments, the targeted binding agent and/or anti-ErbB2 antibody inhibits phosphorylation of ErbB2 by at least 20%, 25%, 30%, 35%, 40%, 45%, 50%, 55%, 60%, 65%, 70%, 75%, 80%, 85%, 90%, 95% or 100%. Assays for monitoring PI3K pathway activation in a cell are known in the art (see U.S. Patent Application Nos. 20020037276 and 20040176385, herein incorporated by reference in their entireties for all purposes).

In another embodiment, the invention provides a targeted binding agent and/or an anti-ErbB2 antibody that inhibits inhibition of CDC2. In various embodiments, the $EC_{50}$ of the targeted binding agent and/or the antibody is no more than 50 ng/ml, preferably no more than 25 ng/ml, more preferably no more than 10 ng/ml, even more preferably no more than 5 ng/ml. In some embodiments, the targeted binding agent and/or anti-ErbB2 antibody inhibits phosphorylation of ErbB2 by at least 20%, 25%, 30%, 35%, 40%, 45%, 50%, 55%, 60%, 65%, 70%, 75%, 80%, 85%, 90%, 95% or 100%. Assays for monitoring inhibition of CDC2 in a cell are known in the art (see U.S. Patent Application Nos. 20030225098 and 20040110775, herein incorporated by reference in their entireties for all purposes).

Inhibition of Cell Proliferation with Anti-ErbB2 Antibodies

According to some embodiments, the invention provides a targed binding agent and/or an anti-ErbB2 antibody that inhibits the proliferation of cancer or transformed cells in vivo or in vitro or both. In another embodiment, the targed binding agent and/or anti-ErbB2 antibody inhibits proliferation by at least 30%, 35%, 40%, 45%, 50%, 55%, 60%, 65%, 70%, 75%, 80%, 85%, 90%, 95% or 100%. In one embodiment, the phosphorylation is measured at least 1 day after the animals have started treatment with the antibody and proliferation is measured 3 days after the animals have started treatment with the antibody. In another embodiment, the inhibition is measured at least one hour after the animals have started treatment with the antibody. In various embodiments, the $EC_{50}$ of the targed binding agent and/or antibody, as measured by cell titer or a proliferation marker, is no more than 3.5 µg/ml, preferably no more than 300 ng/ml, more preferably no more than 100 ng/ml, even more preferably no more than 50 ng/ml. Examples 9 and 10 exemplify proliferation assays.

Species and Molecular Selectivity

In another aspect of the invention, the targeted binding agents and/or anti-ErbB2 antibodies demonstrate both species and molecular selectivity. In some embodiments, the targed binding agent and/or anti-ErbB2 antibody binds to human (SEQ ID NO:45) and cynomologus ErbB2. Following the teachings of the specification, one may determine the species selectivity for the targed binding agent and/or anti-ErbB2 antibody using methods well known in the art. For instance, one may determine the species selectivity using Western blot, flow cytometry, ELISA, immunoprecipitation or RIA. In another embodiment, one may determine the species selectivity using flow cytometry.

In some embodiments, the targed binding agent and/or anti-ErbB2 antibody does not exhibit any appreciable specific binding to any other protein other than ErbB2. One can determine the selectivity of the targed binding agent and/or anti-ErbB2 antibody for ErbB2 using methods well known in the art following the teachings of the specification. For instance one can determine the selectivity using Western blot, flow cytometry, ELISA, immunoprecipitation or RIA.

Methods of Producing Antibodies and Antibody Producing Cell Lines

In some embodiments, human antibodies are produced by immunizing a non-human, transgenic animal comprising within its genome some or all of human immunoglobulin heavy chain and light chain loci with an ErbB2 antigen. In another embodiment, the non-human animal is a XENOMOUSE™ animal. (Amgen Fremont, Inc., Fremont, Calif.).

XENOMOUSE™ mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-ErbB2 antibodies from non-human, non-mouse animals by immunizing non-human transgenic animals that comprise human immunoglobulin loci with an ErbB2 antigen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred embodiments of the current invention, the non-human animals are mammals, particularly rats, sheep, pigs, goats, cattle or horses.

XENOMOUSE™ mice produce an adult-like human repertoire of fully human antibodies and generate antigen-specific human antibodies. In some embodiments, the XENOM- OUSE™ mice contain approximately 80% of the human antibody V gene repertoire through introduction of germline configuration fragments of the human heavy chain loci and kappa light chain loci in yeast artificial chromosome (YAC). In other embodiments, XENOMOUSE™ mice further contain approximately all of the human lambda light chain locus. See Mendez et al., *Nature Genetics* 15:146-156 (1997), Green and Jakobovits, *J. Exp. Med.* 188:483-495 (1998), and WO 98/24893, the disclosures of which are hereby incorporated by reference. In other embodiments, the antibodies are produced in human trans-chromosomic mice (see WO 02/43478 and WO 02/092812, hereby incorporated by reference).

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter cilia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-ErbB2 antibodies. In some embodiments, non-human animals are immunized with an ErbB2 antigen as described below under conditions that permit antibody production. Antibody-producing cells are isolated from the animals, fused with myelomas to produce hybridomas, and nucleic acids encoding the heavy and light chains of an anti-ErbB2 antibody of interest are isolated. These nucleic acids are subsequently engineered using techniques known to those of skill in the art and as described further below to reduce the amount of non-human sequence, i.e., to humanize the antibody to reduce the immune response in humans In some embodiments, the ErbB2 antigen is isolated and/or purified ErbB2. In another embodiment, the ErbB2 antigen is human ErbB2. In some embodiments, the ErbB2 antigen is a fragment of ErbB2. In some embodiments, the ErbB2 fragment is an extracellular domain of ErbB2. In some embodiments, the ErbB2 fragment is an extracellular loop of ErbB2 (see Cho et al., Nature. 2003 Feb. 13; 421(6924):756-60, hereby incorporated by reference). In some embodiments, the ErbB2 fragment comprises at least one epitope of ErbB2. In other embodiments, the ErbB2 antigen is a cell that expresses or overexpresses ErbB2, or an immunogenic fragment thereof, on its surface. In some embodiments, the ErbB2 antigen is an ErbB2 fusion protein. In some embodiments, the ErbB2 is a synthetic peptide immunogen.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. In another embodiment, the ErbB2 antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example 1 exemplifies a method for producing anti-ErbB2 monoclonal antibodies in XenoMouse™ mice.

Production of Antibodies and Antibody-Producing Cell Lines

After immunization of an animal with an ErbB2 antigen, antibodies and/or antibody-producing cells can be obtained from the animal. In some embodiments, anti-ErbB2 antibody-containing serum is obtained from the animal by bleeding or sacrificing the animal. The serum may be used as it is obtained from the animal, an immunoglobulin fraction may be obtained from the serum, or the anti-ErbB2 antibodies may be purified from the serum.

In some embodiments, antibody-producing immortalized cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using ErbB2, a portion thereof, or a cell expressing ErbB2. In another embodiment, the initial screening is performed using an enzyme-linked immunoassay (ELISA) or a radioimmunoassay. An example of ELISA screening is provided in WO 00/37504, incorporated herein by reference.

Anti-ErbB2 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In one embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE™ mouse and the myeloma cell line is a non-secretory mouse myeloma. In an even more preferred embodiment, the myeloma cell line is P3-X63-Ag8.653 (American Type Culture Collection). See, e.g., Example 2.

Thus, in one embodiment, the invention provides methods for producing a cell line that produces a human monoclonal antibody or a fragment thereof directed to ErbB2 comprising (a) immunizing a non-human transgenic animal described herein with ErbB2, a portion of ErbB2 or a cell or tissue expressing ErbB2; (b) allowing the transgenic animal to mount an immune response to ErbB2; (c) isolating antibody-producing cells from transgenic animal; (d) immortalizing the antibody-producing cells; (e) creating individual monoclonal populations of the immortalized antibody-producing cells; and (f) screening the immortalized antibody-producing cells to identify an antibody directed to ErbB2.

In another aspect, the invention provides hybridomas that produce a human anti-ErbB2 antibody. In another embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In one embodiment of the invention, antibody-producing cells are isolated and expressed in a host cell, for example myeloma cells. In another preferred embodiment, a transgenic animal is immunized with ErbB2, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining region sequences. cDNAs of the heavy and light chain variable domains are then cloned and expressed in any suitable host cell as chimeric antibodies with respective immunoglobulin constant regions, such as the heavy chain and κ or), light chain constant domains. See Babcook, J. S. et al., Proc. Natl. Acad. Sci. USA 93:7843-48, 1996, incorporated herein by reference. Anti ErbB2 antibodies may then be identified and isolated as described herein.

In another embodiment, phage display techniques can be used to provide libraries containing a repertoire of antibodies with varying affinities for ErbB2. For production of such repertoires, it is unnecessary to immortalize the B cells from the immunized animal. Rather, the primary B cells can be used directly as a source of DNA. The mixture of cDNAs obtained from B cell, e.g., derived from blood or spleens, is used to prepare an expression library, for example, a human phage display library transfected into E. coli. The resulting cells are tested for immunoreactivity to ErbB2. Techniques for the identification of high affinity human antibodies from such libraries are described by Griffiths et al., *EMBO J.*, 13:3245-3260 (1994); Nissim et al., ibid, pp. 692-698 and by Griffiths et al., ibid, 12:725-734, which are incorporated by reference. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library. In certain embodiments, chain shuffling may be utilized (see Kang et al., PNAS (1991) December 15; 88(24): 11120-3, hereby incorporated by reference).

The phage library is then screened for the antibodies with the highest affinities for ErbB2 and the genetic material recovered from the appropriate clone. Further rounds of screening can increase affinity of the original antibody isolated.

Nucleic Acids, Vectors, Host Cells, and Recombinant Methods of Making Antibodies Nucleic Acids The present invention also encompasses nucleic acid molecules encoding anti-ErbB2 antibodies or antigen-binding portions thereof. In some embodiments, different nucleic acid molecules encode a heavy chain and a light chain of an anti-ErbB2 immunoglobulin. In other embodiments, the same nucleic acid molecule encodes a heavy chain and a light chain of an anti-ErbB2 immunoglobulin. In one embodiment, the nucleic acid encodes an ErbB2 antibody of the invention.

In some embodiments, the nucleic acid molecule encoding the variable domain of the light chain ($V_L$) utilizes a human Vκ B3, Vκ L1, Vκ A2, or Vκ A1 gene, and a Jκ1, Jκ3, Jκ4 or $J_k$5 gene with or without mutation from the germline.

In some embodiments, the nucleic acid molecule encoding the light chain, encodes an amino acid sequence comprising 1, 2, 3, 4, 5, 6, 7, 8, 9, 10, 11, 12, or 13 substitutions and/or 0, 1, or 2 insertions relative to the germline amino acid sequence(s). In some embodiments, the nucleic acid molecule comprises a nucleotide sequence that encodes a $V_L$ amino acid sequence comprising 1, 2, 3, 4, 5, 6, 7, 8, 9, 10, 11, 12, or 13 conservative amino acid substitutions and/or a total of up to 3 non-conservative substitutions compared to germline $V_K$ and $J_K$ sequences. Substitutions may be in the CDR regions, the framework regions, or in the constant domain.

In some embodiments, the nucleic acid molecule encodes a $V_L$ amino acid sequence comprising one or more variants compared to germline sequence that are identical to the variations found in the $V_L$ of any one of the antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3.

In some embodiments, the nucleic acid molecule encodes at least three amino acid substitutions compared to the germline sequence found in the $V_L$ of one of the antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3.

In some embodiments, the nucleic acid molecule comprises a nucleotide sequence that encodes the $V_L$ amino acid sequence of monoclonal antibody 1.44.1 (SEQ ID NO:4), 1.140 (SEQ ID NO:8), 1.4-3.1 (SEQ ID NO:12), 1.1-4.1 (SEQ ID NO:16), 1.100.1 (SEQ ID NO:20), 1.9-6.2 (SEQ ID NO:24), 1.1-8.1 (SEQ ID NO:28), 1.2-0.1 (SEQ ID NO:32), 1.3-9.1 (SEQ ID NO:36), 1.2-4.3 (SEQ ID NO:40), 1.7-1.3 (SEQ ID NO:44), or a variant or portion thereof. In some embodiments, the nucleic acid encodes an amino acid sequence comprising the light chain CDRs of one of said above-listed antibodies.

In some embodiments, the nucleic acid molecule comprises a nucleotide sequence that encodes the amino acid sequence of one of SEQ ID NO: 4, 8, 12, 16, 20, 24, 28, 32, 36, 40, or 44. In some preferred embodiments, the nucleic acid molecule comprises the nucleotide sequence of SEQ ID NO: 3, 7, 11, 15, 19, 23, 27, 31, 35, 39, 43, or a portion thereof.

In some embodiments, the nucleic acid encodes the amino acid sequence of the light chain CDRs of said antibody.

In some embodiments, the nucleic acid molecule encodes a $V_L$ amino acid sequence that is at least 70%, 75%, 80%, 85%, 90%, 95%, 97%, 98% or 99% identical to a $V_L$ amino acid sequence of a $V_L$ region of any one of antibodies 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3, or an amino acid sequence of any one of SEQ ID NO: 4, 8, 12, 16, 20, 24, 28, 32, 36, 40, or 44. Nucleic acid molecules of the invention include nucleic acids that hybridize under highly stringent conditions, such as those described above, to a nucleotide sequence encoding the amino acid sequence of a $V_L$ region found in SEQ ID NO: 4, 8, 12, 16, 20, 24, 28, 32, 36, 40, 44, or that has the nucleotide sequence of a nucleic acid molecule encoding the $V_L$ region found in SEQ ID NO: 3, 7, 11, 15, 19, 23, 27, 31, 35, 39, or 43.

In another embodiment, the nucleic acid encodes a full-length light chain of an antibody selected from 1.44.1, 1.140, 1.43, 1.14.1, 1.100.1, 1.96, 1.18.1, 1.20, 1.39, 1.24 and 1.71.31.44.1, 1.140, 1.43, 1.14.1, 1.100.1, 1.96, 1.18.1, 1.20, 1.39, 1.24 and 1.71.3.

In another preferred embodiment, the nucleic acid molecule encodes the variable domain of a heavy chain ($V_H$) that comprises a human $V_H$ 3-21, a human $V_H$ 3-7, a human $V_H$ 4-31, or a human $V_H$ 3-13 gene sequence or a sequence derived therefrom. In various embodiments, the nucleic acid molecule utilizes a human $V_H$3-7 gene, and a human $J_H$6; a human $V_H$4-31 gene, a human D3-10 gene and a human $J_H$6B gene; or a human $V_H$3-13 gene, a human D6-19 gene and a human $J_H$6B gene.

In some embodiments, the nucleic acid molecule encodes an amino acid sequence comprising 1, 2, 3, 4, 5, 6, or 7 mutations compared to the germline amino acid sequence of the human V, D and J genes; 0, 1, 2, or 3 of which maybe substitutions. In some embodiments, said mutations are in the $V_H$ region. In some embodiments, said mutations are in the CDR regions.

In some embodiments, the nucleic acid molecule encodes one or more amino acid mutations compared to the germline sequence that are identical to amino acid mutations found in the $V_H$ of monoclonal antibody 1.14.1, 1.18.1, 1.19, 1.20.1, 1.22.1, 1.22.2, 1.24.3, 1.41, 1.43.1, 143.2, 1.44.1, 1.39.1, 1.71.1, 1.71.3, 1.96.2, 1.99, 1.100.1, 1.104, 1.107, 1.124, 1.128, 1.140.1, or 1.148. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence that encodes at least a portion of the $V_H$ amino acid sequence of a antibody selected from 1.44.1 (SEQ ID NO:2), 1.140.1 (SEQ ID NO:6), 1.4-3.1 (SEQ ID NO:10), 1.1-4.1 (SEQ ID NO:14), 1.100.1 (SEQ ID NO:18), 1.9-6.2 (SEQ ID NO:22), 1.1-8.1 (SEQ ID NO:26), 1.2-0.1 (SEQ ID NO:30), 1.3-9.1 (SEQ ID NO:34), 1.2-4.3 (SEQ ID NO:38), 1.7-1.3 (SEQ ID NO:42), a variant thereof, or said sequence having conservative amino acid mutations and/or a total of three or fewer non-conservative amino acid substitutions. In various embodiments the sequence encodes one or more CDR regions, preferably a CDR3 region, all three CDR regions, or the entire $V_H$ region.

In some embodiments, the nucleic acid molecule comprises a nucleotide sequence that encodes the amino acid sequence of one of SEQ ID NO: 2, 6, 10, 14, 18, 22, 26, 30, 34, 38, and 42. In some preferred embodiments, the nucleic acid molecule comprises at least a portion of the nucleotide sequence of SEQ ID NO: 1, 5, 9, 13, 17, 21, 25, 29, 33, 37, or 41. In some embodiments, said portion encodes the $V_H$ region, a CDR3 region or all three CDR regions.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequence of any one of SEQ ID NO: 2, 6, 10, 14, 18, 22, 26, 30, 34, 38, or 42. Nucleic acid molecules of the invention include nucleic acids that hybridize under highly stringent conditions, such as those described above, to a nucleotide sequence encoding the amino acid sequence of SEQ ID NO: 1, 5, 9, 13, 17, 21, 25, 29, 33, 37, or 41, or to a $V_H$ region thereof, or that has the nucleotide sequence of SEQ ID NO: 1, 5, 9, 13, 17, 21, 25, 29, 33, 37, or 41 or that encodes a $V_H$ region thereof.

In another embodiment, the nucleic acid encodes a full-length heavy chain of an antibody selected from 1.44.1, 1.140, 1.43, 1.14.1, 1.100.1, 1.96, 1.18.1, 1.20, 1.39, 1.24 and 1.71.3.

A nucleic acid molecule encoding the heavy or light chain of an anti-ErbB2 antibody or portions thereof can be isolated from any source that produces such antibody. In various embodiments, the nucleic acid molecules are isolated from a B cell isolated from an animal immunized with ErbB2, from an immortalized cell derived from such a B cell that expresses an anti-ErbB2 antibody, or from a bacteriophage. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In one embodiment, the nucleic acid molecule is isolated from a hybridoma that has as one of its fusion partners a human immunoglobulin-producing cell from a non-human transgenic animal. In another embodiment, the human immunoglobulin producing cell is isolated from a XENOMOUSE™ animal. In another embodiment, the human immunoglobulin-producing cell is from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies. In another embodiment, the nucleic acid is isolated from bacteria or phage.

In some embodiments, a nucleic acid encoding a heavy chain of an anti-ErbB2 antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-ErbB2 antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and/or light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleotide sequences of human heavy and light chain immunoglobulin constant domain genes are known in the art. See, e.g., Kabat et al. *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-ErbB2 antibody isolated.

The nucleic acid molecules may be used to recombinantly express large quantities of anti-ErbB2 antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-ErbB2 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of antibodies 1.44.1, 1.140, 1.43, 1.14.1, 1.100.1, 1.96, 1.18.1, 1.20, 1.39, 1.24 and 1.71.3 (or variants thereof as described herein).

Vectors

The invention provides vectors comprising nucleic acid molecules that encode the heavy chain of an anti-ErbB2 antibody of the invention or an antigen-binding portion thereof, nucleic acid molecules that encode the light chain of such antibodies or antigen-binding portion thereof, or both or a targed binding agent. The invention further provides vectors comprising nucleic acid molecules encoding fusion proteins, modified antibodies, antibody fragments, and probes thereof.

In some embodiments, the anti-ErbB2 antibodies or antigen-binding portions of the invention are expressed by inserting DNAs encoding partial or full-length light and/or heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In some embodiments, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168, 062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Non-Hybridoma Host Cells and Methods of Recombinantly Producing Protein

Nucleic acid molecules encoding targed binding agent and/ or anti-ErbB2 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, N50 cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as SIP or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

Anti-ErbB2 antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-ErbB2 antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some embodiments, non-human transgenic animals that comprise human immunoglobulin loci are immunized with ErbB2 or an immunogenic portion thereof, as described above. Methods for making antibodies in plants are described, e.g., in U.S. Pat. Nos. 6,046,037 and 5,959,177, incorporated herein by reference.

In some embodiments, non-human transgenic animals or plants are produced by introducing one or more nucleic acid molecules encoding an anti-ErbB2 antibody of the invention into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual* $2^{nd}$ ed., Cold Spring Harbor Press (1999); Jackson et al., *Mouse Genetics and Transgenics: A Practical Approach*, Oxford University Press (2000); and Pinkert, Transgenic Animal Technology: A Laboratory Handbook, Academic Press (1999), all incorporated herein by reference. In some embodiments, the transgenic non-human animals have a targeted disruption and replacement by a targeting construct that encodes a heavy chain and/or a light chain of interest. In another embodiment, the transgenic animals comprise and express nucleic acid molecules encoding heavy and light chains that specifically bind to ErbB2, preferably human ErbB2. In some embodiments, the transgenic animals comprise nucleic acid molecules encoding a modified antibody such as a single-chain antibody, a chimeric antibody or a humanized antibody. The anti-ErbB2 antibodies may be made in any transgenic animal. In another embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-ErbB2 antibody or an antigen-binding portion thereof comprising the steps of synthesizing a library of human antibodies on phage, screening the library with ErbB2 or a portion thereof, isolating phage that bind ErbB2, and obtaining the antibody from the phage. By way of example, one method for preparing the library of antibodies for use in phage display techniques comprises the steps of immunizing a non-human animal comprising human immunoglobulin loci with ErbB2 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-ErbB2 antibodies of the invention may be obtained in this way.

Recombinant anti-ErbB2 human antibodies of the invention can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one embodiment, to isolate and produce human anti-ErbB2 antibodies with the desired characteristics, a human anti-ErbB2 antibody as described herein is first used to select human heavy and light chain sequences having similar binding activity toward ErbB2, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., *Nature* 348:552-554 (1990); and Griffiths et al., *EMBO J.* 12:725-734 (1993), all incorporated herein by reference. The scFv antibody libraries preferably are screened using human ErbB2 as the antigen.

Once initial human $V_L$ and $V_H$ domains are selected, "mix and match" experiments are performed, in which different pairs of the initially selected $V_L$ and $V_H$ segments are screened for ErbB2 binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to ErbB2.

Following screening and isolation of an anti-ErbB2 antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the invention provides a method for converting the class or subclass of an anti-ErbB2 antibody to another class or subclass. In some embodiments, a nucleic acid molecule encoding a $V_L$ or $V_H$ that does not include sequences encoding $C_L$ or $C_H$ is isolated using methods well-known in the art. The nucleic acid molecule then is operatively linked to a nucleotide sequence encoding a $C_L$ or $C_H$ from a desired immunoglobulin class or subclass. This can be achieved using a vector or nucleic acid molecule that comprises a $C_L$ or $C_H$ chain, as described above. For example, an anti-ErbB2 antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of an anti-ErbB2 antibody and a nucleic acid encoding a light chain of an anti-ErbB2 antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-ErbB2 antibody with the desired isotype.

Deimmunized Antibodies

In another aspect of the invention, the antibody may be deimmunized to reduce its immunogenicity using the techniques described in, e.g., PCT Publication Nos. WO98/52976 and WO00/34317 (incorporated herein by reference).

Mutated Antibodies

In another embodiment, the nucleic acid molecules, vectors and host cells may be used to make mutated anti-ErbB2 antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for ErbB2, to increase or decrease $k_{off}$, or to alter the binding specificity of the antibody. Techniques in site-directed mutagenesis are well-known in the art. See, e.g., Sambrook et al. and Ausubel et al., supra. In another embodiment, one or more mutations are made at an amino acid residue that is known to be changed compared to the germline in antibody 1.44.1, 1.140, 1.43, 1.14.1, 1.100.1, 1.96, 1.18.1, 1.20, 1.39, 1.24 and 1.71.3. The mutations may be made in a CDR region or framework region of a variable domain, or in a constant domain. In another embodiment, the mutations are made in a variable domain. In some embodiments, one or more mutations are made at amino acid residues that are known to be changed compared to the germline in a CDR region or framework region of a variable domain of an amino acid sequence selected from SEQ ID NO: 2, 4, 6, 8, 10, 12, 14, 16, 18, 20, 22, 24, 26, 28, 30, 32, 34, 36, 38, 40, 42, and 44, or whose nucleotide sequence is presented in SEQ ID NO: 1, 3, 5, 7, 9, 11, 13, 15, 17, 19, 21, 23, 25, 27, 29, 31, 33, 35, 37, 39, 41, or 43.

In another embodiment, the framework region is mutated so that the resulting framework region(s) have the amino acid sequence of the corresponding germline gene. A mutation may be made in a framework region or constant domain to increase the half-life of the anti-ErbB2 antibody. See, e.g., PCT Publication No. WO 00/09560, incorporated herein by reference. A mutation in a framework region or constant domain also can be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In some embodiments, there are from 1 to 8, including any number in between, amino acid mutations in either the $V_H$ or $V_L$ domains of the mutated anti-ErbB2 antibody compared to the anti-ErbB2 antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-ErbB2 antibody of the invention linked to another polypeptide. In another embodiment, only the variable domains of the anti-ErbB2 antibody are linked to the polypeptide. In another preferred embodiment, the $V_H$ domain of an anti-ErbB2 antibody is linked to a first polypeptide, while the $V_L$ domain of an anti-ErbB2 antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. The fusion antibody is useful for directing a polypeptide to an ErbB2-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence (Gly$_4$-Ser)$_3$, such that the V$_H$ and V$_L$ sequences can be expressed as a contiguous single-chain protein, with the V$_L$ and V$_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single V$_H$ and V$_L$ are used, bivalent, if two V$_H$ and V$_L$ are used, or polyvalent, if more than two V$_H$ and V$_L$ are used. Bispecific or polyvalent antibodies may be generated that bind specifically to ErbB2 and to another molecule.

In other embodiments, other modified antibodies may be prepared using anti-ErbB2 antibody encoding nucleic acid molecules. For instance, "Kappa bodies" (Ill et al., *Protein. Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol.* 148:1547-1553 (1992). In addition, bispecific antibodies may be formed as "diabodies" or "Janusins." In some embodiments, the bispecific antibody binds to two different epitopes of ErbB2. In some embodiments, the bispecific antibody has a first heavy chain and a first light chain from antibody 1.44.1, 1.140, 1.43, 1.14.1, 1.100.1, 1.96, 1.18.1, 1.20, 1.39, 1.24 and 1.71.3 and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-ErbB2 monoclonal antibody provided herein.

The antibodies of the invention also encompass antibodies that have half-lives (e.g., serum half-lives) in a mammal, preferably a human, of greater than that of an unmodified antibody. In one embodiment, said antibody half life is greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

An antigen binding site may be provided by means of arrangement of CDRs on non-antibody protein scaffolds, such as fibronectin or cytochrome B etc. (Haan & Maggos (2004) BioCentury, 12(5): A1-A6; Koide et al. (1998) Journal of Molecular Biology, 284: 1141-1151; Nygren et al. (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al. (Nygren et al. (1997) Current Opinion in Structural Biology, 7: 463-469). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12(42), A1-A7, 2004). Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a targeted binding agent according to the present invention may comprise other amino acids, e.g. forming a peptide or polypeptide, such as a folded domain, or to impart to the molecule another functional characteristic in addition to ability to bind antigen. Targeted binding agents of the invention may carry a detectable label, or may be conjugated to a toxin or a targeting moiety or enzyme (e.g. via a peptidyl bond or linker). For example, a targeted binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Derivatized and Labeled Antibodies

An anti-ErbB2 antibody or antigen-binding portion of the invention can be derivatized or linked to another molecule (e.g., another peptide or protein). In general, the antibodies or portion thereof are derivatized such that the ErbB2 binding is not affected adversely by the derivatization or labeling. Accordingly, the antibodies and antibody portions of the invention are intended to include both intact and modified forms of the human anti-ErbB2 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Il.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-napthalene-sulfonyl chloride, phycoerythrin, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-ErbB2 antibody can also be labeled with a radiolabeled amino acid. The radiolabel can be used for both diagnostic and therapeutic purposes. For instance, the radiolabel can be used to detect ErbB2-expressing cells by x-ray or other diagnostic techniques. Further, the radiolabel can be used therapeutically as a toxin for ErbB2-expressing cells, such as those which cause unwanted immune response. Examples of labels for polypeptides include, but are not limited to, the following radioisotopes or radionuclides: $^{3}H$, $^{14}C$, $^{15}N$, $^{35}S$, $^{90}Y$, $^{99}Tc$, $^{111}In$, $^{125}I$ and $^{131}I$.

In some embodiments, the anti-ErbB2 antibody can be labeled with a paramagnetic, radioactive or fluorogenic ion that is detectable upon imaging. In some embodiments, the paramagnetic ion is chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). In other embodiments, the radioactive ion is iodine123, technetium99, indium111, rhenium188, rhenium186, copper67, iodine131, yttrium90, iodine125, astatine211, and gallium67. In other embodiments, the anti-ErbB2 antibody is labeled with an X-ray imaging agent such as lanthanum (III), gold (III) lead (II) and bismuth (III). An anti-ErbB2 antibody can also be derivatized with a chemical group such as polyethylene glycol (PEG), a methyl or ethyl group, or a carbohydrate group. These groups are useful to improve the biological characteristics of the antibody, e.g., to increase serum half-life or to increase tissue binding.

Pharmaceutical Compositions and Kits

The invention relates to compositions comprising a targed binding agent and/or human anti-ErbB2 antibody with antagonist properties for the treatment of subjects in need of a therapeutic procedure including, but not limited to, those afflicted with cancer. In some embodiments, the subject of treatment is a human. In other embodiments, the subject is a veterinary subject.

Treatment may involve administration of one or more inhibitory anti-ErbB2 monoclonal antibodies of the invention, or antigen-binding fragments thereof, alone or with a pharmaceutically acceptable carrier. Inhibitory anti-ErbB2 antibodies of the invention and compositions comprising them, can be administered in combination with one or more other therapeutic, diagnostic or prophylactic agents.

In certain embodiments, the therapeutic agents of the disclosure may include antineoplastic agents. Antineoplastic agents include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alpha, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

In various embodiments, the antineoplastic agent is 5-Fluoruracil, 6-mercatopurine, Actinomycin, Adriamycin®, Admen®, Aminoglutethimide, Anastrozole, Aredia®, Arimidex®, Aromasin®, Bonefos®, Bleomycin, carboplatin, Cactinomycin, Capecitabine, Cisplatin, Clodronate, Cyclophosphamide, Cytadren®, Cytoxan®, Dactinomycin, Docetaxel, Doxyl®, Doxorubicin, Epirubicin, Etoposide, Exemestane, Femora®, Fluorouracil, Fluoxymesterone, Halotestin®, Herceptin®®, Letrozole, Leucovorin calcium, Megace®, Megestrol acetate, Methotrexate, Mitomycin, Mitoxantrone, Mutamycin®, Navelbine®, Nolvadex®, Novantrone®, Oncovin®, Ostac®, Paclitaxel, Pamidronate, Pharmorubicin®, Platinol®, prednisone, Procytox®, Tamofen®, Tamone®, Tamoplex®, Tamoxifen, Taxol®, Taxotere®, Trastuzumab, Thiotepa, Velbe®, Vepesid®, Vinblastine, Vincristine, Vinorelbine, Xeloda®, or a combination thereof.

In some embodiments, the antineoplastic agent comprises a monoclonal antibody, a humanized antibody, a chimeric antibody, a single chain antibody, or a fragment of an antibody. Exemplary antibodies include, but are not limited to, Rituxan, IDEC-C2B8, anti-CD20 Mab, Panorex, 3622W94, anti-EGP40 (17-1A) pancarcinoma antigen on adenocarcinomas Herceptin®, Erbitux, anti-Her2, Anti-EGFr, BEC2, anti-idiotypic-$GD_3$ epitope, Ovarex, B43.13, anti-idiotypic CA125, 4B5, Anti-VEGF, RhuMAb, MDX-210, anti-HER2, MDX-22, MDX-220, MDX-447, MDX-260, anti-GD-2, Quadramet, CYT-424, IDEC-Y2B8, Oncolym, Lym-1, SMART M195, ATRAGEN, LDP-03, anti-CAMPATH, for t6, anti CD6, MDX-11, OV103, Zenapax, Anti-Tac, anti-IL-2 receptor, MELIMMUNE-2, MELIMM UN E-1, CEACIDE, Pretarget, NovoMAb-G2, TNT, anti-histone, Gliomab-H, GNI-250, EMD-72000, LymphoCide, CMA 676, Monopharm-C, anti-FLK-2, SMART 1D10, SMART ABL 364, ImmuRAIT-CEA, or combinations thereof.

In yet another embodiment, the antineoplastic agent comprises an additional type of tumor cell. In a specific embodiment, the additional type of tumor cell is a MCF-10A, MCF-10F, MCF-10-2A, MCF-12A, MCF-12F, ZR-75-1, ZR-75-30, UACC-812, UACC-893, HCC38, HCC70, HCC202, HCC1007 BL, HCC1008, HCC1143, HCC1187, HCC1187 BL, HCC1395, HCC1569, HCC1599, HCC1599 BL, HCC1806, HCC1937, HCC1937 BL, HCC1954, HCC1954 BL, HCC2157, Hs 274.T, Hs 281.T, Hs 343.T, Hs 362.T, Hs 574.T, Hs 579.Mg, Hs 605.T, Hs 742.T, Hs 748.T, Hs 875.T, MB 157, SW527, 184A1, 184B5, MDA-MB-330, MDA-MB-415, MDA-MB-435S, MDA-MB-436, MDA-MB-453, MDA-MB-468 RT4, BT-474, CAMA-1, MCF7 [MCF-7], MDA-MB-134-VI, MDA-MB-157, MDA-MB-175-VII HTB-27 MDA-MB-361, SK-BR-3 or ME-180 cell, all of which are available from ATTC.

In still further embodiments, the antineoplastic agent comprises an antisense reagent, such as an siRNA or a hairpin RNA molecule, which reduces the expression or function of a gene that is expressed in a cancer cell. Exemplary antisense reagents which may be used include those directed to mucin, Ha-ras, VEGFR1 or BRCA1. Such reagents are described in U.S. Pat. No. 6,716,627 (mucin), U.S. Pat. No. 6,723,706 (Ha-ras), U.S. Pat. No. 6,710,174 (VEGFR1) and in U.S. Patent Publication No. 2004/0014051 (BRCA1).

In further embodiments, the antineoplastic agent comprises cells autologous to the subject, such as cells of the immune system such as macrophages, T cells or dendrites. In some embodiments, the cells have been treated with an antigen, such as a peptide or a cancer antigen, or have been incubated with tumor cells from the patient. In one embodiment, autologous peripheral blood lymphocytes may be mixed with SV-BR-1 cells and administered to the subject. Such lymphocytes may be isolated by leukaphoresis. Suitable autologous cells which may be used, methods for their isolation, methods of modifying said cells to improve their effectiveness and formulations comprising said cells are described in U.S. Pat. Nos. 6,277,368, 6,451,316, 5,843,435, 5,928,639, 6,368,593 and 6,207,147, and in International PCT Publications Nos. WO04/021995 and WO00/57705.

In some embodiments of the methods described herein directed to the treatment of cancer, the subject is treated prior to, concurrently with, or subsequently to the treatment with the cells of the present invention, with a complementary therapy to the cancer, such as surgery, chemotherapy, radiation therapy, or hormonal therapy or a combination thereof.

In a specific embodiment where the cancer is breast cancer, the complementary treatment may comprise breast-sparing surgery i.e. an operation to remove the cancer but not the breast, also called breast-sparing surgery, breast-conserving surgery, lumpectomy, segmental mastectomy, or partial mastectomy. In another embodiment, it comprises a mastectomy. A mastectomy is an operation to remove the breast, or as much of the breast tissue as possible, and in some cases also the lymph nodes under the arm. In yet another embodiment, the surgery comprises sentinel lymph node biopsy, where only one or a few lymph nodes (the sentinel nodes) are removed instead of removing a much larger number of underarm lymph nodes. Surgery may also comprise modified radical mastectomy, where a surgeon removes the whole breast, most or all of the lymph nodes under the arm, and, often, the lining over the chest muscles. The smaller of the two chest muscles also may be taken out to make it easier to remove the lymph nodes.

In a specific embodiment, the complementary treatment comprises radiation therapy. Radiation therapy may comprise external radiation, where radiation comes from a machine, or from internal radiation (implant radiation, wherein the radiation originates from radioactive material placed in thin plastic tubes put directly in the breast.

In another specific embodiment, the complementary treatment comprises chemotherapy. Chemotherapeutic agents found to be of assistance in the suppression of tumors include but are not limited to alkylating agents (e.g., nitrogen mustards), antimetabolites (e.g., pyrimidine analogs), radioactive isotopes (e.g., phosphorous and iodine), miscellaneous agents (e.g., substituted ureas) and natural products (e.g., vinca alkyloids and antibiotics). In a specific embodiment, the chemotherapeutic agent is selected from the group consisting of allopurinol sodium, dolasetron mesylate, pamidronate disodium, etidronate, fluconazole, epoetin alfa, levamisole HCL, amifostine, granisetron HCL, leucovorin calcium, sargramostim, dronabinol, mesna, filgrastim, pilocarpine HCL, octreotide acetate, dexrazoxane, ondansetron HCL, ondansetron, busulfan, carboplatin, cisplatin, thiotepa, melphalan HCL, melphalan, cyclophosphamide, ifosfamide, chlorambucil, mechlorethamine HCL, carmustine, lomustine, polifeprosan 20 with carmustine implant, streptozocin, doxorubicin HCL, bleomycin sulfate, daunirubicin HCL, dactinomycin, daunoruebicin citrate, idarubicin HCL, plimycin, mitomycin, pentostatin, mitoxantrone, valrubicin, cytarabine, fludarabine phosphate, floxuridine, cladribine, methotrexate, mercaptipurine, thioguanine, capecitabine, methyltestosterone, nilutamide, testolactone, bicalutamide, flutamide, anastrozole, toremifene citrate, estramustine phosphate sodium, ethinyl estradiol, estradiol, esterified estrogens, conjugated estrogens, leuprolide acetate, goserelin acetate, medroxyprogesterone acetate, megestrol acetate, levamisole HCL, aldesleukin, irinotecan HCL, dacarbazine, asparaginase, etoposide phosphate, gemcitabine HCL, altretamine, topotecan HCL, hydroxyurea, interferon alfa-2b, mitotane, procarbazine HCL, vinorelbine tartrate, *E. coli* L-asparaginase, *Erwinia* L-asparaginase, vincristine sulfate, denileukin diftitox, aldesleukin, rituximab, interferon alfa-2a, paclitaxel, docetaxel, BCG live (intravesical), vinblastine sulfate, etoposide, tretinoin, teniposide, porfimer sodium, fluorouracil, betamethasone sodium phosphate and betamethasone acetate, letrozole, etoposide citrororum factor, folinic acid, calcium leucouorin, 5-fluorouricil, adriamycin, cytoxan, and diamino dichloro platinum, said chemotherapy agent in combination with thymosin$\alpha_1$ being administered in an amount effective to reduce said side effects of chemotherapy in said patient.

In another specific embodiment, the complementary treatment comprises hormonal therapy. Hormonal therapy may comprise the use of a drug, such as tamoxifen, that can block the natural hormones like estrogen or may comprise aromatase inhibitors which prevent the synthesis of estradiol. Alternative, hormonal therapy may comprise the removal of the subject's ovaries, especially if the subject is a woman who has not yet gone through menopause.

As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In another embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-ErbB2 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, polylactic acid, chitosan and alginate. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

The invention also provides compositions suitable for administration by inhalation, which comprise the anti-ErbB2 antibodies described herein. The anti-ErbB2 antibodies may be conveniently delivered to a subject in the form of an aerosol spray presentation from pressurized packs or from a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. Dellamary et al., (2004) *J Control Release.*; 95(3): 489-500 describes formulations for the pulmonary delivery of antibodies.

The invention also provides compositions, suitable for administration through the oral mucosa, which comprise the anti-ErbB2 antibody described herein. Oral transmucosal delivery refers to the delivery of a delivery vehicle across a mucous membrane in the oral cavity, pharyngeal cavity, or esophagus, and may be contrasted, for example, with traditional oral delivery, in which absorption of a drug occurs in the intestine. Accordingly, routes of administration in which the anti-ErbB2 antibodies are absorbed through the buccal, sublingual, gingival, pharyngeal, and/or esophageal mucosa are all encompassed within "oral transmucosal delivery," as that term is used herein. For administration through the transmucosal mucosa, the anti-ErbB2 antibody may be formulated, for example, into chewing gums (see U.S. Pat. No. 5,711,961) or buccal patches (see e.g. U.S. Pat. No. 5,298,256).

The invention also provides compositions suitable for administration through the vaginal mucosa, which comprise the anti-ErbB2 antibodies described herein. The anti-ErbB2 antibodies of the invention may be formulated into a vaginal suppository, foam, cream, tablet, capsule, ointment, or gel.

In certain embodiments, the pharmaceutical compositions comprising the anti-ErbB2 antibodies are formulated with permeants appropriate to the transmucosal barrier to be permeated. Such penetrants are generally known in the art, and include, for example, for transmucosal administration bile salts and fusidic acid derivatives.

In certain embodiments, an anti-ErbB2 antibody of the invention is orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-ErbB2 antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, an inhibitory anti-ErbB2 antibody of the invention is co-formulated with and/or co-administered with one or more additional therapeutic agents, such as those listed supra. Such combination therapies may require lower dosages of the inhibitory anti-ErbB2 antibody as well as the co-administered agents, thus avoiding possible toxicities or complications associated with the various monotherapies.

Inhibitory anti-ErbB2 antibodies of the invention and compositions comprising them also may be administered in combination with other therapeutic regimens, in particular in combination with surgical radiological and/or chemotherapy treatment.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the subject, and the ability of the antibody or antibody portion to elicit a desired response in the subject. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the close can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-ErbB2 antibody or portion thereof and the particular therapeutic or prophylactic effect to be achieved, and (b) the limitations inherent in the art of compounding such an antibody for the treatment of sensitivity in subjects.

An exemplary, non-limiting range for a therapeutically or prophylactically effective amount of an antibody or antibody portion of the invention is 0.025 to 50 mg/kg, more preferably 0.1 to 50 mg/kg, more preferably 0.1 to 25, 0.1 to 10 or 0.1 to 3 mg/kg. In some embodiments, a formulation contains 5 mg/ml of antibody in a buffer of 20 mM sodium citrate, pH 5.5, 140 mM NaCl, and 0.2 mg/ml polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-ErbB2 antibody or antibody portion of the invention or a composition comprising such an antibody. A kit may include, in addition to the antibody or composition, diagnostic or therapeutic agents. A kit can also include instructions for use in a diagnostic or therapeutic method. In another embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

Diagnostic Methods of Use

In another aspect, the invention provides diagnostic methods. The anti-ErbB2 antibodies can be used to detect ErbB2 in a biological sample in vitro or in vivo. In one embodiment, the invention provides a method for diagnosing the presence or location of an ErbB2-expressing cells in a subject in need thereof, comprising the steps of administering the antibody into the subject, determining the expression of ErbB2 in the subject by localizing where the antibody has bound, comparing the expression in the subject with that of a normal reference subject or standard, and diagnosing the presence or location of the cells. The anti-ErbB2 antibodies may also be used as a marker of proliferation.

The anti-ErbB2 antibodies can be used in a conventional immunoassay, including, without limitation, an ELISA, an RIA, flow cytometry, tissue immunohistochemistry, Western blot or immunoprecipitation. The anti-ErbB2 antibodies of the invention can be used to detect ErbB2 from humans. In another embodiment, the anti-ErbB2 antibodies can be used to detect ErbB2 from cynomolgus monkeys or rhesus monkeys. In another embodiment, the anti-ErbB2 antibodies can be used to detect ErbB2 from rodents, such as mice and rats.

The invention provides a method for detecting ErbB2 in a biological sample comprising contacting the biological sample with an anti-ErbB2 antibody of the invention and detecting the bound antibody. In one embodiment, the anti-ErbB2 antibody is directly labeled with a detectable label. In another embodiment, the anti-ErbB2 antibody (the first antibody) is unlabeled and a second antibody or other molecule that can bind the anti-ErbB2 antibody is labeled. As is well known to one of skill in the art, a second antibody is chosen that is able to specifically bind the particular species and class of the first antibody. For example, if the anti-ErbB2 antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ and $^{3}H$.

In other embodiments, ErbB2 can be assayed in a biological sample by a competition immunoassay utilizing ErbB2 standards labeled with a detectable substance and an unlabeled anti-ErbB2 antibody. In this assay, the biological sample, the labeled ErbB2 standards and the anti-ErbB2 antibody are combined and the amount of labeled ErbB2 standard bound to the unlabeled antibody is determined. The amount of ErbB2 in the biological sample is inversely proportional to the amount of labeled ErbB2 standard bound to the anti-ErbB2 antibody.

One can use the immunoassays disclosed above for a number of purposes. For example, the anti-ErbB2 antibodies can be used to detect ErbB2 in cultured cells. In another embodiment, the anti-ErbB2 antibodies are used to determine the amount of ErbB2 on the surface of cells that have been treated with various compounds. This method can be used to identify compounds that modulate ErbB2 protein levels. According to this method, one sample of cells is treated with a test compound for a period of time while another sample is left untreated. If the total level of ErbB2 is to be measured, the cells are lysed and the total ErbB2 level is measured using one of the immunoassays described above. The total level of ErbB2 in the treated versus the untreated cells is compared to determine the effect of the test compound.

A preferred immunoassay for measuring total ErbB2 levels is flow cytometry or immunohistochemistry. If the cell surface level of ErbB2 is to be measured, the cells are not lysed, and the cell surface levels of ErbB2 are measured using one of the immunoassays described above. A preferred immunoassay for determining cell surface levels of ErbB2 includes the steps of labeling the cell surface proteins with a detectable label, such as biotin or $^{125}$I, immunoprecipitating the ErbB2 with an anti-ErbB2 antibody and then detecting the labeled ErbB2.

Another preferred immunoassay for determining the localization of ErbB2, e.g., cell surface levels, is by using immunohistochemistry. A preferred immunoassay to detect cell surface levels of ErbB2 includes binding of an anti-ErbB2 antibody labeled with an appropriate fluorophore, such as fluorescein or phycoerythrin, and detecting the primary antibody using flow cytometry. In another embodiment, the anti-ErbB2 antibody is unlabeled and a second antibody or other molecule that can bind the anti-ErbB2 antibody is labeled Methods such as ELISA, RIA, flow cytometry, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of ErbB2.

The anti-ErbB2 antibodies of the invention also can be used to determine the levels of ErbB2 in a tissue or in cells derived from the tissue. In one embodiment, the anti-ErbB2 antibodies are used to determine the infiltration of ErbB2-expressing cells into tissues that either do not express ErbB2 or that express it at reduced levels compared to the infiltrating cells. In some embodiments, the tissue is a diseased tissue. In some embodiments, the tissue is a tissue biopsy. In some embodiments of the method, a tissue or a biopsy thereof is excised from a subject. The tissue or biopsy is then used in an immunoassay to determine, e.g., total ErbB2 levels, cell surface levels of ErbB2 or localization of ErbB2 by the methods discussed above. Such methods can be used to determine whether a tissue expresses high levels of ErbB2, which could be indicative that the tissue is a target for treatment with anti-ErbB2 antibody.

The antibodies of the present invention also can be used in vivo to identify tissues and organs that express ErbB2. In some embodiments, the anti-ErbB2 antibodies are used to identify ErbB2-expressing cells. One advantage of using the human anti-ErbB2 antibodies of the present invention is that they may safely be used in vivo without eliciting a substantial immune response to the antibody upon administration, unlike antibodies of non-human origin or with humanized or chimeric antibodies. The method comprises the steps of administering a detectably labeled anti-ErbB2 antibody or a composition comprising them to a subject in need of such a diagnostic test and subjecting the subject to imaging analysis to determine the location of the ErbB2-expressing tissues. Imaging analysis is well known in the medical art, and includes, without limitation, x-ray analysis, magnetic resonance imaging (MRI) or computed tomography (CT). The antibody can be labeled with any agent suitable for in vivo imaging, for example a contrast agent, such as barium, which can be used for x-ray analysis, or a magnetic contrast agent, such as a gadolinium chelate, which can be used for MRI or CT. Other labeling agents include, without limitation, radio-isotopes, such as $^{99}$Tc. In another embodiment, the anti-ErbB2 antibody will be unlabeled and will be imaged by administering a second antibody or other molecule that is detectable and that can bind the anti-ErbB2 antibody. In another embodiment, a biopsy is obtained from the subject to determine whether the tissue of interest expresses ErbB2.

In some embodiments, the detectably labeled anti-ErbB2 antibody comprises a fluorophore. In certain embodiments, the fluorophore is selected from a near-infrared fluorescent dye, dinitrophenyl, fluorescein and derivatives thereof, rhodamine, derivatives of rhodamine, phycoerythrin, phycocyanin, allophycocyanin, o-phthaldehyde and fluorescamine, Texas red, Rhodamine green, Oregon green, Cascade blue, phycoerythrin, CY3, CY5, CY2, CY7, coumarin, infrared 40, MR 200, IRD 40, Alexa Fluor, Cascade Blue, Tetramethylrhodamine, Pacific Blue, SYBR, and BODIPY. In another embodiment, the fluorophore includes one of the following compounds with their emission maxima indicated in nm in parenthesis, Cy2™ (506), GFP (Red Shifted) (507), YO-PRO®-1 (509), YOYO®-1 (509), Calcein (517), FITC (518), FluorX® (519), Alexa® (520), Rhodamine 110 (520), 5-FAM (522), Oregon Green® 500 (522), Oregon Green® 488 (524), RiboGreen® (525), Rhodamine Green® (527), Rhodamine 123 (529), Magnesium Green® (531), Calcium Green® (533), TO-PRO®-1 (533), TOTO®-1 (533), JOE (548), BODIPY 12 530/550 (550), Dil (565), BODIPY® (568), BODIPY® 558/568 (568), BODIPY® 564/570 (570), Cy3® (570), Alexa® 546 (570), TRITC (572), Magnesium Orange® (575), Phycoerythrin R&B (575), Rhodamine Phalloidin (575), Calcium Orange® (576), Pyronin Y (580), Rhodamine B (580), TAMRA (582), Rhodamine Red® (590), Cy3.5® (596), ROX (608), Calcium Crimsom™ (615), Alexa® 594 (615), Texas Red® (615), Nile Red (628), YO-PRO®-3 (631), YOYO®-3 (631), R-phycocyanin (642), C-Phycocyanin (648), TO-PRO®-3 (660), TOTO®-3 (660), DiD DilC (5) (665), Cy5™ (670), Thiadicarbocyanine (671) and Cy5.5 (694).

Therapeutic Methods of Use

In another embodiment, the invention provides a method for inhibiting ErbB2 activity by administering a targed binding agent and/or an anti-ErbB2 antibody to a subject in need thereof. In another embodiment, the anti-ErbB2 antibody is a human, chimeric or humanized antibody. In another preferred embodiment, the ErbB2 is human and the subject is a human subject. Alternatively, the subject may be a mammal that expresses an ErbB2 with which the targed binding agent and/or anti-ErbB2 antibody cross-reacts. The targed binding agent and/or antibody may be administered to a non-human mammal expressing ErbB2 with which the antibody cross-reacts (i.e. a cynomologus monkey) for veterinary purposes or as an animal model of human disease. Such animal models may be useful for evaluating the therapeutic efficacy of antibodies of this invention.

In one embodiment, the invention provides methods of treating or preventing an ErbB2-mediated disorder in a subject by administering to the subject a therapeutically-effective amount of a targed binding agent and/or an anti-ErbB2 antibody of the invention. As used herein, the term "an ErbB2-mediated disorder" is intended to include diseases and other disorders in which the presence of high or increased levels of ErbB2 expression or activity in a subject suffering from the disorder have been shown to be, or are suspected of being, either responsible for the pathophysiology of the disorder or a factor that contributes to a worsening of the disorder. Such disorders may be evidenced, for example, by an increase in expression or the levels of ErbB2 on the cell surface in the affected cells or tissues of a subject suffering from the disorder, or by an increase in an ErbB2-mediated activity in a cell type, such as in a cancer cell, that contributes to the pathology of the disorder or that contributes to the worsening of the disorder. The increase in ErbB2 levels may be detected, for example, using an anti-ErbB2 antibody. An increase in ErbB2 activity may be detected by increased phosphorylation of ErbB2, activation of the MAPK pathway, activation of the p38-TSP-1 pathway, activation of the PI3K pathway, inhibition of CDC2, and combinations thereof.

Another aspect of the invention provides a method for inhibiting proliferation of a cancer cell, expressing ErbB2, in a subject in need thereof, the method comprising the step of administering to said subject a targed binding agent and/or an anti-ErbB2 antibody or antigen-binding portion thereof, wherein said targed binding agent or antibody or portion inhibits ErbB2. Another aspect provides a method for inhibiting an ErbB2 activity in a cell expressing ErbB2, comprising contacting the cell with a targed binding agent, an anti-ErbB2 antibody or antigen-binding portion thereof, wherein the ErbB2 activity in the cell is selected from the group consisting of (a) phosphorylation of ErbB2; (b) activation of the MAPK pathway; (c) activation of the p38-TSP-1 pathway; (d) activation of the PI3K pathway; (e) inhibition of CDC2; and (f) combinations thereof. In another embodiment, the cell is in a subject.

The targed binding agent and/or the antibody may be administered once, but more preferably is administered multiple times. The targed binding agent and/or the antibody may be administered from three times daily to once every six months or longer. The administering may be on a schedule such as three times daily, twice daily, once daily, once every two days, once every three days, once weekly, once every two weeks, once every month, once every two months, once every three months and once every six months. The targed binding agent and/or antibody may also be administered continuously via a minipump. The targed binding agent and/or antibody may be administered via an oral, mucosal, buccal, intranasal, inhalable, intravenous, subcutaneous, intramuscular, intraperitoneal, intraocular, intraspinal, parenteral, intramucosal or topical route. The targed binding agent and/or antibody may be adminstered locally or systemically.

The therapeutic compositions comprising a targed binding agent and/or a anti-ErbB2 antibodies may be administered to the subject, for example, orally, nasally, vaginally, buccally, rectally, via the eye, or via the pulmonary route, in a variety of pharmaceutically acceptable dosing forms, which will be familiar to those skilled in the art.

For example, the anti-ErbB2 antibodies may be administered via the nasal route using a nasal insufflator device. Example of these are already employed for commercial powder systems intended for nasal application (e.g. Fisons Lomudal System). Details of other devices can be found in the pharmaceutical literature (see for example Bell, A. Intranasal Delivery devices, in Drug Delivery Devices Fundamentals and Applications, Tyle P. (ed), Dekker, New York, 1988).

The anti-ErbB2 antibodies can be administered to the vagina in a freeze dried powder formulation. Anti-ErbB2 antibodies may be administered in a vaginal applicator and once in the vagina, the formulation comprising the anti-ErbB2 antibodies are released by pressing a syringe-type piston or similar release mechanism on the applicator. Alternatively, the anti-ErbB2 antibodies may be formulated as a powder using a powder device, formulated into a vagina suppository or pessary or vaginal tablet or vaginal gel.

The anti-ErbB2 antibodies can also be administered to the eye in a gel formulation. For example, before administration, a formulation containing the anti-ErbB2 antibodies may be conveniently contained in a two compartment unit dose container, one compartment containing a freeze-dried anti-ErbB2 antibody preparation and the other compartment containing normal saline. Prior to application, the two compartments are mixed and a gel is formed, which is then administered to the eye.

Other delivery routes for the anti-ErbB2 antibodies include via the pulmonary route using a powder inhaler or metered dose inhaler, via the buccal route formulated into a tablet or a buccal patch, via the rectal route formulated into suppositories; and via the oral route in the form of a tablet, a capsule or a pellet (which compositions may administer agent via the stomach, the small intestine or the colon), all of which may be formulated in accordance with techniques which are well known to those skilled in the art.

The antibody will generally be administered as part of a pharmaceutical composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art.

Co-administration of the antibody with an additional therapeutic agent (combination therapy) encompasses administering a pharmaceutical composition comprising the anti-ErbB2 antibody and the additional therapeutic agent as well as administering two or more separate pharmaceutical compositions, one comprising the anti-ErbB2 antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent, for example after a subject has failed therapy with the additional agent. Similarly, administration of the anti-ErbB2 antibody may be administered prior to or subsequent to other therapy, such as immunotherapy.

The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intraocular, intraspinal, intraperitoneal, intramuscular, parenteral, intratumor or topical route.

In a still further embodiment, the anti-ErbB2 antibody is labeled with a radiolabel, an immunotoxin or a toxin, or is a fusion protein comprising a toxic peptide. The anti-ErbB2 antibody or anti-ErbB2 antibody fusion protein directs the radiolabel, immunotoxin, toxin or toxic peptide to the ErbB2-expressing cell. In another embodiment, the radiolabel, immunotoxin, toxin or toxic peptide is internalized after the anti-ErbB2 antibody binds to the ErbB2 on the surface of the cell.

Gene Therapy

The nucleic acid molecules of the present invention can be administered to a subject in need thereof via gene therapy. The therapy may be either in vivo or ex vivo. In another embodiment, nucleic acid molecules encoding both a heavy chain and a light chain are administered to a subject. In a more preferred embodiment, the nucleic acid molecules are administered such that they are stably integrated into chromosomes of B cells because these cells are specialized for producing antibodies. In another embodiment, precursor B cells are transfected or infected ex vivo and re-transplanted into a subject in need thereof. In another embodiment, precursor B cells or other cells are infected in vivo using a virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated subject and using any immunoassay known in the art or discussed herein.

In another embodiment, the gene therapy method comprises the steps of administering an isolated nucleic acid molecule encoding the heavy chain or an antigen-binding portion thereof of an anti-ErbB2 antibody and expressing the nucleic acid molecule. In another embodiment, the gene therapy method comprises the steps of administering an isolated nucleic acid molecule encoding the light chain or an antigen-binding portion thereof of an anti-ErbB2 antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-ErbB2 antibody of the invention and expressing the nucleic acid molecules. The gene therapy method may also comprise the step of administering another therapeutic agent, such as a anti-cancer agent.

In order that this invention may be better understood, the following examples are set forth. These examples are for purposes of illustration only and are not to be construed as limiting the scope of the invention in any manner.

Example 1

Immunization and Titering

Immunization

Recombinant human ErbB2-ECD/Fcγ1 fusion protein containing the extracellular domain of human ErbB2 and the Fc region of human IgG1 was obtained from R&D Systems, Inc. (Minneapolis, Minn. catalog #1129-ER/CF) for use as immunogen. Monoclonal antibodies against ErbB2 were developed by sequentially immunizing XenoMouse® mice (XenoMouse strain XM3B-3, Abgenix, Inc. Fremont, Calif.) via footpad route injections. The first injection was with 10 μg recombinant human ErbB2-ECD/Fcγ1 in Titermax Gold (Sigma, catalog #T2684, lot #K1599) per mouse. The following 10 boosts were with 10 μg recombinant human ErbB2-ECD/Fcγ1 in 15 μl of qCpG (ImmunEasy Mouse Adjuvant, catalog #303101; Qiagen), admixed with 5 μl of Adju-Phos (aluminum phosphate gel, Catalog #1452-250, HCl Biosector) per mouse. The total volume of each injection was 50 μl per mouse, 25 μl per footpad. The mice were immunized twice weekly for 5 weeks and fusion was performed on day 39.

Selection of Animals for Harvest by Titer

The immunized XenoMouse mice were bled after the 8th boost, and anti-ErbB2 antibody titers in the sera were determined by FACS (Fluorescence-Activated Cell Sorter) analysis.

For this purpose, a human ErbB2 expression vector was constructed and mouse pre-B B300.19 cells were transfected to express human ErbB2 protein. Human ErbB2 cDNA was derived by RT-PCR from human epidermoid carcinoma A431 cells (ATCC, catalog #CRL-1555) and cloned into the pCR3.1 expression vector (invitrogen, catalog #K3000) through HindIII and NotI endonuclease restriction cleavage sites. The expression vector contained an insert of 3768 bp encoding the full length human ErbB2. The above plasmid was transfected into B300.19 cells using electroporation method. Stable B300.19 clones expressing hErbB2 protein were selected in the presence of puromycin (2.5 ug/ml) and then screened by FACS with a chimeric anti-hErbB2 antibody (referred to herein as 2C4, made as detailed in Cancer Immunol. Immunotherapy (2006) 55:717-727 entitled "Humanization of a recombinant monoclonal antibody to produce a therapeutic HER dimerization inhibitor, pertuzumab") followed by goat anti-mouse IgG PE (Caltag, catalog #M30004-4). B300.19/hErbB2 clone #44, giving the highest Geomean in FACS, was selected for sera titer determination.

Sera from immunized and bled mice were titrated in FACS buffer (PBS with 2% FBS) at 1:50, 1:250 or 1:1250 dilutions. B300.19/hErbB2 clone #44 cells (positive cells) and B300.19 parental cells (negative cells) were incubated with serially diluted sera for 1 hour, and then with Cy5-conjugated Goat anti-human IgG (Jackson ImmunoResearch Labs/JIR, catalog #109-176-098) for another 30 minutes. Anti-ErbB2 mAb 2C4 was used as a positive control while an anti-KLH G1 antibody generated in house (Gmix) was used as a G1 isotype control. After extensive washing, cells were re-suspended in FACS buffer and analyzed on a BD FACS instrument. Geomean of each sample was determined after data analysis and is shown in Table 2 below. The ratio of Geomean on ErbB2 positive cells over Geomean on ErbB2 negative cells correlates with the specific binding ability to ErbB2. The negative controls, including G1 isotype control anti-KLH Gmix, secondary control antibodies goat anti-mouse IgG Cy5 (JIR, catalog #115-176-071) and goat anti-human IgG PE alone, gave a Geomean ratio of below 1. While the positive control mAb 2C4 and sera from all 10 immunized mice gave ratios between 2.98 and 7.55, therefore all mice developed humoral immune response to human ErbB2.

TABLE 2

Serum titers: 10 mice (XM3B-3 strain)

| | | GeoMeans | | |
|---|---|---|---|---|
| Samples Mouse ID | Assay dilution | pos cells GeoMean | neg cells GeoMean | Geomean Ratio |
| 5152-1 | 1:50 | 324 | 62.2 | 5.21 |
| | 1:250 | 251 | 45.1 | 5.57 |
| | 1:1250 | 177 | 26.5 | 6.68 |

TABLE 2-continued

Serum titers: 10 mice (XM3B-3 strain)

| Samples Mouse ID | Assay dilution | GeoMeans | | |
|---|---|---|---|---|
| | | pos cells GeoMean | neg cells GeoMean | Geomean Ratio |
| 5152-2 | 1:50 | 308 | 75 | 4.11 |
| | 1:250 | 209 | 39.9 | 5.24 |
| | 1:1250 | 146 | 23.4 | 6.24 |
| 5152-3 | 1:50 | 304 | 85.3 | 3.56 |
| | 1:250 | 199 | 40.1 | 4.96 |
| | 1:1250 | 157 | 21.1 | 7.44 |
| 5152-4 | 1:50 | 331 | 111 | 2.98 |
| | 1:250 | 227 | 42.8 | 5.30 |
| | 1:1250 | 166 | 22 | 7.55 |
| 5152-5 | 1:50 | 196 | 55.1 | 3.56 |
| | 1:250 | 142 | 26.4 | 5.38 |
| | 1:1250 | 91.7 | 16.2 | 5.66 |
| 5152-6 | 1:50 | 214 | 66.9 | 3.20 |
| | 1:250 | 129 | 33.1 | 3.90 |
| | 1:1250 | 92.4 | 17.5 | 5.28 |
| 5152-7 | 1:50 | 278 | 88.1 | 3.16 |
| | 1:250 | 157 | 38.1 | 4.12 |
| | 1:1250 | 122 | 20.5 | 5.95 |
| 5152-8 | 1:50 | 240 | 58.3 | 4.12 |
| | 1:250 | 168 | 27.2 | 6.18 |
| | 1:1250 | 94.3 | 16 | 5.89 |
| 5152-9 | 1:50 | 208 | 46.2 | 4.50 |
| | 1:250 | 137 | 24.1 | 5.68 |
| | 1:1250 | 89.9 | 15.9 | 5.65 |
| 5152-10 | 1:50 | 256 | 82.9 | 3.09 |
| | 1:250 | 157 | 40.5 | 3.88 |
| | 1:1250 | 131 | 22.7 | 5.77 |

Example 2

Recovery of Lymphocytes, B-Cell Isolations, Fusions and Generation of Hybridomas Lymph nodes (LN) were harvested from the immunized mice and processed into 3 ml sterile FASC buffer (PBS, 2% FBS). The LN cells were filtered through a 40 µm cell filter, spun down at 400 g for 3 minutes and resuspended in 3 ml fresh FACS buffer. The cells were counted, and then biotinylated antibodies against CD90 (Pharmingen, catalog #553002), CD4 (Pharmingen, catalog #553728), CD8 (Pharmingen, catalog #553029) and IgM (Pharmingen, catalog #555781) were added. The cells and the above antibodies were mixed gently and incubated for 10 minutes on ice. Cells were spun down again and washed once with FACS buffer. SA Dynal beads (M-280) were added to cells at a ratio of 4:1 beads to target cells, and incubated at room temperature for 12 minutes with rotating. The cells/beads in 15 ml tubes were placed in the magnetic field of the Dynal magnet for 2 minutes. The supernatant containing the IgM-fraction was transferred to a fresh tube and the magnet step was repeated one more time. The cell supernatant was transferred to a final tube and IgM-cells were counted and aliquoted for fusion.

The fusion was performed by mixing washed enriched B cells from above and non-secretory myeloma P3X63Ag8.653 cells purchased from ATCC (catalog #CRL 1580) (Kearney et al, J. Immunol. 123, 1979, 1548-1550) at a ratio of 1:1. The cell mixture was gently pelleted by centrifugation at 800×g. After complete removal of the supernatant, the cells were treated with 2-4 ml of Pronase solution (CalBiochem, cat. #53702; 0.5 mg/ml in PBS) for no more than 2 minutes. Then 3-5 ml of FBS was added to stop the enzyme activity and the suspension was adjusted to 40 ml total volume using electro cell fusion solution (ECFS: 0.3M Sucrose, 0.1 mM Magnesium Acetate, 0.1 mM Calcium Acetate, all from Sigma). The supernatant was removed after centrifugation and the cells were resuspended in 40 ml ECFS. This wash step was repeated and the cells again were resuspended in ECFS to a concentration of $2 \times 10^6$ cells/ml.

Electro-cell fusion was performed using a fusion generator (model ECM2001, Genetronic, Inc., San Diego, Calif.), according to the standard instrument settings. After ECF, the cell suspensions were carefully removed from the fusion chamber and transferred into a sterile tube containing the same volume of Hybridoma Culture Medium containing DMEM (JRH Biosciences), 15% FBS (Hyclone), supplemented with L-glutamine, Penicillin/Streptomycin, OPI (oxaloacetate, pyruvate, bovine insulin) (all from Sigma) and IL-6 (Boehringer Mannheim). The cells were incubated for 15-30 minutes at 37° C., and then centrifuged at 400×g (1000 rpm) for five minutes. The cells were gently resuspended in Hybridoma Selection Medium (Hybridoma Culture Medium supplemented with 0.5×HA (Sigma, cat. #A9666)), based on a final plating of $2 \times 10^5$ B cells total per 96-well plate and 200 µl per well. The cells were mixed gently and pipetted into 96-well plates and allowed to grow. On day 7 or 10, one-half the medium was removed, and the cells were re-fed with Hybridoma Selection Medium.

Example 3

Screening of Antibodies by FMAT/FACS

After 14 days of culture, hybridoma supernatants were screened for ErbB2-specific antibodies by FMAT (Fluorometric Microvolume Assay Technology). Briefly, 4275 cells of B300.19/hErbB2 (positive cells) or B300.19 (ErbB2-negative cells) were mixed with 400 ng/ml Cy5 Goat anti-human IgG (JIR, catalog #109-176-098) in 15 µl of FACS buffer and then incubated with 15 µl of hybridoma supernatants for 3 hours at room temperature. Positive control antibody was anti-hErbB2 (2C4), which was detected with Cy5 goat anti-mouse IgG gamma (JIR, catalog #115-176-071) or Goat anti-mouse IgG-Biot (Southern Biotechnology/SB catalog #1030-08, 400 ng/ml) in combination with SA-Cy5 (JIR catalog #016-170-084, 350 ng/ml). An anti-KLH G1 antibody (Gmix, in-house) was used as an isotype control. The plates were read on FMAT 8100 HTS systems from Applied Biosystems. Both fluorescence signals and counts were determined after data analysis and 362 positive hybridomas that showed binding to ErbB2-positive cells but not to negative cells were identified.

The 362 positive supernatants in the FMAT screening were further screened by FACS in two sets, one for hIgG heavy chain detection and the other for human Ig kappa light chain detection, to demonstrate fully human composition for both Ig gamma and Ig kappa chains. $2.5 \times 10^5$ B300.19/hErbB2 cells or B300.19 parental cells were incubated with hybridoma supernatants diluted at 1:2 in FACS buffer for 1 hour at 4° C. and then washed with PBS. Cells were then incubated with goat anti-human gamma Cy5 for 1 hour at 4° C. for Ig gamma detection, or with goat anti-human kappa PE (SB catalog #2063-09) for 1 hour at 4° C. for Ig kappa detection. After washing, cells were fixed in 1% paraformaldehyde/PBS before FACS analysis. Pooled sera at 1:50 dilution was used as a positive control while 1:10 diluted Gmix (anti-KLH IgG) was used as a negative isotype control in the assay. The ratio of the Geomean values between positive and negative cells was tabulated and hybridomas giving ratios over 1.95 were considered hits. A total of 152 fully human anti-hErbB2 IgG/kappa antibodies were confirmed in this screen.

Example 4

Inhibition of Heregulin-β Induced ERBB2 Phosphorylation in MCF7 Cells

ErbB2 is tyrosine phosphorylated upon activation through dimerization with other ErbB family members, such as ErbB3. Heregulin-β binding to ErbB3 can induce ErbB2 tyrosine phosphorylation in human breast adenocarcinoma MCF7 cells, which express both ErbB2 and ErbB3. To identify antibodies that block ErbB2 activation, we screened 152 human ErbB2-binding antibodies in cell-based ErbB2 phosphorylation assays.

MCF7 cells were seeded at 25,000 cells/well in 96 well plates and cultured in full growth media (10% FCS) overnight. The next day, cell culture plates were washed once with PBS and culture media was replaced with phenol red-free and serum-free media. Cells were serum-starved overnight, and then incubated with 25 µl of hybridoma supernatants mixed with 25 µl phenol red-free medium for 1 hour before being treated with 10 nM Heregulin-β for 10 minutes. Alternatively, cells were not serum-starved but incubated with hybridoma supernatants overnight (~24 hrs) before Heregulin-β treatment.

To prepare cell lysates, cells were washed in ice-cold PBS twice and incubated with 100 µl/well of lysis buffer (50 mM Tris-HCl p117.7, 1% Trixton X-100, 10% glycerol, 100 mM NaCl, 2.5 mM EDTA, 10 mM NaF, 40 ug/ml PMSF, 1 uM Pepstatin, 0.5 ug/ml Leupeptin, 10 ug/ml Soybean Trypsin inhibitor, 0.2 mM NaVO4, 1 mM NaMoO4, 5 mM b-glycerophosphate) at 4° C. for 30 minutes. Phosphor-ErbB2 level was measured using a human phosphor-ErbB2 ELISA kit from R&D systems (human Phospho-ErbB2 DuoSet IC, Catalog #DYC1768), according to the protocol provided. Percentage of inhibition was calculated based on the level of pErbB2 in un-stimulated cells and Heregulin-stimulated cells in the absence of antibodies.

FIG. 1 illustrates the correlation of the neutralizing activities of the 152 antibodies tested when they were pre-incubated with MCF7 cells for 1 hr vs. 24 hr overnight. 51 out of 152 antibodies gave more than 30% inhibition when cells were pre-incubated with supernatants for 1 hour. These antibodies likely inhibit ErbB2 phosphorylation by blocking dimerization of ErbB2 with ErbB3. Significantly more antibodies demonstrated more than 30% inhibition when cells were pre-incubated with hybridoma supernatants overnight. Some of these may do so by other mechanism such as inducing ErbB2 down-regulation.

Example 5

Determination of Cross-Reactivity to CYNO ERBB2

To determine the species cross-reactivity of these antibodies to non-human Primate cynomolgus ErbB2, CHO-K1 cells expressing cynomolgus ErbB2 were generated. Briefly, the cyno ErbB2 cDNA was derived from cynomolgus ovary tissues and cloned into pCR3.1 expression vector through HindIII and XbaI restriction endonuclease sites. The expression vector, cyno-ErbB2 (FL)/pCr3.1 containing an insert of 3767 bps, was transfected into CHO-k1 cell using Lipofectamine 2000 (Invitrogen, catalog #11668) according to the protocol provided. Stable clones of CHO-K1 expressing cyno-ErbB2 were selected in the presence of G418 at 1 mg/ml. The expression was confirmed by FACS using mouse anti-human c-ErbB2/c-neu (Ab-2) (Oncogene, catalog #OP14) and goat anti-mouse IgG-PE (Caltag, catalog #M30004-4).

CHO-K1/cyno E4rbB2 clone #4 was used to measure the cross-reactivity of the human ErbB2-binding antibodies. 200,000 cells of CHO-K1/cyno ErbB2 clone #4 or parental CHO-K1 were incubated with 1:2 diluted hybridoma supernatants or 2 µg/ml positive control antibody Ab-2 (Oncogene, catalog #OP14) for 1 hour at 4° C. Cells were washed once with PBS, and then incubated with secondary detection antibody 5 µg/ml of goat anti-human IgG Cy5 or goat anti-mouse IgG Cy5 for 1 hour at 4° C. Cells were washed three times with PBS, fixed in 1% paraformaldehyde/PBS and then analyzed by FACS. For each staining, the ratio of Geomean values between positive and negative cells was tabulated and a ratio above 1.95 was considered positive. Eight antibodies were found not to cross-react with cyno ErbB2 and were excluded from the later analyses.

Example 6

High Antigen and Limited Antigen ELISAs 113 anti-ErbB2 antibodies that demonstrated cyno ErbB2 cross-reactivity, and also showed ≥30% inhibition of ErbB2 phosphorylation when incubated with cells for either 1 hr or overnight, were further characterized by high antigen (HA) and limited antigen (LA) ELISAs.

HA ELISA is performed with high concentrations of antigen coated on plate, and is a concentration-dependent reaction; while LA ELISA is conducted with limited amount of antigen coated on plate and thus is an affinity dependent reaction. Relative affinity ranking of antibodies can be achieved from HA/LA analysis.

Since the recombinant human ErbB2 ECD-Fcγ1 fusion protein cannot be used for this purpose, a human ErbB2 ECD-myc/His fusion protein was generated in-house. The human ErbB2/ECD cDNA was derived from A431 cells and cloned into pSecTag2Hygro expression vector (Invitrogen, catalog #V910-20) through the NheI and XhoI restriction endonuclease cleavage sites. The expression vector, huErbB2 (ECD)/pSecTag2BHygro, contained an insert size of 1956 bp for the ErbB2 (ECD) only and 2034 bp for the hErbB2 (ECD) plus c-myc/His tag. The plasmid was transiently transfected into 293T suspension cells using 293fectin (Invitrogen catalog #12347-019). The cells were treated with Sodium butyrate one day post transfection to boost expression levels. 4 Days after transfection, supernatant was tested for ErbB2 (ECD) expression before purification. For ELISA detection, 1 µg/ml goat anti-ErbB2 (R&D systems, catalog #AF1129) was used to coat the plates, 1 µg/ml of mouse anti-ErbB2 (R&D systems, catalog #MAB 1129) was the primary detection antibody and the secondary antibody was goat anti-mouse IgG-HRP (Caltag, catalog #M30107). Supernatant was harvested and concentrated 5 fold and then dialyzed into dialysis buffer (50 mM NaH2PO4, pH 8, 200 mM NaCl) overnight. Imidazole was added to the supernatant to a final concentration of 5 mM and the supernatant was incubated with $\frac{1}{100}^{th}$ volume of Ni-NTA superflow resin mixture (Qiagen, Cat#30430) for 3 hours at RT. The resin was washed with a buffer containing 50 mM NaHPO4, 300 mM NaCl and 20 mM Imidazole, and then with the elution buffer containing 250 mM Imidazole, 50 mM NaHPO4 and 300 mM NaCl. The purified protein was finally dialyzed into PBS to preserve activity. The purified protein huErbB2 (ECD)/c-myc-His has 655 AAs, with a theoretical MW of 72.2 kDa, runs around 100 kDa on a 4-20% Tris-Glycine SDS-PAGE gel. The protein identity was confirmed by western blot using a mouse monoclonal anti-ErbB2 (R&D systems, Cat#MAB1129) followed by a secondary goat anti-mouse IgG-HRP (Caltag, cat #M30107).

For HA, 10 μg/ml human ErbB2 ECD-mycalis in PBS was coated to ELISA plates overnight at 4° C. For LA, 100, 500, 250, 125, 62, and 31 ng/ml of human ErbB2 ECD-myc/His was coated. Antigen-coated plates were washed three times, blocked with 1% non-fat skim milk/PBS for at least 30 minutes at room temperature, and then washed again three times. Each hybridoma line sample was titrated in 1% non-fat skim-milk/PBS 1:3 for 7 points starting from a 1:25 dilution. Serially diluted hybridoma samples or controls (Herceptin®) were transferred to HA-coated plates and 1:25 diluted hybridoma samples were transferred to LA-coated plates. Samples were incubated on plates at room temperature overnight for 18.5 hours. The next day, plates were washed three times and incubated with 50 μl of 400 ng/ml immunopure Goat anti-human IgG (Fc)-HRP (Pierce catalog #31416) for 1 hour at room temperature. Then, the plates were extensively washed and pat dried on paper towel to remove residual HRP in wells. HRP substrate TMB (enhanced K-blue TMB, Neogen catalog #308177) was added to each well and incubated for 30 min. The reaction was stopped by addition of 1N HCl. Optical density at 450 nm was read on a microplate reader (Titerteck Multiskan Ascent).

Figure 2:
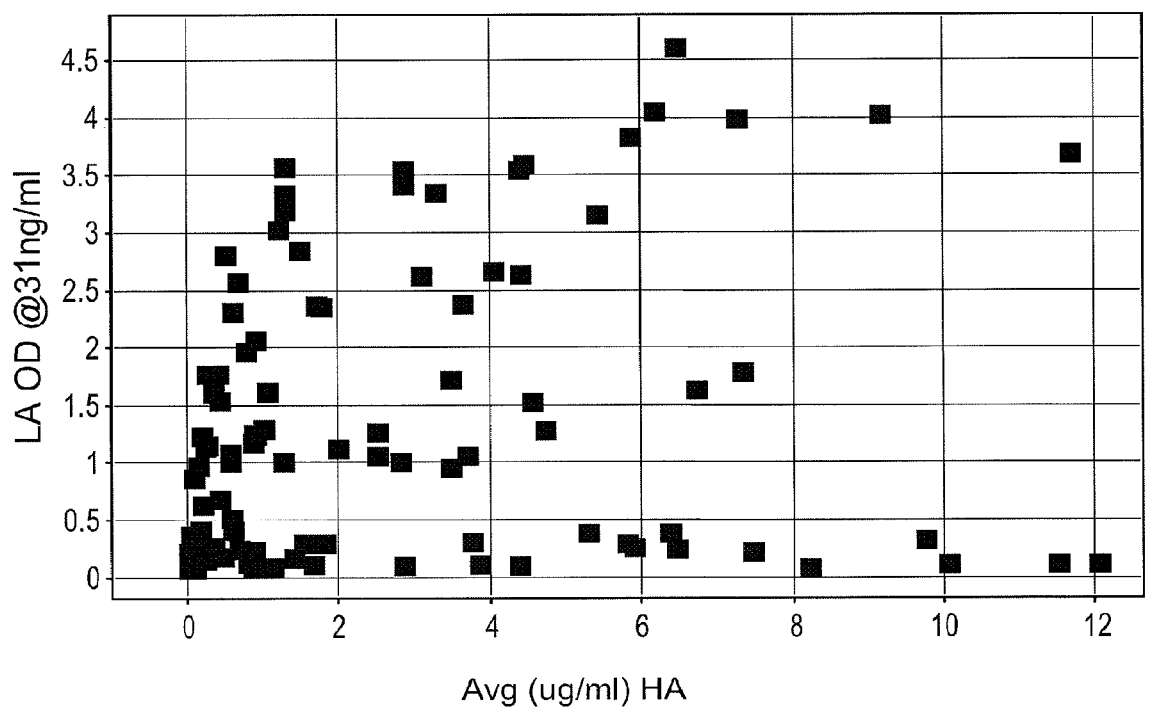
FIG. 2 is a data plot of LA/HA ELISA analysis. The Y axis indicates the binding signal in OD value when 31 ng/ml of hErbB2(ECD)/cMyc-His was coated on ELISA plate. The X axis indicates the concentration of ErbB2-specific antibodies in hybridoma supernatants derived from HA ELISA when 10 µg/ml of ErbB2(ECD)/cMyc-His was coated on the ELISA plate.

The concentration of ErbB2-specific antibodies in hybridoma supernatants was derived from a standard curve generated with known concentrations of Herceptin® in HA ELISA. LA OD signal at 31 ng/ml antigen was plotted against antibody concentration from HA for each hybridoma sample, as shown in FIG. 2. The antibodies in the upper left corner have relatively high affinities compared to the antibodies in the lower right corner in this plot.

Example 7

Hybridoma Cloning

Based on the data from cyno cross-reactivity testing, inhibition of ErbB2 phosphorylation assays and LA/HA ELISAs, 31 hybridoma lines were selected for cloning. Their activities are summarized in Table 3.

TABLE 3

Preliminary characterization data of hyrbidoma lines selected for cloning

| LINE ID | 1 hr pTyr inhibition % | 24 hr pTyr inhibition % | Cyno Cross-reactivity | HA Avg (ug/ml) | LA at 31 ng/ml |
|---|---|---|---|---|---|
| 1*14 | 103 | 100 | YES | 7.27 | 3.99 |
| 1*15 | 86 | 100 | YES | 0.61 | 2.31 |
| 1*18 | 85 | 96 | YES | 1.22 | 3.03 |
| 1*20 | 91 | 96 | YES | 1.5 | 2.84 |
| 1*22 | 84 | 95 | YES | 1.06 | 1.61 |
| 1*37 | 96 | 96 | YES | 1.3 | 3.33 |
| 1*39 | 82 | 99 | YES | 0.68 | 2.57 |
| 1*62 | 82 | 98 | YES | 0.51 | 2.8 |
| 1*96 | 97 | 99 | YES | 6.48 | 4.6 |
| 1*99 | 97 | 99 | YES | 6.18 | 4.05 |
| 1*100 | 95 | 95 | YES | 2.85 | 3.54 |
| 1*108 | 90 | 100 | YES | 4.41 | 2.64 |
| 1*124 | 94 | 97 | YES | 2.86 | 3.42 |
| 1*128 | 96 | 98 | YES | 5.86 | 3.83 |
| 1*140 | 97 | 97 | YES | 4.39 | 3.54 |
| 1*148 | 96 | 97 | YES | 3.29 | 3.35 |
| 1*149 | 83 | 89 | YES | 0.43 | 1.54 |
| 1*19 | 73 | 97 | YES | 0.4 | 1.77 |
| 1*24 | 77 | 99 | YES | 1.77 | 2.35 |
| 1*33 | 73 | 101 | YES | 0.9 | 2.07 |
| 1*41 | 26 | 86 | YES | 1.3 | 3.2 |
| 1*43 | 43 | 82 | YES | 1.3 | 3.57 |
| 1*44 | 78 | 98 | YES | 3.64 | 2.38 |
| 1*69 | 57 | 72 | YES | 0.34 | 1.6 |
| 1*71 | 27 | 65 | YES | 3.1 | 2.62 |
| 1*74 | 66 | 90 | YES | 0.20 | 1.22 |
| 1*79 | 71 | 93 | YES | 0.26 | 1.77 |
| 1*95 | 58 | 95 | YES | 0.23 | 1.14 |
| 1*104 | 21 | 73 | YES | 1.7 | 2.36 |
| 1*107 | 57 | 82 | YES | 0.25 | 1.15 |
| 1*111 | 78 | 98 | YES | 0.77 | 1.97 |

Cells in each hybridoma line were sorted on FACS Aria (BD) into 96 well plates at 1 cell/well and cultured for about 2 weeks. Supernatants from single clones were screened for ErbB2-binding activity by FMAT on BT474 cells which express high level of ErbB2, and also for human Ig gamma and kappa chain composition, as well as presence of human IgM and mouse IgM by ELISA.

For FMAT, 6000 BT474 cells (ATCC) in 40 μl FACS buffer in 384 well FMAT plates were incubated with 15 μl of supernatants for 2 hour at room temperature and then with 10 μl of 4.5 μg/ml goat-anti-human IgG Cy5 for 6 hours at room temperature before reading on FMAT machine 8200. Both fluorescence and counts data were analyzed. Herceptin® was used as a positive control in the screen.

For human antibody chain composition analysis, medium binding 96 well plates (Coastar 3368) were coated with 2 μg/ml Goat anti-human IgG Fc in PBS overnight at 4° C., and blocked with 1% milk/PBS for 30 minutes at room temperature, Supernatants were diluted 1:5 in 1% milk/PBS and added to two coated ELISA plates, and incubated at room temperature for 1 hour. Biotinylated goat anti-human Kappa (Vector catalog #BA3060) at 250 ng/ml in 1% milk/PBS or biotinylated goat anti-human Lambda (Southern Biotech catalog #2070-08) at 250 ng/ml in 1% milk/PBS were then added and incubated for 1 hour at room temperature followed by incubation with Streptavidin Peroxidase conjugate at 1 μg/ml in 1% milk/PBS for 1 hour at room temperature. Plates were extensively washed between incubation steps. 50 μl of Peroxidase substrate TMB was added and incubated for 30 minutes at room temperature, and the enzyme reaction was quenched with 50 μl of 1M HCL. Optical density was read at 450 nm on a microplate reader (Titerteck Multiskan Ascent).

We confirmed the absense of human IgM as follows. Medium binding 96 well plates (Coastar 3368) were coated with 1 μg/ml Goat anti-human IgM in PBS overnight at 4° C., and blocked with 1% milk/PBS for 30 minutes at room temperature. Supernatants were diluted 1:5 in 1% milk/PBS and added to the coated ELISA plates, and incubated at room temperature for 1 hour. Donkey anti-human 1gM POD (Accurate Chemical catalog #JNH035043) at 666 ng/ml in 1% milk/PBS was then added and incubated for 1 hour at room temperature. Plates were developed by addition of POD substrate as described above.

We confirmed the absense of human IgM as follows. Medium binding 96 well plates were coated with 1 μg/ml Goat anti-mouse lambda (Southern Biotech 1060-01) in PBS overnight at 4° C., and blocked with 1% milk/PBS for 30 minutes at room temperature. Supernatants were diluted 1:5 in 1% milk/PBS and added to the coated ELISA plates, and incubated at room temperature for 1 hour. Goat anti-human IgG (Fc) POD (Pierce catalog #31413) at 400 ng/ml in 1% milk/PBS was then added and incubated for 1 hour at room temperature. Plates were developed by addition of POD substrate as described before.

In the ELISAs described above, signal from wells with no primary antibodies was used as background and samples giving signals that were 3 times above the background were considered positive.

Monoclonal antibodies that demonstrated native binding to ErbB2 by FMAT and that were positive for human gamma chain and kappa chain by ELISAs were derived from 20 hybridoma lines after cloning. Three subclones from each parental line were sequenced. Unless otherwise indicated all three subclones were identical. For example, subclones 1.14.1, 1.14.2, and 1.14.3 of parent clone 1.14 all had the same sequence and are referred to interchangably by the two-number parent name or the three-number subclone name. Eleven unique monoclonal antibodies were identified and further characterized in cell-based functional assays.

Example 8

Structural Analysis of ErbB2 Monoclonal Antibodies

The heavy chain and the light chain variable domains of the antibodies were sequenced. The complete sequence information for the anti-ErbB2 antibodies is provided in the Sequence Listing with nucleotide and amino acid sequences for each gamma and kappa chain combination. The variable (V) regions of immunoglobulin chains are encoded by multiple germ line DNA segments, which are joined into functional variable regions ($V_H DJ_H$ or $V_L A$) during B-cell ontogeny. The variable heavy sequences were analyzed to determine the VH family, the D-region sequence and the J-region sequence. The sequences were then translated to determine the primary amino acid sequence and compared to the germline VH, D and J-region sequences to assess somatic hypermutations. The heavy variable light chain sequences were similarly analyzed.

Table 4 and Table 4(a) are tables comparing the antibody heavy chain regions to their cognate germ line heavy chain region. Table 5 is a table comparing the antibody kappa light chain regions to their cognate germ line light chain region. The difference between Tables 4 and 4(a) is the definition used to define the heavy chain CDR1s. The heavy chain CDR1s disclosed in Table 4(a) are of the Kabat definition. Alternatively, the CDR can be defined using an alternative definition so as to include the last four residues of the FR1 sequence as shown in Table 4.

Analysis of 20 individual antibodies specific to ErbB2 indicated that some of them are identical and only 11 unique monoclonal antibodies were resulted from cloning 8 of the 11 antibodies are very similar in sequence and were derived from the same germline VH and VK genes.

It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of a non-limiting example, Table 4 shows the heavy chain sequence of 1.20.1 differs from the corresponding germline sequence at amino acid 33 by a T to an S in the CDR1 region. Thus, the amino acid or nucleotide sequence encoding the heavy chain of 1.20.1 can be modified to change the T to an S to yield the germline sequence at the site of the mutation. In another example, the heavy chain sequence of 1.140.1 differs from the corresponding germline sequence at amino acid 42 by an R to a G in the FR2 region. Thus, the amino acid or nucleotide sequence encoding the heavy chain of 1.140.1 can be modified to change the R to a G to yield the germline sequence at the site of the mutation.

By way of another non-limiting example, Table 5 shows that the light chain sequence of 1.140.1 differs from the corresponding germline sequence by a T to N mutation (mutation 1) in the FR1 region, by a F to L, F to Y and C to Y (mutations 2, 3, and 4) in the CDR1 region, by a R to K and N to K in the FR2 region (mutations 5 and 6) and by a F to Y, G to S, and S to T in the CDR3 region. Thus, the amino acid or nucleotide sequence encoding the light chain of 1.140.1 can be modified to change mutation 1 to yield the germline sequence at the site of mutation 1. Further, the amino acid or nucleotide sequence encoding the light chain of 1.140.1 can be modified to change mutation 2 to yield the germline sequence at the site of mutation 2. Still further, the amino acid or nucleotide sequence encoding the light chain of 1.140.1 can be modified to change mutation 3 to yield the germline sequence at the site of mutation 3. Still further again, the amino acid or nucleotide sequence encoding the light chain of 1.140.1 can be modified to change mutation 1, mutation 2, mutation 3, mutation 4, mutation 5 and mutation 6 to yield the germline sequence at these. Table 6 below illustrates the position of such variations from the germline for 1.140. Each row represents a unique combination of germline and non-germline residues at the position indicated by bold type. Table 6 also applies to antibody 1.39 as the light chain analysis for antibody 1.39 is identical to 1.140 with respect to germline mutations. Moreover, the light chain analysis for antibody 1.96 is identical to 1.140 with respect to germline mutations except that the antibody 1.96 has a difference between the antibody sequence and the germline sequence in FR4. In this example, the L of the antibody sequence can be mutated back to the germline sequence of an F, and this mutation can be combined with any of the combinations shown in Table 6.

In one embodiment, the invention features modifying one or more of the amino acids in the CDR regions, i.e., CDR1, CDR2 and/or CDR3. In one example, the CDR3 of the heavy, light or both chains of an antibody described herein is modified. Typically, the amino acid is substituted with an amino acid having a similar side chain (a conservative amino acid substitution), back to germline, or can be substituted with any appropriate amino acid such as an alanine or a leucine. In one embodiment, the 1.24.3 CDR3, QQYSSPFT (SEQ ID NO: 48) can be modified at one or more amino acids back to for example by mutating the CDR3 sequence to QQYYSPFT (SEQ ID NO:49).

In another embodiment, the invention features modifying the antibody to remove unpaired cysteines. Examples of unpaired cysteines appear in antibody 1.39.1 at amino acid 38, in antibody 1.96.1 at amino acid 38, and for antibody 1.140.1 at amino acid 38. These cysteines can be mutated back to germline, for example, mutating the C to Y or by mutating the C to any appropriate amino acid such as a serine.

TABLE 4

Heavy Chain Analysis

| Chain Name | SEQ ID NO: | V | D | J | FR1 | CDR1 | FR2 |
|---|---|---|---|---|---|---|---|
| | 54 | | Germline | | EVQLVESGGGLVK PGGSLRLSCAAS | GFTFSSYSMN | WVRQAPGKGLEWVS |
| 1.14.1 | 14 | VH3-21 | D5-24 | JH4B | EVQLVESGGGLVK PGGSLRLSCAAS | GFTFSSYSMN | WVRQAPGKGLEWVS |
| 1.18.1 | 26 | " | " | " | EVQLVESGGGLVK PGGSLRLSCAAS | GFTFSSYSMN | WVRQAPGKGLEWVS |
| 1.20.1 = 1.19 | 30 | " | " | " | EVQLVESGGGLVK PGGSLRLSCAAS | GFTFSSYTMN | WVRQAPGKGLEWVS |
| 1.24.3 = 1.22.2 = 1.71.1 | 38 | " | " | " | EVQLVESGGGLVK PGGSLRLSCAAS | GFTFSSYSMN | WVRQAPGKGLEWVS |
| 1.39.1 | 34 | " | " | " | EVQLVESGGGLVK PGGSLRLSCAAS | GFTFSSYSMN | WVRQAPGKGLEWVS |
| 1.96.2 = 1.99 = 1.104 = 1.107 = 1.128 | 22 | " | " | " | EVQLVESGGGLVK PGGSLRLSCAAS | GFTFSSYSMN | WVRQAPGKGLEWVS |
| 1.100.1 | 18 | " | " | " | EVQLVESGGGLVK PGGSLRLSCAAS | GFTFSSYSMN | WVRQAPGKGLEWVS |
| 1.140.1 = 1.124 = 1.148 | 6 | " | " | " | EVQLVESGGGLVK PGGSLRLSCAAS | GFTFSSYSMN | WVRQAPRKGLEWVS |
| | 57 | | Germline | | EVQLVESGGGLVQ PGGSLRLSCAAS | GFTFSSYWMS | WVRQAPGKGLEWVA |
| 1.43.1 = 1.41 = 1.22.1 | 10 | VH3-7 | D5-24 | JH6B | EVQLVESGGGLVQ PGGSLRLSCAAS | GFTFSSYWMH | WVRQTPGKLGEWVA |
| | 59 | | Germline | | QVQLQESGPGLVK PSQTLSLTCTVS | GGSISSGGYY WS | WIRQHPGKLEWIG |
| 1.44.1 | 2 | VH4-31 | D3-10 | JH6B | QVQLQESGPGLVK PSQTLSLTCTVS | GGSISSGGYY WS | WIRQHPGKLEWIG |
| | 56 | | germline | | EVQLVESGGGLVQ PGGSLRLSCAAS | GFTFSSYDMH | WVRQATGKGLEWVS |
| 1.71.2 = 1.71.3 | 42 | VH3-13 | D6-19 | JH6B | EVQLVESGGGLVQ PGGSLRLSCTAS | GFPFSSYDMH | WVRQATGKGLEWVS |

| Chain Name | SEQ ID NO: | CDR2 | FR3 | CDR3 | FR4 |
|---|---|---|---|---|---|
| | 54 | SISSSSSYIY YADSVKG | RFTISRDNAKNSL YLQMNSLRAEDTA VYYCAR | ##DGYNY #YFDY | WGQGTLVTVSS |
| 1.14.1 | 14 | SISSSSSYIY YADSVKG | RFTISRDNAKNSL YLQMNSLRAEDTA VYYCAR | GGDGYNY YYFDY | WGQGTLVTVSS |
| 1.18.1 | 26 | SISSSSSYIY YADSVKG | RFTISRDNAKNSL YLQMNSLSAEDTA VYSCAR | GGDGYNY YYFDY | WGQGTLVTVSS |
| 1.20.1 = 1.19 | 30 | SISSSSSYIY YADSVKG | RFTISRDNAKNSL YLAMNSLSAEDTA VYSCAR | GGDGYNY YYFDY | WGQGTLVTVSS |
| 1.24.3 = 1.22.2 = 1.71.1 | 38 | SISSSSSYIY YADSVKG | RFTISRDNAKNSL YLQMNSLRAEDTA VYYCAR | GGDGYNY YYFDY | WGQGTLVTVSS |

TABLE 4-continued

Heavy Chain Analysis

| | | | | | | |
|---|---|---|---|---|---|---|
| 1.39.1 | 34 | SISSSSSYIY YADSVKG | RFTISRDNAKNSL YLQMNSLRAEDTA VYYCAR | GGDGYNY YYFDY | WGQGTLVTVSS | |
| 1.96.2 = 1.99 = 1.104 = 1.107 = 1.128 | 22 | SISSSSSYIY YADSVKG | RFTISRDNAKNSL YLQMNSLRAEDTA VYYCAR | GGDGYNY YYDFY | WGQGTLVTVSS | |
| 1.100.1 | 18 | SISSSSSYIY YADSVKG | RFTISRDNAKNSL YLQMNSLRAEDTA VYYCAR | GGDGYNY YYFDY | WGQGTLVTVSS | |
| 1.140.1 = 1.124 = 1.148 | 6 | SISSSSSYIY YADSVKG | RFTISRDNAKNSL YLQMNSLRAEDTA VYYCAR | GGDGYNY YYFDY | WGQGTLVTVSS | |
| | 57 | NIKQDGSEKY YVDSVKG | RFTISRDNAKNSL YLQMNSLRAEDTA VYYCA# | ###YGMDV | WGQGTTVTVSS | |
| 1.43.1 = 1.41 = 1.22.1 | 10 | NIKQDGSEKY YVDSVKG | RFTISRDNAKNSL HLQMNSLRAEDTA AYYCAS | FRDYGMDV | WGQGTTVTVSS | |
| | 59 | YIYYSGSTYY NPSLKS | RVTISVDTSKNQF SLKLSSVTAADTA VYYCAR | ###ITMVR GVYYYYYG MDV | WGQGTTVTVSS | |
| 1.44.1 | 2 | YIYYSGSTYY NPSLKS | RVTISVDTSKNQF SLKLSSVTAADTA VYYCAR | EGPITIVR GVYYYFYG MDV | WVQGTTVTVSS | |
| | 56 | AIGTAGDTYY PGSVKG | RFTISRENAKNSL YLQMNSLRAGDTA VYYCAR | #GYSS##Y YYYGMDV | WGQGTTVTVSS | |
| 1.71.2 = 1.71.3 | 42 | AIGTAGDTFY PGSVKG | RFTISRENAKNSL YLAMNSLRAGDTA VYYCAR | EGYSSGRY FYYGMDV | WGQGTTVTVSS | |

TABLE 4(a)

Heavy Chain Analysis

| Chain Name | SEQ ID NO: | V | D | J | FR1 | CDR1 | FR2 |
|---|---|---|---|---|---|---|---|
| | 54 | | Germline | | EVQLVESGGGLVKPG GSLRLSCAASGFTFS | SYSMN | WVRQAPG KGLEWVS |
| 1.14.1 | 14 | VH3-21 | D5-24 | JH4B | EVQLVESGGGLVKPG GSLRLSCAASGFTFS | SYSMN | EVRQAPG KGLEWVS |
| 1.18.1 | 26 | " | " | " | EVQLVESGGGLVKPG GSLRLSCAASGFTFS | SYSMN | WVRQAPG KGLEWVS |
| 1.20.1 = 1.19 | 30 | " | " | " | EVQLVESGGGLVKPG GSLRLSCAASGFTFS | SYTMN | WVRQAPG KGLEWVS |
| 1.24.3 = 1.22.2 = 1.71.1 | 38 | " | " | " | EVQLVESGGGLVKPG GSLRLSCAASGFTFS | SYSMN | WVRQAPG KGLEWVS |
| 1.39.1 | 34 | " | " | " | EVQLVESGGGLVKPG GSLRLSCAASGFTFS | SYSMN | WVRQAPG KGLEWVS |
| 1.96.2 = 1.99 = 1.104 = 1.107 = 1.128 | 22 | " | " | " | EVQLVESGGGLVKPG GSLRLSCAASGFTFS | SYSMN | WVRQAPG KGLEWVS |
| 1.100.1 | 18 | " | " | " | EVQLVESGGGLVKPG GSLRLSCAASGFTFS | SYSMN | WVRQAPG KGLEWVS |

TABLE 4(a)-continued

| | | | Heavy Chain Analysis | | | |
|---|---|---|---|---|---|---|
| 1.140.1 =<br>1.124 =<br>1.148 | 6 | " | " " | EVQLVESGGGLVKPG<br>GSLRLSCAASGFTFS | SYSMN | WVRQAPR<br>KGLEWVS |
| | 58 | | Germline | EVQLVESGGGLVQPG<br>GSLRLSCAASGFTFS | SYWMS | WVRQAPG<br>KGLEWVA |
| 1.43.1 =<br>1.41 =<br>1.22.1 | | VH3-7 | D5-24 JH6B | EVQLVESGGGLVQPG<br>GSLRLSCAASGFTFS | SYWMH | WVRQTPG<br>KGLEWVA |
| | 10 | | Germline | QVQLQESGPGLVKPS<br>QTLSLTCTVSGGSIS | SGGYYWS | WIRQHPG<br>KGLEWIG |
| 1.44.1 | 2 | VH4-31 | D3-10 JH6B | QVQLQESGPGLVKPS<br>QTLSLTCTVSGGSIS | SGGYYWS | WIRQHPG<br>KGLEWIG |
| | 56 | | Germline | EVQLVESGGGLVQPG<br>GSLRLSCAASGFTFS | SYDMH | WVRQATG<br>KGLEWVS |
| 1.71.2 =<br>1.71.3 | 42 | VH3-13 | D6-19 JH6B | EVQLVESGGGLVQPG<br>GSLRLSCTASGFPFS | SYDMH | WVRQATG<br>KGLEWVS |

| Chain Name | SEQ<br>ID NO: | CDR2 | FR3 | CDR3 | FR4 |
|---|---|---|---|---|---|
| | 54 | SISSSSSYIY<br>YADSVKG | RFTISRDNAKNSLYL<br>QMNSLRAEDTAVYYC<br>AR | ##DGYNY<br>#YFDY | WGQGTLV<br>TVSS |
| 1.14.1 | 14 | SISSSSSYIY<br>YADSVKG | RFTISRDNAKNSLYL<br>QMNSLRAEDTAVYYC<br>AR | GGDGYNY<br>YYFDY | WGQGTLV<br>TVSS |
| 1.18.1 | 26 | SISSSSSYIY<br>YADSVKG | RFTISRDNAKNSLYL<br>QMNSLSAEDTAVYSC<br>AR | GGDGYNY<br>YYFDY | WGQGTLV<br>TVSS |
| 1.20.1 =<br>1.19 | 30 | SISSSSSYIY<br>YADSVKG | RFTISRDNAKNSLYL<br>QMNSLSAEDTAVYSC<br>AR | GGDGYNY<br>YYFDY | WGQGTLV<br>TVSS |
| 1.24.3 =<br>1.22.2 =<br>1.71.1 | 38 | SISSSSSYIY<br>YADSVKG | RFTISRDNAKNSLYL<br>QMNSLRAEDTAVYYC<br>AR | GGDGYNY<br>YYFDY | WGQGTLV<br>TVSS |
| 1.39.1 | 34 | SISSSSSYIY<br>YADSVKG | RFTISRDNAKNSLYL<br>QMNSLRAEDTAVYYC<br>AR | GGDGYNY<br>YYFDY | WGQGTLV<br>TVSS |
| 1.96.2 =<br>1.99 =<br>1.104 =<br>1.107 =<br>1.128 | 22 | SISSSSSYIY<br>YADSVKG | RFTISRDNAKNSLYL<br>QMNSLRAEDTAVYYC<br>AR | GGDGYNY<br>YYFDY | WGQGTLV<br>TVSS |
| 1.100.1 | 18 | SISSSSSYIY<br>YADSVKG | RFTISRDNAKNSLYL<br>QMNSLRAEDTAVYYC<br>AR | GGDGYNY<br>YYFDY | WGQGTLV<br>TVSS |
| 1.140.1 =<br>1.124 =<br>1.148 | 6 | SISSSSSYIY<br>YADSVKG | RFTISRDNAKNSLYL<br>QMNSLRAEDTAVYYC<br>AR | GGDGYNY<br>YYFDY | WGQGTLV<br>TVSS |
| | 58 | NIKQDGSEKY<br>YVDSVKG | RFTISRDNAKNSLYL<br>QMNSLRAEDTAVYYC<br>A# | #RDYGMD<br>V | WGQGTTV<br>TVSS |
| 1.43.1 =<br>1.41 =<br>1.22.1 | | NIKQDGSEKY<br>YVDSVKG | RFTISRDNAKNSLHL<br>QMNSLRAEDTAAYYC<br>AS | FRDYGMD<br>V | WGQGTTV<br>TVSS |
| | 10 | YIYYSGSTYY<br>NPSLKS | RFTISVDTSKNQFSL<br>KLSSVTAADTAVYYC<br>AR | ###ITMV<br>RGVYYYY<br>YGMDV | WGQGTTV<br>TVSS |

TABLE 4(a)-continued

Heavy Chain Analysis

| | | | | | |
|---|---|---|---|---|---|
| 1.44.1 | 2 | YIYYSGSTYY NPSLKS | RVTISVDTSKNQFSL KLSSVTAADTAVYYC AR | EGPITIV RGVYYYF YGMDV | WGQGTTV TVSS |
| | 56 | AIGTAGDTYY PGSVKG | RFTSIRENAKNSLYL QMNSLRAGDTAVYYC AR | #GYSS## YYYYGMD V | WGQGTTV TVSS |
| 1.71.2 = 1.71.3 | 42 | AIGTAGDTFY PGSVKG | RFTISRENAKNSLYL QMNSLRAGDTAVYYC AR | EGYSSGR YFYYGMD V | WGQGTTV TVSS |

TABLE 5

Light Chain Analysis

| Chain Name | SEQ ID NO: | V | J | FR1 | CDR1 | FR2 |
|---|---|---|---|---|---|---|
| | 51 | Germline | | DIVMTQSPDSLAV SLGERATINC | KSSQSVLYSSNN KNYLA | WYQQKPGQ PPKLLIY |
| 1.14.1 | 16 | B3 | JK3 (VK4) | DIVMTQSPDSLAV SLGERATITC | KSSQSVFFRSNN KNCLT | WYQQRPGQ PPNLLIY |
| 1.18.1 | 28 | " | " | <u>DIVMTQSPGSLVV SLGERATITC</u> | KSSQSVFFRSNN KNCLA | WYQQRPGQ SPNLLIY |
| 1.20.1 = 1.19 | 32 | " | " | DIVMTQSPGSLVV SLGERATITC | KSSQSVFFRSNN KNCLA | WYQQRPGQ SPNLLIY |
| 1.24.3 = 1.22.2 = 1.71.1 | 40 | " | " | DIVMTQFPDLSAV SLDERATINC | KSSQSVFFRSNN KNCLA | WYQQRPGQ PPNLLIY |
| 1.39.1 | 36 | " | " | DIVMTQSPDSLAV SLGERATITC | KSSQSVFFRSNN KNCLA | WYQQRPGQ PPNLLIY |
| 1.96.2 = 1.99 = 1.104 = 1.107 = 1.128 | 24 | " | " | DIVNTQSPDSLAV SLGERATITC | KSSQSVFFRSNN KNCLA | WYQQRPGQ PPNLLFY |
| 1.100.1 | 20 | " | " | DIVMTQSPDSLAV SLGERATITC | KSSQSVFFRSNN KNCLA | WYQQRPGQ PPNLLIY |
| 1.140.1 = 1.124 = 1.148 | 8 | " | " | DIVMTQSPDSLAV SLGERATITC | KSSQSVFFRSNN KNCLA | WYQQRPGQ PPNLLIY |
| | 50 | Germline | | DIQMTQSPSSLSA SVGDRVTITC | RASQGISNYLA | WFQQKPGK APKSLIY |
| 1.43.1 = 1.41 = 1.22.1 | 12 | L1 | JK5 (VK1) | DIQMTQSPSSLSA SVGDRVTITC | RASQGISNHLA | WFQQKPGK APKSLIY |
| | 52 | Germline | | DIVMTQTPLSLSV TPGQPASISC | KSSQSLLHSDGK TYLY | WYLQKPGQ PPQLLIY |
| 1.44.1 | 4 | A2 | JK1 (VK2) | DIVMTQTPLSLSV TPGQPASISC | KSSQSLLHSDGK TYLY | WYLQKPGQ PPQPLIY |
| | 53 | Germline | | DVVMTQSPLSLPV TLGQPASISC | RSSQSLVYSDGN TYLN | WFQQRPGQ SPRRLIY |
| 1.71.1 = 1.71.3 | 44 | A1 | JK4 | DVVMTQSPLSLPV TLGQPASISC | RSSQSLVYSDGN TYLN | WFQQRPGQ SPRRLIY |

TABLE 5-continued

Light Chain Analysis

| Chain Name | SEQ ID NO: | CDR2 | FR3 | CDR3 | FR4 |
|---|---|---|---|---|---|
|  | 51 | WASTRES | GVPDRFSGSGSGT DFTLTISSLQAED VAVYYC | QQYYSTPFT | FGPGTKVDIK |
| 1.14.1 | 16 | WASTRES | GVPDRFSGSGSGT DFTLTINNLQAED VAVYYC | QQYFGSPFT | FGPGTKVDIK |
| 1.18.1 | 28 | WASTRES | GVPDRFSGSGSGT DFTLTISSLQAED VAVYYC | QQYFGSPFT | FGPGTKVDIK |
| 1.20.1 = 1.19 | 32 | WASTRES | GVPDRFSGSGSGT DFTLTISSLQAED VAVYYC | QQYFGSPFT | FGPGTKVDIK |
| 1.24.3 = 1.22.2 = 1.71.1 | 40 | WASTRES | GVPDRFSGSGSGT DFTLTISSLQAED VAFYYC | QQYYSSPFT | FGPGTKVDIK |
| 1.39.1 | 36 | WASSRES | GVPDRFSGSGSGT DFALTISSLQTED VAVYYC | QQYFGSPFT | FGPGTKVDIK |
| 1.96.2 = 1.99 = 1.104 = 1.107 = 1.128 | 24 | WASTRES | GVPDRFSGSGSGT DFTLTISSLQAED VAVYYC | QQYFGSPFT | LGPGTKVDIK |
| 1.100.1 | 20 | WASTRES | GVPDRFSGSGCGT DFTLTISSLQAED VAVYYC | QQYFGSPFT | FGPGTKVDIK |
| 1.140.1 = 1.124 = 1.148 | 8 | WASTRES | GVPDRFSGSGSGT DFTLTISSLQAED VAVYYC | QQYFGSPFT | FGPGTKVDIK |
|  | 50 | AASSLQS | GVPSRFSGSGSGT DFTLTISSLQPED FATYYC | QQYNSYPIT | FGQGTRLEIK |
| 1.43.1 = 1.41 = 1.22.1 | 12 | GASSLQT | GVPSKFSGSGSGT DFTLTISSLQPED FASYFC | QQYKGYPIT | FGQGTRLEIK |
|  | 52 | EVSNRFS | GVPDRFSGSGSGT DFTLKISRVEAED VGVYYC | MQSIQLPRT | FGQGTKVEIK |
| 1.44.1 | 4 | EVSNRFS | GVPDRFSGSGSGT DFTLKISRVEAED VGIYYC | MQSKQLPRT | FGQGTKVEIK |
|  | 53 | KVSNWDS | GVPDRFSGSGSGT DFTLKISRVEAED VGVYYC | MQGTHW##T | FGGGTKVEIK |
| 1.71.1 = 1.71.3 | 44 | KVSNWDS | GVPDRFSGSGSGT DFTLKISRVEAED VGVYYC | MQGTHWPLT | FGGGTKVEIK |

TABLE 6

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | V | L | Y | C | K | K | Y | S | S |
| N | V | L | Y | C | K | K | Y | S | I |
| N | V | L | Y | C | K | K | Y | G | S |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | V | L | Y | C | K | K | Y | G | I |
| N | V | L | Y | C | K | K | F | S | S |
| N | V | L | Y | C | K | K | F | S | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | V | L | Y | C | K | K | F | G | S |
| N | V | L | Y | C | K | K | F | G | I |
| N | V | L | Y | C | K | N | Y | S | S |
| N | V | L | Y | C | K | N | Y | G | S |
| N | V | L | Y | C | K | N | Y | G | I |
| N | V | L | Y | C | K | N | F | S | S |
| N | V | L | Y | C | K | N | F | S | I |
| N | V | L | Y | C | K | N | F | G | S |
| N | V | L | Y | C | K | N | F | G | I |
| N | V | L | Y | C | R | K | Y | S | S |
| N | V | L | Y | C | R | K | Y | S | I |
| N | V | L | Y | C | R | K | Y | G | S |
| N | V | L | Y | C | R | K | Y | G | I |
| N | V | L | Y | C | R | K | F | S | S |
| N | V | L | Y | C | R | K | F | S | I |
| N | V | L | Y | C | R | K | F | G | S |
| N | V | L | Y | C | R | K | F | G | I |
| N | V | L | Y | C | R | N | Y | S | S |
| N | V | L | Y | C | R | N | Y | S | I |
| N | V | L | Y | C | R | N | Y | G | S |
| N | V | L | Y | C | R | N | Y | G | I |
| N | V | L | Y | C | R | N | F | S | S |
| N | V | L | Y | C | R | N | F | S | I |
| N | V | L | Y | C | R | N | F | G | S |
| N | V | L | Y | C | R | N | F | G | I |
| N | V | L | Y | Y | K | K | Y | S | S |
| N | V | L | Y | Y | K | K | Y | S | I |
| N | V | L | Y | Y | K | K | Y | G | S |
| N | V | L | Y | Y | K | K | Y | G | I |
| N | V | L | Y | Y | K | K | F | S | S |
| N | V | L | Y | Y | K | K | F | S | I |
| N | V | L | Y | Y | K | K | F | G | S |
| N | V | L | Y | Y | K | K | F | G | I |
| N | V | L | Y | Y | K | N | Y | S | S |
| N | V | L | Y | Y | K | N | Y | S | I |
| N | V | L | Y | Y | K | N | Y | G | S |
| N | V | L | Y | Y | K | N | Y | G | I |
| N | V | L | Y | Y | K | N | F | S | S |
| N | V | L | Y | Y | K | N | F | S | I |
| N | V | L | Y | Y | K | N | F | G | S |
| N | V | L | Y | Y | K | N | F | G | I |
| N | V | L | Y | Y | R | K | Y | S | S |
| N | V | L | Y | Y | R | K | Y | S | I |
| N | V | L | Y | Y | R | K | Y | G | S |
| N | V | L | Y | Y | R | K | Y | G | I |
| N | V | L | Y | Y | R | K | F | S | S |
| N | V | L | Y | Y | R | K | F | S | I |
| N | V | L | Y | Y | R | K | F | G | S |
| N | V | L | Y | Y | R | K | F | G | I |
| N | V | L | Y | Y | R | N | Y | S | S |
| N | V | L | Y | Y | R | N | Y | S | I |
| N | V | L | Y | Y | R | N | Y | G | S |
| N | V | L | Y | Y | R | N | Y | G | I |
| N | V | L | Y | Y | R | N | F | S | S |
| N | V | L | Y | Y | R | N | F | S | I |
| N | V | L | Y | Y | R | N | F | G | S |
| N | V | L | Y | Y | R | N | F | G | I |
| N | V | L | R | C | K | K | Y | S | S |
| N | V | L | R | C | K | K | Y | S | I |
| N | V | L | R | C | K | K | Y | G | S |
| N | V | L | R | C | K | K | Y | G | I |
| N | V | L | R | C | K | K | F | S | S |
| N | V | L | R | C | K | K | F | S | I |
| N | V | L | R | C | K | K | F | G | S |
| N | V | L | R | C | K | K | F | G | I |
| N | V | L | R | C | K | N | Y | S | S |
| N | V | L | R | C | K | N | Y | S | I |
| N | V | L | R | C | K | N | Y | G | S |
| N | V | L | R | C | K | N | Y | G | I |
| N | V | L | R | C | K | N | F | S | S |
| N | V | L | R | C | K | N | F | S | I |
| N | V | L | R | C | K | N | F | G | S |
| N | V | L | R | C | K | N | F | G | I |
| N | V | L | R | C | R | K | Y | S | S |
| N | V | L | R | C | R | K | Y | S | I |
| N | V | L | R | C | R | K | Y | G | S |
| N | V | L | R | C | R | K | Y | G | I |
| N | V | L | R | C | R | K | F | S | S |
| N | V | L | R | C | R | K | F | S | I |
| N | V | L | R | C | R | K | F | G | S |
| N | V | L | R | C | R | K | F | G | I |
| N | V | L | R | C | R | N | Y | S | S |
| N | V | L | R | C | R | N | Y | S | I |
| N | V | L | R | C | R | N | Y | G | S |
| N | V | L | R | C | R | N | Y | G | I |
| N | V | L | R | C | R | N | F | S | S |
| N | V | L | R | C | R | N | F | S | I |
| N | V | L | R | C | R | N | F | G | S |
| N | V | L | R | C | R | N | F | G | I |
| N | V | L | R | Y | K | K | Y | S | S |
| N | V | L | R | Y | K | K | Y | S | I |
| N | V | L | R | Y | K | K | Y | G | S |
| N | V | L | R | Y | K | K | Y | G | I |
| N | V | L | R | Y | K | K | F | S | S |
| N | V | L | R | Y | K | K | F | S | I |
| N | V | L | R | Y | K | K | F | G | S |
| N | V | L | R | Y | K | K | F | G | I |
| N | V | L | R | Y | K | N | Y | S | S |
| N | V | L | R | Y | K | N | Y | S | I |
| N | V | L | R | Y | K | N | Y | G | S |
| N | V | L | R | Y | K | N | Y | G | I |
| N | V | L | R | Y | K | N | F | S | S |
| N | V | L | R | Y | K | N | F | S | I |
| N | V | L | R | Y | K | N | F | G | S |
| N | V | L | R | Y | K | N | F | G | I |
| N | V | L | R | Y | R | K | Y | S | S |
| N | V | L | R | Y | R | K | Y | S | I |
| N | V | L | R | Y | R | K | Y | G | S |
| N | V | L | R | Y | R | K | Y | G | I |
| N | V | L | R | Y | R | K | F | S | S |
| N | V | L | R | Y | R | K | F | S | I |
| N | V | L | R | Y | R | K | F | G | S |
| N | V | L | R | Y | R | K | F | G | I |
| N | V | L | R | Y | R | N | Y | S | S |
| N | V | L | R | Y | R | N | Y | S | I |
| N | V | L | R | Y | R | N | Y | G | S |
| N | V | L | R | Y | R | N | Y | G | I |
| N | V | L | R | Y | R | N | F | S | S |
| N | V | L | R | Y | R | N | F | S | I |
| N | V | L | R | Y | R | N | F | G | S |
| N | V | L | R | Y | R | N | F | G | I |
| N | V | F | Y | C | K | K | Y | S | S |
| N | V | F | Y | C | K | K | Y | S | I |
| N | V | F | Y | C | K | K | Y | G | S |
| N | V | F | Y | C | K | K | Y | G | I |
| N | V | F | Y | C | K | K | F | S | S |
| N | V | F | Y | C | K | K | F | S | I |
| N | V | F | Y | C | K | K | F | G | S |
| N | V | F | Y | C | K | K | F | G | I |
| N | V | F | Y | C | K | N | Y | S | S |
| N | V | F | Y | C | K | N | Y | S | I |
| N | V | F | Y | C | K | N | Y | G | S |
| N | V | F | Y | C | K | N | Y | G | I |
| N | V | F | Y | C | K | N | F | S | S |
| N | V | F | Y | C | K | N | F | S | I |
| N | V | F | Y | C | K | N | F | G | S |
| N | V | F | Y | C | K | N | F | G | I |
| N | V | F | Y | C | R | K | Y | S | S |
| N | V | F | Y | C | R | K | Y | S | I |
| N | V | F | Y | C | R | K | Y | G | S |
| N | V | F | Y | C | R | K | Y | G | I |
| N | V | F | Y | C | R | K | F | S | S |
| N | V | F | Y | C | R | K | F | S | I |
| N | V | F | Y | C | R | K | F | G | S |
| N | V | F | Y | C | R | K | F | G | I |
| N | V | F | Y | C | R | N | Y | S | S |
| N | V | F | Y | C | R | N | Y | S | I |
| N | V | F | Y | C | R | N | Y | G | S |
| N | V | F | Y | C | R | N | Y | G | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | V | F | Y | C | R | N | F | S | S |
| N | V | F | Y | C | R | N | F | S | I |
| N | V | F | Y | C | R | N | F | G | S |
| N | V | F | Y | C | R | N | F | G | I |
| N | V | F | Y | Y | K | K | Y | S | S |
| N | V | F | Y | Y | K | K | Y | S | I |
| N | V | F | Y | Y | K | K | Y | G | S |
| N | V | F | Y | Y | K | K | Y | G | I |
| N | V | F | Y | Y | K | K | F | S | S |
| N | V | F | Y | Y | K | K | F | S | I |
| N | V | F | Y | Y | K | K | F | G | S |
| N | V | F | Y | Y | K | K | F | G | I |
| N | V | F | Y | Y | K | N | Y | S | S |
| N | V | F | Y | Y | K | N | Y | S | I |
| N | V | F | Y | Y | K | N | Y | G | S |
| N | V | F | Y | Y | K | N | Y | G | I |
| N | V | F | Y | Y | K | N | F | S | S |
| N | V | F | Y | Y | K | N | F | S | I |
| N | V | F | Y | Y | K | N | F | G | S |
| N | V | F | Y | Y | K | N | F | G | I |
| N | V | F | Y | Y | R | K | Y | S | S |
| N | V | F | Y | Y | R | K | Y | S | I |
| N | V | F | Y | Y | R | K | Y | G | S |
| N | V | F | Y | Y | R | K | Y | G | I |
| N | V | F | Y | Y | R | K | F | S | S |
| N | V | F | Y | Y | R | K | F | S | I |
| N | V | F | Y | Y | R | K | F | G | S |
| N | V | F | Y | Y | R | K | F | G | I |
| N | V | F | Y | Y | R | N | Y | S | S |
| N | V | F | Y | Y | R | N | Y | S | I |
| N | V | F | Y | Y | R | N | Y | G | S |
| N | V | F | Y | Y | R | N | Y | G | I |
| N | V | F | Y | Y | R | N | F | S | S |
| N | V | F | Y | Y | R | N | F | S | I |
| N | V | F | Y | Y | R | N | F | G | S |
| N | V | F | Y | Y | R | N | F | G | I |
| N | V | F | R | C | K | K | Y | S | S |
| N | V | F | R | C | K | K | Y | S | I |
| N | V | F | R | C | K | K | Y | G | S |
| N | V | F | R | C | K | K | Y | G | I |
| N | V | F | R | C | K | K | F | S | S |
| N | V | F | R | C | K | K | F | S | I |
| N | V | F | R | C | K | K | F | G | S |
| N | V | F | R | C | K | K | F | G | I |
| N | V | F | R | C | K | N | Y | S | S |
| N | V | F | R | C | K | N | Y | S | I |
| N | V | F | R | C | K | N | Y | G | S |
| N | V | F | R | C | K | N | Y | G | I |
| N | V | F | R | C | K | N | F | S | S |
| N | V | F | R | C | K | N | F | S | I |
| N | V | F | R | C | K | N | F | G | S |
| N | V | F | R | C | K | N | F | G | I |
| N | V | F | R | C | R | K | Y | S | S |
| N | V | F | R | C | R | K | Y | S | I |
| N | V | F | R | C | R | K | Y | G | S |
| N | V | F | R | C | R | K | Y | G | I |
| N | V | F | R | C | R | K | F | S | S |
| N | V | F | R | C | R | K | F | S | I |
| N | V | F | R | C | R | K | F | G | S |
| N | V | F | R | C | R | K | F | G | I |
| N | V | F | R | C | R | N | Y | S | S |
| N | V | F | R | C | R | N | Y | S | I |
| N | V | F | R | C | R | N | Y | G | S |
| N | V | F | R | C | R | N | Y | G | I |
| N | V | F | R | C | R | N | F | S | S |
| N | V | F | R | C | R | N | F | S | I |
| N | V | F | R | C | R | N | F | G | S |
| N | V | F | R | C | R | N | F | G | I |
| N | V | F | R | Y | K | K | Y | S | S |
| N | V | F | R | Y | K | K | Y | S | I |
| N | V | F | R | Y | K | K | Y | G | S |
| N | V | F | R | Y | K | K | Y | G | I |
| N | V | F | R | Y | K | K | F | S | S |
| N | V | F | R | Y | K | K | F | S | I |
| N | V | F | R | Y | K | K | F | G | S |
| N | V | F | R | Y | K | K | F | G | I |
| N | V | F | R | Y | K | N | Y | S | S |
| N | V | F | R | Y | K | N | Y | S | I |
| N | V | F | R | Y | K | N | Y | G | S |
| N | V | F | R | Y | K | N | Y | G | I |
| N | V | F | R | Y | K | N | F | S | S |
| N | V | F | R | Y | K | N | F | S | I |
| N | V | F | R | Y | K | N | F | G | S |
| N | V | F | R | Y | K | N | F | G | I |
| N | V | F | R | Y | R | K | Y | S | S |
| N | V | F | R | Y | R | K | Y | S | I |
| N | V | F | R | Y | R | K | Y | G | S |
| N | V | F | R | Y | R | K | Y | G | I |
| N | V | F | R | Y | R | K | F | S | S |
| N | V | F | R | Y | R | K | F | S | I |
| N | V | F | R | Y | R | K | F | G | S |
| N | V | F | R | Y | R | K | F | G | I |
| N | V | F | R | Y | R | N | Y | S | S |
| N | V | F | R | Y | R | N | Y | S | I |
| N | V | F | R | Y | R | N | Y | G | S |
| N | V | F | R | Y | R | N | Y | G | I |
| N | V | F | R | Y | R | N | F | S | S |
| N | V | F | R | Y | R | N | F | S | I |
| N | V | F | R | Y | R | N | F | G | S |
| N | V | F | R | Y | R | N | F | G | I |
| N | F | L | Y | C | K | K | Y | S | S |
| N | F | L | Y | C | K | K | Y | S | I |
| N | F | L | Y | C | K | K | Y | G | S |
| N | F | L | Y | C | K | K | Y | G | I |
| N | F | L | Y | C | K | K | F | S | S |
| N | F | L | Y | C | K | K | F | S | I |
| N | F | L | Y | C | K | K | F | G | S |
| N | F | L | Y | C | K | K | F | G | I |
| N | F | L | Y | C | K | N | Y | S | S |
| N | F | L | Y | C | K | N | Y | S | I |
| N | F | L | Y | C | K | N | Y | G | S |
| N | F | L | Y | C | K | N | Y | G | I |
| N | F | L | Y | C | K | N | F | S | S |
| N | F | L | Y | C | K | N | F | S | I |
| N | F | L | Y | C | K | N | F | G | S |
| N | F | L | Y | C | K | N | F | G | I |
| N | F | L | Y | C | R | K | Y | S | S |
| N | F | L | Y | C | R | K | Y | S | I |
| N | F | L | Y | C | R | K | Y | G | S |
| N | F | L | Y | C | R | K | Y | G | I |
| N | F | L | Y | C | R | K | F | S | S |
| N | F | L | Y | C | R | K | F | S | I |
| N | F | L | Y | C | R | K | F | G | S |
| N | F | L | Y | C | R | K | F | G | I |
| N | F | L | Y | C | R | N | Y | S | S |
| N | F | L | Y | C | R | N | Y | S | I |
| N | F | L | Y | C | R | N | Y | G | S |
| N | F | L | Y | C | R | N | Y | G | I |
| N | F | L | Y | C | R | N | F | S | S |
| N | F | L | Y | C | R | N | F | S | I |
| N | F | L | Y | C | R | N | F | G | S |
| N | F | L | Y | C | R | N | F | G | I |
| N | F | L | Y | Y | K | K | Y | S | S |
| N | F | L | Y | Y | K | K | Y | S | I |
| N | F | L | Y | Y | K | K | Y | G | S |
| N | F | L | Y | Y | K | K | Y | G | I |
| N | F | L | Y | Y | K | K | F | S | S |
| N | F | L | Y | Y | K | K | F | S | I |
| N | F | L | Y | Y | K | K | F | G | S |
| N | F | L | Y | Y | K | K | F | G | I |
| N | F | L | Y | Y | K | N | Y | S | S |
| N | F | L | Y | Y | K | N | Y | S | I |
| N | F | L | Y | Y | K | N | Y | G | S |
| N | F | L | Y | Y | K | N | Y | G | I |
| N | F | L | Y | Y | K | N | F | S | S |
| N | F | L | Y | Y | K | N | F | S | I |
| N | F | L | Y | Y | K | N | F | G | S |
| N | F | L | Y | Y | K | N | F | G | I |
| N | F | L | Y | Y | R | K | Y | S | S |
| N | F | L | Y | Y | R | K | Y | S | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | F | L | Y | Y | R | K | Y | G | S |
| N | F | L | Y | Y | R | K | Y | G | I |
| N | F | L | Y | Y | R | K | F | S | S |
| N | F | L | Y | Y | R | K | F | S | I |
| N | F | L | Y | Y | R | K | F | G | S |
| N | F | L | Y | Y | R | K | F | G | I |
| N | F | L | Y | Y | R | N | Y | S | S |
| N | F | L | Y | Y | R | N | Y | S | I |
| N | F | L | Y | Y | R | N | Y | G | S |
| N | F | L | Y | Y | R | N | Y | G | I |
| N | F | L | Y | Y | R | N | F | S | S |
| N | F | L | Y | Y | R | N | F | S | I |
| N | F | L | Y | Y | R | N | F | G | S |
| N | F | L | Y | Y | R | N | F | G | I |
| N | F | L | R | C | K | K | Y | S | S |
| N | F | L | R | C | K | K | Y | S | I |
| N | F | L | R | C | K | K | Y | G | S |
| N | F | L | R | C | K | K | Y | G | I |
| N | F | L | R | C | K | K | F | S | S |
| N | F | L | R | C | K | K | F | S | I |
| N | F | L | R | C | K | K | F | G | S |
| N | F | L | R | C | K | K | F | G | I |
| N | F | L | R | C | K | N | Y | S | S |
| N | F | L | R | C | K | N | Y | S | I |
| N | F | L | R | C | K | N | Y | G | S |
| N | F | L | R | C | K | N | Y | G | I |
| N | F | L | R | C | K | N | F | S | S |
| N | F | L | R | C | K | N | F | S | I |
| N | F | L | R | C | K | N | F | G | S |
| N | F | L | R | C | K | N | F | G | I |
| N | F | L | R | C | R | K | Y | S | S |
| N | F | L | R | C | R | K | Y | S | I |
| N | F | L | R | C | R | K | Y | G | S |
| N | F | L | R | C | R | K | Y | G | I |
| N | F | L | R | C | R | K | F | S | S |
| N | F | L | R | C | R | K | F | S | I |
| N | F | L | R | C | R | K | F | G | S |
| N | F | L | R | C | R | K | F | G | I |
| N | F | L | R | C | R | N | Y | S | S |
| N | F | L | R | C | R | N | Y | S | I |
| N | F | L | R | C | R | N | Y | G | S |
| N | F | L | R | C | R | N | Y | G | I |
| N | F | L | R | C | R | N | F | S | S |
| N | F | L | R | C | R | N | F | S | I |
| N | F | L | R | C | R | N | F | G | S |
| N | F | L | R | C | R | N | F | G | I |
| N | F | L | R | Y | K | K | Y | S | S |
| N | F | L | R | Y | K | K | Y | S | I |
| N | F | L | R | Y | K | K | Y | G | S |
| N | F | L | R | Y | K | K | Y | G | I |
| N | F | L | R | Y | K | K | F | S | S |
| N | F | L | R | Y | K | K | F | S | I |
| N | F | L | R | Y | K | K | F | G | S |
| N | F | L | R | Y | K | K | F | G | I |
| N | F | L | R | Y | K | N | Y | S | S |
| N | F | L | R | Y | K | N | Y | S | I |
| N | F | L | R | Y | K | N | Y | G | S |
| N | F | L | R | Y | K | N | Y | G | I |
| N | F | L | R | Y | K | N | F | S | S |
| N | F | L | R | Y | K | N | F | S | I |
| N | F | L | R | Y | K | N | F | G | S |
| N | F | L | R | Y | K | N | F | G | I |
| N | F | L | R | Y | R | K | Y | S | S |
| N | F | L | R | Y | R | K | Y | S | I |
| N | F | L | R | Y | R | K | Y | G | S |
| N | F | L | R | Y | R | K | Y | G | I |
| N | F | L | R | Y | R | K | F | S | S |
| N | F | L | R | Y | R | K | F | S | I |
| N | F | L | R | Y | R | K | F | G | S |
| N | F | L | R | Y | R | K | F | G | I |
| N | F | L | R | Y | R | N | Y | S | S |
| N | F | L | R | Y | R | N | Y | S | I |
| N | F | L | R | Y | R | N | Y | G | S |
| N | F | L | R | Y | R | N | Y | G | I |
| N | F | L | R | Y | R | N | F | S | S |
| N | F | L | R | Y | R | N | F | S | I |
| N | F | L | R | Y | R | N | F | G | S |
| N | F | F | Y | C | K | K | Y | S | S |
| N | F | F | Y | C | K | K | Y | S | I |
| N | F | F | Y | C | K | K | Y | G | S |
| N | F | F | Y | C | K | K | Y | G | I |
| N | F | F | Y | C | K | K | F | S | S |
| N | F | F | Y | C | K | K | F | S | I |
| N | F | F | Y | C | K | K | F | G | S |
| N | F | F | Y | C | K | K | F | G | I |
| N | F | F | Y | C | K | N | Y | S | S |
| N | F | F | Y | C | K | N | Y | S | I |
| N | F | F | Y | C | K | N | Y | G | S |
| N | F | F | Y | C | K | N | Y | G | I |
| N | F | F | Y | C | K | N | F | S | S |
| N | F | F | Y | C | K | N | F | S | I |
| N | F | F | Y | C | K | N | F | G | S |
| N | F | F | Y | C | K | N | F | G | I |
| N | F | F | Y | C | R | K | Y | S | S |
| N | F | F | Y | C | R | K | Y | S | I |
| N | F | F | Y | C | R | K | Y | G | S |
| N | F | F | Y | C | R | K | Y | G | I |
| N | F | F | Y | C | R | K | F | S | S |
| N | F | F | Y | C | R | K | F | S | I |
| N | F | F | Y | C | R | K | F | G | S |
| N | F | F | Y | C | R | K | F | G | I |
| N | F | F | Y | C | R | N | Y | S | S |
| N | F | F | Y | C | R | N | Y | S | I |
| N | F | F | Y | C | R | N | Y | G | S |
| N | F | F | Y | C | R | N | Y | G | I |
| N | F | F | Y | C | R | N | F | S | S |
| N | F | F | Y | C | R | N | F | S | I |
| N | F | F | Y | C | R | N | F | G | S |
| N | F | F | Y | C | R | N | F | G | I |
| N | F | F | Y | Y | K | K | Y | S | S |
| N | F | F | Y | Y | K | K | Y | S | I |
| N | F | F | Y | Y | K | K | Y | G | S |
| N | F | F | Y | Y | K | K | Y | G | I |
| N | F | F | Y | Y | K | K | F | S | S |
| N | F | F | Y | Y | K | K | F | S | I |
| N | F | F | Y | Y | K | K | F | G | S |
| N | F | F | Y | Y | K | K | F | G | I |
| N | F | F | Y | Y | K | N | Y | S | S |
| N | F | F | Y | Y | K | N | Y | S | I |
| N | F | F | Y | Y | K | N | Y | G | S |
| N | F | F | Y | Y | K | N | Y | G | I |
| N | F | F | Y | Y | K | N | F | S | S |
| N | F | F | Y | Y | K | N | F | S | I |
| N | F | F | Y | Y | K | N | F | G | S |
| N | F | F | Y | Y | K | N | F | G | I |
| N | F | F | Y | Y | R | K | Y | S | S |
| N | F | F | Y | Y | R | K | Y | S | I |
| N | F | F | Y | Y | R | K | Y | G | S |
| N | F | F | Y | Y | R | K | Y | G | I |
| N | F | F | Y | Y | R | K | F | S | S |
| N | F | F | Y | Y | R | K | F | S | I |
| N | F | F | Y | Y | R | K | F | G | S |
| N | F | F | Y | Y | R | K | F | G | I |
| N | F | F | Y | Y | R | N | Y | S | S |
| N | F | F | Y | Y | R | N | Y | S | I |
| N | F | F | Y | Y | R | N | Y | G | S |
| N | F | F | Y | Y | R | N | Y | G | I |
| N | F | F | Y | Y | R | N | F | S | S |
| N | F | F | Y | Y | R | N | F | S | I |
| N | F | F | Y | Y | R | N | F | G | S |
| N | F | F | Y | Y | R | N | F | G | I |
| N | F | F | R | C | K | K | Y | S | S |
| N | F | F | R | C | K | K | Y | S | I |
| N | F | F | R | C | K | K | Y | G | S |
| N | F | F | R | C | K | K | Y | G | I |
| N | F | F | R | C | K | K | F | S | S |
| N | F | F | R | C | K | K | F | S | I |
| N | F | F | R | C | K | K | F | G | S |
| N | F | F | R | C | K | K | F | G | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | F | F | R | C | K | N | Y | S | S |
| N | F | F | R | C | K | N | Y | S | I |
| N | F | F | R | C | K | N | Y | G | S |
| N | F | F | R | C | K | N | Y | G | I |
| N | F | F | R | C | K | N | F | S | S |
| N | F | F | R | C | K | N | F | S | I |
| N | F | F | R | C | K | N | F | G | S |
| N | F | F | R | C | K | N | F | G | I |
| N | F | F | R | C | R | K | Y | S | S |
| N | F | F | R | C | R | K | Y | S | I |
| N | F | F | R | C | R | K | Y | G | S |
| N | F | F | R | C | R | K | Y | G | I |
| N | F | F | R | C | R | K | F | S | S |
| N | F | F | R | C | R | K | F | S | I |
| N | F | F | R | C | R | K | F | G | S |
| N | F | F | R | C | R | K | F | G | I |
| N | F | F | R | C | R | N | Y | S | S |
| N | F | F | R | C | R | N | Y | S | I |
| N | F | F | R | C | R | N | Y | G | S |
| N | F | F | R | C | R | N | Y | G | I |
| N | F | F | R | C | R | N | F | S | S |
| N | F | F | R | C | R | N | F | S | I |
| N | F | F | R | C | R | N | F | G | S |
| N | F | F | R | C | R | N | F | G | I |
| N | F | F | R | Y | K | K | Y | S | S |
| N | F | F | R | Y | K | K | Y | S | I |
| N | F | F | R | Y | K | K | Y | G | S |
| N | F | F | R | Y | K | K | Y | G | I |
| N | F | F | R | Y | K | K | F | S | S |
| N | F | F | R | Y | K | K | F | S | I |
| N | F | F | R | Y | K | K | F | G | S |
| N | F | F | R | Y | K | K | F | G | I |
| N | F | F | R | Y | K | N | Y | S | S |
| N | F | F | R | Y | K | N | Y | S | I |
| N | F | F | R | Y | K | N | Y | G | S |
| N | F | F | R | Y | K | N | Y | G | I |
| N | F | F | R | Y | K | N | F | S | S |
| N | F | F | R | Y | K | N | F | S | I |
| N | F | F | R | Y | K | N | F | G | S |
| N | F | F | R | Y | K | N | F | G | I |
| N | F | F | R | Y | R | K | Y | S | S |
| N | F | F | R | Y | R | K | Y | S | I |
| N | F | F | R | Y | R | K | Y | G | S |
| N | F | F | R | Y | R | K | Y | G | I |
| N | F | F | R | Y | R | K | F | S | S |
| N | F | F | R | Y | R | K | F | G | S |
| N | F | F | R | Y | R | K | F | G | I |
| N | F | F | R | Y | R | N | Y | S | S |
| N | F | F | R | Y | R | N | Y | S | I |
| N | F | F | R | Y | R | N | Y | G | S |
| N | F | F | R | Y | R | N | Y | G | I |
| N | F | F | R | Y | R | N | F | S | S |
| N | F | F | R | Y | R | N | F | S | I |
| N | F | F | R | Y | R | N | F | G | S |
| N | F | F | R | Y | R | N | F | G | I |
| T | V | L | Y | C | K | K | Y | S | S |
| T | V | L | Y | C | K | K | Y | S | I |
| T | V | L | Y | C | K | K | Y | G | S |
| T | V | L | Y | C | K | K | Y | G | I |
| T | V | L | Y | C | K | K | F | S | S |
| T | V | L | Y | C | K | K | F | S | I |
| T | V | L | Y | C | K | K | F | G | S |
| T | V | L | Y | C | K | K | F | G | I |
| T | V | L | Y | C | K | N | Y | S | S |
| T | V | L | Y | C | K | N | Y | S | I |
| T | V | L | Y | C | K | N | Y | G | S |
| T | V | L | Y | C | K | N | Y | G | I |
| T | V | L | Y | C | K | N | F | S | S |
| T | V | L | Y | C | K | N | F | G | S |
| T | V | L | Y | C | K | N | F | G | I |
| T | V | L | Y | C | R | K | Y | S | S |
| T | V | L | Y | C | R | K | Y | S | I |
| T | V | L | Y | C | R | K | Y | G | S |
| T | V | L | Y | C | R | K | Y | G | I |
| T | V | L | Y | C | R | K | F | S | S |
| T | V | L | Y | C | R | K | F | S | I |
| T | V | L | Y | C | R | K | F | G | S |
| T | V | L | Y | C | R | K | F | G | I |
| T | V | L | Y | C | R | N | Y | S | S |
| T | V | L | Y | C | R | N | Y | S | I |
| T | V | L | Y | C | R | N | Y | G | S |
| T | V | L | Y | C | R | N | Y | G | I |
| T | V | L | Y | C | R | N | F | S | S |
| T | V | L | Y | C | R | N | F | S | I |
| T | V | L | Y | C | R | N | F | G | S |
| T | V | L | Y | C | R | N | F | G | I |
| T | V | L | Y | Y | K | K | Y | S | S |
| T | V | L | Y | Y | K | K | Y | S | I |
| T | V | L | Y | Y | K | K | Y | G | S |
| T | V | L | Y | Y | K | K | Y | G | I |
| T | V | L | Y | Y | K | K | F | S | S |
| T | V | L | Y | Y | K | K | F | S | I |
| T | V | L | Y | Y | K | K | F | G | S |
| T | V | L | Y | Y | K | K | F | G | I |
| T | V | L | Y | Y | K | N | Y | S | S |
| T | V | L | Y | Y | K | N | Y | S | I |
| T | V | L | Y | Y | K | N | Y | G | S |
| T | V | L | Y | Y | K | N | Y | G | I |
| T | V | L | Y | Y | K | N | F | S | S |
| T | V | L | Y | Y | K | N | F | S | I |
| T | V | L | Y | Y | K | N | F | G | S |
| T | V | L | Y | Y | K | N | F | G | I |
| T | V | L | Y | Y | R | K | Y | S | S |
| T | V | L | Y | Y | R | K | Y | S | I |
| T | V | L | Y | Y | R | K | Y | G | S |
| T | V | L | Y | Y | R | K | Y | G | I |
| T | V | L | Y | Y | R | K | F | S | S |
| T | V | L | Y | Y | R | K | F | S | I |
| T | V | L | Y | Y | R | K | F | G | S |
| T | V | L | Y | Y | R | K | F | G | I |
| T | V | L | Y | Y | R | N | Y | S | S |
| T | V | L | Y | Y | R | N | Y | S | I |
| T | V | L | Y | Y | R | N | Y | G | S |
| T | V | L | Y | Y | R | N | Y | G | I |
| T | V | L | Y | Y | R | N | F | S | S |
| T | V | L | Y | Y | R | N | F | S | I |
| T | V | L | Y | Y | R | N | F | G | S |
| T | V | L | Y | Y | R | N | F | G | I |
| T | V | L | R | C | K | K | Y | S | S |
| T | V | L | R | C | K | K | Y | S | I |
| T | V | L | R | C | K | K | Y | G | S |
| T | V | L | R | C | K | K | Y | G | I |
| T | V | L | R | C | K | K | F | S | S |
| T | V | L | R | C | K | K | F | S | I |
| T | V | L | R | C | K | K | F | G | S |
| T | V | L | R | C | K | K | F | G | I |
| T | V | L | R | C | K | N | Y | S | S |
| T | V | L | R | C | K | N | Y | S | I |
| T | V | L | R | C | K | N | Y | G | S |
| T | V | L | R | C | K | N | Y | G | I |
| T | V | L | R | C | K | N | F | S | S |
| T | V | L | R | C | K | N | F | S | I |
| T | V | L | R | C | K | N | F | G | S |
| T | V | L | R | C | K | N | F | G | I |
| T | V | L | R | C | R | K | Y | S | S |
| T | V | L | R | C | R | K | Y | S | I |
| T | V | L | R | C | R | K | Y | G | S |
| T | V | L | R | C | R | K | Y | G | I |
| T | V | L | R | C | R | K | F | S | S |
| T | V | L | R | C | R | K | F | S | I |
| T | V | L | R | C | R | K | F | G | S |
| T | V | L | R | C | R | K | F | G | I |
| T | V | L | R | C | R | N | Y | S | S |
| T | V | L | R | C | R | N | Y | S | I |
| T | V | L | R | C | R | N | Y | G | S |
| T | V | L | R | C | R | N | Y | G | I |
| T | V | L | R | C | R | N | F | S | S |
| T | V | L | R | C | R | N | F | S | I |

TABLE 6-continued

Exemplary Mutations of 1.140 (SEQ ID NO: 8) Light Chain to Germline at

TABLE 6-continued

Exemplary Mutations of 1.140 (SEQ ID NO: 8) Light

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| T | F | F | Y | C | K | N | Y | G | S |
| T | F | F | Y | C | K | N | Y | G | I |
| T | F | F | Y | C | K | N | F | S | S |
| T | F | F | Y | C | K | N | F | S | I |
| T | F | F | Y | C | K | N | F | G | S |
| T | F | F | Y | C | K | N | F | G | I |
| T | F | F | Y | C | R | K | Y | S | S |
| T | F | F | Y | C | R | K | Y | S | I |
| T | F | F | Y | C | R | K | Y | G | S |
| T | F | F | Y | C | R | K | Y | G | I |
| T | F | F | Y | C | R | K | F | S | S |
| T | F | F | Y | C | R | K | F | S | I |
| T | F | F | Y | C | R | K | F | G | S |
| T | F | F | Y | C | R | K | F | G | I |
| T | F | F | Y | C | R | N | Y | S | S |
| T | F | F | Y | C | R | N | Y | S | I |
| T | F | F | Y | C | R | N | Y | G | S |
| T | F | F | Y | C | R | N | Y | G | I |
| T | F | F | Y | C | R | N | F | S | S |
| T | F | F | Y | C | R | N | F | S | I |
| T | F | F | Y | C | R | N | F | G | S |
| T | F | F | Y | C | R | N | F | G | I |
| T | F | F | Y | Y | K | K | Y | S | S |
| T | F | F | Y | Y | K | K | Y | S | I |
| T | F | F | Y | Y | K | K | Y | G | S |
| T | F | F | Y | Y | K | K | Y | G | I |
| T | F | F | Y | Y | K | K | F | S | S |
| T | F | F | Y | Y | K | K | F | S | I |
| T | F | F | Y | Y | K | K | F | G | S |
| T | F | F | Y | Y | K | K | F | G | I |
| T | F | F | Y | Y | K | N | Y | S | S |
| T | F | F | Y | Y | K | N | Y | S | I |
| T | F | F | Y | Y | K | N | Y | G | S |
| T | F | F | Y | Y | K | N | Y | G | I |
| T | F | F | Y | Y | K | N | F | S | S |
| T | F | F | Y | Y | K | N | F | S | I |
| T | F | F | Y | Y | K | N | F | G | S |
| T | F | F | Y | Y | K | N | F | G | I |
| T | F | F | Y | Y | R | K | Y | S | S |
| T | F | F | Y | Y | R | K | Y | S | I |
| T | F | F | Y | Y | R | K | Y | G | S |
| T | F | F | Y | Y | R | K | Y | G | I |
| T | F | F | Y | Y | R | K | F | S | S |
| T | F | F | Y | Y | R | K | F | S | I |
| T | F | F | Y | Y | R | K | F | G | S |
| T | F | F | Y | Y | R | K | F | G | I |
| T | F | F | Y | Y | R | N | Y | S | S |
| T | F | F | Y | Y | R | N | Y | S | I |
| T | F | F | Y | Y | R | N | Y | G | S |
| T | F | F | Y | Y | R | N | Y | G | I |
| T | F | F | Y | Y | R | N | F | S | S |
| T | F | F | Y | Y | R | N | F | S | I |
| T | F | F | Y | Y | R | N | F | G | S |
| T | F | F | Y | Y | R | N | F | G | I |
| T | F | F | R | C | K | K | Y | S | S |
| T | F | F | R | C | K | K | Y | S | I |
| T | F | F | R | C | K | K | Y | G | S |
| T | F | F | R | C | K | K | Y | G | I |
| T | F | F | R | C | K | K | F | S | S |
| T | F | F | R | C | K | K | F | S | I |
| T | F | F | R | C | K | K | F | G | S |
| T | F | F | R | C | K | K | F | G | I |
| T | F | F | R | C | K | N | Y | S | S |
| T | F | F | R | C | K | N | Y | S | I |
| T | F | F | R | C | K | N | Y | G | S |
| T | F | F | R | C | K | N | Y | G | I |
| T | F | F | R | C | K | N | F | S | S |
| T | F | F | R | C | K | N | F | S | I |
| T | F | F | R | C | K | N | F | G | S |
| T | F | F | R | C | K | N | F | G | I |
| T | F | F | R | C | R | K | Y | S | S |
| T | F | F | R | C | R | K | Y | S | I |
| T | F | F | R | C | R | K | Y | G | S |
| T | F | F | R | C | R | K | Y | G | I |
| T | F | F | R | C | R | K | F | S | S |
| T | F | F | R | C | R | K | F | G | S |
| T | F | F | R | C | R | K | F | G | I |
| T | F | F | R | C | R | N | Y | S | S |
| T | F | F | R | C | R | N | Y | S | I |
| T | F | F | R | C | R | N | Y | G | S |
| T | F | F | R | C | R | N | Y | G | I |
| T | F | F | R | C | R | N | F | S | S |
| T | F | F | R | C | R | N | F | S | I |
| T | F | F | R | C | R | N | F | G | S |
| T | F | F | R | C | R | N | F | G | I |
| T | F | F | R | Y | K | K | Y | S | S |
| T | F | F | R | Y | K | K | Y | S | I |
| T | F | F | R | Y | K | K | Y | G | S |
| T | F | F | R | Y | K | K | Y | G | I |
| T | F | F | R | Y | K | K | F | S | S |
| T | F | F | R | Y | K | K | F | S | I |
| T | F | F | R | Y | K | K | F | G | S |
| T | F | F | R | Y | K | K | F | G | I |
| T | F | F | R | Y | K | N | Y | S | S |
| T | F | F | R | Y | K | N | Y | S | I |
| T | F | F | R | Y | K | N | Y | G | S |
| T | F | F | R | Y | K | N | Y | G | I |
| T | F | F | R | Y | K | N | F | S | S |
| T | F | F | R | Y | K | N | F | S | I |
| T | F | F | R | Y | K | N | F | G | S |
| T | F | F | R | Y | K | N | F | G | I |
| T | F | F | R | Y | R | K | Y | S | S |
| T | F | F | R | Y | R | K | Y | S | I |
| T | F | F | R | Y | R | K | Y | G | S |
| T | F | F | R | Y | R | K | Y | G | I |
| T | F | F | R | Y | R | K | F | S | S |
| T | F | F | R | Y | R | K | F | S | I |
| T | F | F | R | Y | R | K | F | G | S |
| T | F | F | R | Y | R | K | F | G | I |
| T | F | F | R | Y | R | N | Y | S | S |
| T | F | F | R | Y | R | N | Y | S | I |
| T | F | F | R | Y | R | N | Y | G | S |
| T | F | F | R | Y | R | N | Y | G | I |
| T | F | F | R | Y | R | N | F | S | S |
| T | F | F | R | Y | R | N | F | S | I |
| T | F | F | R | Y | R | N | F | G | S |
| T | F | F | R | Y | R | N | F | G | I |
| N | V | L | Y | C | K | K | Y | S | S |
| N | V | L | Y | C | K | K | Y | S | I |
| N | V | L | Y | C | K | K | Y | G | S |
| N | V | L | Y | C | K | K | Y | G | I |
| N | V | L | Y | C | K | K | F | S | S |
| N | V | L | Y | C | K | K | F | S | I |
| N | V | L | Y | C | K | K | F | G | S |
| N | V | L | Y | C | K | K | F | G | I |
| N | V | L | Y | C | K | N | Y | S | S |
| N | V | L | Y | C | K | N | Y | S | I |
| N | V | L | Y | C | K | N | Y | G | S |
| N | V | L | Y | C | K | N | Y | G | I |
| N | V | L | Y | C | K | N | F | S | S |
| N | V | L | Y | C | K | N | F | S | I |
| N | V | L | Y | C | K | N | F | G | S |
| N | V | L | Y | C | K | N | F | G | I |
| N | V | L | Y | C | R | K | Y | S | S |
| N | V | L | Y | C | R | K | Y | S | I |
| N | V | L | Y | C | R | K | Y | G | S |
| N | V | L | Y | C | R | K | Y | G | I |
| N | V | L | Y | C | R | K | F | S | S |
| N | V | L | Y | C | R | K | F | S | I |
| N | V | L | Y | C | R | K | F | G | S |
| N | V | L | Y | C | R | K | F | G | I |
| N | V | L | Y | C | R | N | Y | S | S |
| N | V | L | Y | C | R | N | Y | S | I |
| N | V | L | Y | C | R | N | Y | G | S |
| N | V | L | Y | C | R | N | Y | G | I |
| N | V | L | Y | C | R | N | F | S | S |
| N | V | L | Y | C | R | N | F | S | I |
| N | V | L | Y | C | R | N | F | G | S |
| N | V | L | Y | C | R | N | F | G | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | V | L | Y | Y | K | K | Y | S | S |
| N | V | L | Y | Y | K | K | Y | S | I |
| N | V | L | Y | Y | K | K | Y | G | S |
| N | V | L | Y | Y | K | K | Y | G | I |
| N | V | L | Y | Y | K | K | F | S | S |
| N | V | L | Y | Y | K | K | F | S | I |
| N | V | L | Y | Y | K | K | F | G | S |
| N | V | L | Y | Y | K | K | F | G | I |
| N | V | L | Y | Y | K | N | Y | S | S |
| N | V | L | Y | Y | K | N | Y | S | I |
| N | V | L | Y | Y | K | N | Y | G | S |
| N | V | L | Y | Y | K | N | Y | G | I |
| N | V | L | Y | Y | K | N | F | S | S |
| N | V | L | Y | Y | K | N | F | S | I |
| N | V | L | Y | Y | K | N | F | G | S |
| N | V | L | Y | Y | K | N | F | G | I |
| N | V | L | Y | Y | R | K | Y | S | S |
| N | V | L | Y | Y | R | K | Y | S | I |
| N | V | L | Y | Y | R | K | Y | G | S |
| N | V | L | Y | Y | R | K | Y | G | I |
| N | V | L | Y | Y | R | K | F | S | S |
| N | V | L | Y | Y | R | K | F | S | I |
| N | V | L | Y | Y | R | K | F | G | S |
| N | V | L | Y | Y | R | K | F | G | I |
| N | V | L | Y | Y | R | N | Y | S | S |
| N | V | L | Y | Y | R | N | Y | S | I |
| N | V | L | Y | Y | R | N | Y | G | S |
| N | V | L | Y | Y | R | N | Y | G | I |
| N | V | L | Y | Y | R | N | F | S | S |
| N | V | L | Y | Y | R | N | F | S | I |
| N | V | L | Y | Y | R | N | F | G | S |
| N | V | L | Y | Y | R | N | F | G | I |
| N | V | L | R | C | K | K | Y | S | S |
| N | V | L | R | C | K | K | Y | S | I |
| N | V | L | R | C | K | K | Y | G | S |
| N | V | L | R | C | K | K | Y | G | I |
| N | V | L | R | C | K | K | F | S | S |
| N | V | L | R | C | K | K | F | S | I |
| N | V | L | R | C | K | K | F | G | S |
| N | V | L | R | C | K | K | F | G | I |
| N | V | L | R | C | K | N | Y | S | S |
| N | V | L | R | C | K | N | Y | S | I |
| N | V | L | R | C | K | N | Y | G | S |
| N | V | L | R | C | K | N | Y | G | I |
| N | V | L | R | C | K | N | F | S | S |
| N | V | L | R | C | K | N | F | S | I |
| N | V | L | R | C | K | N | F | G | S |
| N | V | L | R | C | K | N | F | G | I |
| N | V | L | R | C | R | K | Y | S | S |
| N | V | L | R | C | R | K | Y | S | I |
| N | V | L | R | C | R | K | Y | G | S |
| N | V | L | R | C | R | K | Y | G | I |
| N | V | L | R | C | R | K | F | S | S |
| N | V | L | R | C | R | K | F | S | I |
| N | V | L | R | C | R | K | F | G | S |
| N | V | L | R | C | R | K | F | G | I |
| N | V | L | R | C | R | N | Y | S | S |
| N | V | L | R | C | R | N | Y | S | I |
| N | V | L | R | C | R | N | Y | G | S |
| N | V | L | R | C | R | N | Y | G | I |
| N | V | L | R | C | R | N | F | S | S |
| N | V | L | R | C | R | N | F | S | I |
| N | V | L | R | C | R | N | F | G | S |
| N | V | L | R | C | R | N | F | G | I |
| N | V | L | R | Y | K | K | Y | S | S |
| N | V | L | R | Y | K | K | Y | S | I |
| N | V | L | R | Y | K | K | Y | G | S |
| N | V | L | R | Y | K | K | Y | G | I |
| N | V | L | R | Y | K | K | F | S | S |
| N | V | L | R | Y | K | K | F | S | I |
| N | V | L | R | Y | K | K | F | G | S |
| N | V | L | R | Y | K | K | F | G | I |
| N | V | L | R | Y | K | N | Y | S | S |
| N | V | L | R | Y | K | N | Y | S | I |
| N | V | L | R | Y | K | N | Y | G | S |
| N | V | L | R | Y | K | N | Y | G | I |
| N | V | L | R | Y | K | N | F | S | S |
| N | V | L | R | Y | K | N | F | S | I |
| N | V | L | R | Y | K | N | F | G | S |
| N | V | L | R | Y | K | N | F | G | I |
| N | V | L | R | Y | R | K | Y | S | S |
| N | V | L | R | Y | R | K | Y | S | I |
| N | V | L | R | Y | R | K | Y | G | S |
| N | V | L | R | Y | R | K | Y | G | I |
| N | V | L | R | Y | R | K | F | S | S |
| N | V | L | R | Y | R | K | F | S | I |
| N | V | L | R | Y | R | K | F | G | S |
| N | V | L | R | Y | R | K | F | G | I |
| N | V | L | R | Y | R | N | Y | S | S |
| N | V | L | R | Y | R | N | Y | S | I |
| N | V | L | R | Y | R | N | Y | G | S |
| N | V | L | R | Y | R | N | Y | G | I |
| N | V | L | R | Y | R | N | F | S | S |
| N | V | L | R | Y | R | N | F | S | I |
| N | V | L | R | Y | R | N | F | G | S |
| N | V | L | R | Y | R | N | F | G | I |
| N | V | F | Y | C | K | K | Y | S | S |
| N | V | F | Y | C | K | K | Y | S | I |
| N | V | F | Y | C | K | K | Y | G | S |
| N | V | F | Y | C | K | K | Y | G | I |
| N | V | F | Y | C | K | K | F | S | S |
| N | V | F | Y | C | K | K | F | S | I |
| N | V | F | Y | C | K | K | F | G | S |
| N | V | F | Y | C | K | K | F | G | I |
| N | V | F | Y | C | K | N | Y | S | S |
| N | V | F | Y | C | K | N | Y | S | I |
| N | V | F | Y | C | K | N | Y | G | S |
| N | V | F | Y | C | K | N | Y | G | I |
| N | V | F | Y | C | K | N | F | S | S |
| N | V | F | Y | C | K | N | F | S | I |
| N | V | F | Y | C | K | N | F | G | S |
| N | V | F | Y | C | K | N | F | G | I |
| N | V | F | Y | C | R | K | Y | S | S |
| N | V | F | Y | C | R | K | Y | S | I |
| N | V | F | Y | C | R | K | Y | G | S |
| N | V | F | Y | C | R | K | Y | G | I |
| N | V | F | Y | C | R | K | F | S | S |
| N | V | F | Y | C | R | K | F | S | I |
| N | V | F | Y | C | R | K | F | G | S |
| N | V | F | Y | C | R | K | F | G | I |
| N | V | F | Y | C | R | N | Y | S | S |
| N | V | F | Y | C | R | N | Y | S | I |
| N | V | F | Y | C | R | N | Y | G | S |
| N | V | F | Y | C | R | N | Y | G | I |
| N | V | F | Y | C | R | N | F | S | S |
| N | V | F | Y | C | R | N | F | S | I |
| N | V | F | Y | C | R | N | F | G | S |
| N | V | F | Y | C | R | N | F | G | I |
| N | V | F | Y | Y | K | K | Y | S | S |
| N | V | F | Y | Y | K | K | Y | S | I |
| N | V | F | Y | Y | K | K | Y | G | S |
| N | V | F | Y | Y | K | K | Y | G | I |
| N | V | F | Y | Y | K | K | F | S | S |
| N | V | F | Y | Y | K | K | F | G | S |
| N | V | F | Y | Y | K | K | F | G | I |
| N | V | F | Y | Y | K | N | Y | S | S |
| N | V | F | Y | Y | K | N | Y | S | I |
| N | V | F | Y | Y | K | N | Y | G | S |
| N | V | F | Y | Y | K | N | Y | G | I |
| N | V | F | Y | Y | K | N | F | S | S |
| N | V | F | Y | Y | K | N | F | S | I |
| N | V | F | Y | Y | K | N | F | G | S |
| N | V | F | Y | Y | K | N | F | G | I |
| N | V | F | Y | Y | R | K | Y | S | S |
| N | V | F | Y | Y | R | K | Y | S | I |
| N | V | F | Y | Y | R | K | Y | G | S |
| N | V | F | Y | Y | R | K | Y | G | I |
| N | V | F | Y | Y | R | K | F | S | S |
| N | V | F | Y | Y | R | K | F | S | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | V | F | Y | Y | R | K | F | G | S |
| N | V | F | Y | Y | R | K | F | G | I |
| N | V | F | Y | Y | R | N | Y | S | S |
| N | V | F | Y | Y | R | N | Y | S | I |
| N | V | F | Y | Y | R | N | Y | G | S |
| N | V | F | Y | Y | R | N | Y | G | I |
| N | V | F | Y | Y | R | N | F | S | S |
| N | V | F | Y | Y | R | N | F | S | I |
| N | V | F | Y | Y | R | N | F | G | S |
| N | V | F | Y | Y | R | N | F | G | I |
| N | V | F | R | C | K | K | Y | S | S |
| N | V | F | R | C | K | K | Y | S | I |
| N | V | F | R | C | K | K | Y | G | S |
| N | V | F | R | C | K | K | Y | G | I |
| N | V | F | R | C | K | K | F | S | S |
| N | V | F | R | C | K | K | F | S | I |
| N | V | F | R | C | K | K | F | G | S |
| N | V | F | R | C | K | K | F | G | I |
| N | V | F | R | C | K | N | Y | S | S |
| N | V | F | R | C | K | N | Y | S | I |
| N | V | F | R | C | K | N | Y | G | S |
| N | V | F | R | C | K | N | Y | G | I |
| N | V | F | R | C | K | N | F | S | S |
| N | V | F | R | C | K | N | F | S | I |
| N | V | F | R | C | K | N | F | G | S |
| N | V | F | R | C | K | N | F | G | I |
| N | V | F | R | C | R | K | Y | S | S |
| N | V | F | R | C | R | K | Y | S | I |
| N | V | F | R | C | R | K | Y | G | S |
| N | V | F | R | C | R | K | Y | G | I |
| N | V | F | R | C | R | K | F | S | S |
| N | V | F | R | C | R | K | F | S | I |
| N | V | F | R | C | R | K | F | G | S |
| N | V | F | R | C | R | K | F | G | I |
| N | V | F | R | C | R | N | Y | S | S |
| N | V | F | R | C | R | N | Y | S | I |
| N | V | F | R | C | R | N | Y | G | S |
| N | V | F | R | C | R | N | Y | G | I |
| N | V | F | R | C | R | N | F | S | S |
| N | V | F | R | C | R | N | F | S | I |
| N | V | F | R | C | R | N | F | G | S |
| N | V | F | R | C | R | N | F | G | I |
| N | V | F | R | Y | K | K | Y | S | S |
| N | V | F | R | Y | K | K | Y | S | I |
| N | V | F | R | Y | K | K | Y | G | S |
| N | V | F | R | Y | K | K | Y | G | I |
| N | V | F | R | Y | K | K | F | S | S |
| N | V | F | R | Y | K | K | F | S | I |
| N | V | F | R | Y | K | K | F | G | S |
| N | V | F | R | Y | K | K | F | G | I |
| N | V | F | R | Y | K | N | Y | S | S |
| N | V | F | R | Y | K | N | Y | S | I |
| N | V | F | R | Y | K | N | Y | G | S |
| N | V | F | R | Y | K | N | Y | G | I |
| N | V | F | R | Y | K | N | F | S | S |
| N | V | F | R | Y | K | N | F | S | I |
| N | V | F | R | Y | K | N | F | G | S |
| N | V | F | R | Y | K | N | F | G | I |
| N | V | F | R | Y | R | K | Y | S | S |
| N | V | F | R | Y | R | K | Y | S | I |
| N | V | F | R | Y | R | K | Y | G | S |
| N | V | F | R | Y | R | K | Y | G | I |
| N | V | F | R | Y | R | K | F | S | S |
| N | V | F | R | Y | R | K | F | S | I |
| N | V | F | R | Y | R | K | F | G | S |
| N | V | F | R | Y | R | K | F | G | I |
| N | V | F | R | Y | R | N | Y | S | S |
| N | V | F | R | Y | R | N | Y | S | I |
| N | V | F | R | Y | R | N | Y | G | S |
| N | V | F | R | Y | R | N | Y | G | I |
| N | V | F | R | Y | R | N | F | S | S |
| N | V | F | R | Y | R | N | F | S | I |
| N | V | F | R | Y | R | N | F | G | S |
| N | V | F | R | Y | R | N | F | G | I |
| N | F | L | Y | C | K | K | Y | S | S |
| N | F | L | Y | C | K | K | Y | S | I |
| N | F | L | Y | C | K | K | Y | G | S |
| N | F | L | Y | C | K | K | Y | G | I |
| N | F | L | Y | C | K | K | F | S | S |
| N | F | L | Y | C | K | K | F | S | I |
| N | F | L | Y | C | K | K | F | G | S |
| N | F | L | Y | C | K | K | F | G | I |
| N | F | L | Y | C | K | N | Y | S | S |
| N | F | L | Y | C | K | N | Y | S | I |
| N | F | L | Y | C | K | N | Y | G | S |
| N | F | L | Y | C | K | N | Y | G | I |
| N | F | L | Y | C | K | N | F | S | S |
| N | F | L | Y | C | K | N | F | S | I |
| N | F | L | Y | C | K | N | F | G | S |
| N | F | L | Y | C | K | N | F | G | I |
| N | F | L | Y | C | R | K | Y | S | S |
| N | F | L | Y | C | R | K | Y | S | I |
| N | F | L | Y | C | R | K | Y | G | S |
| N | F | L | Y | C | R | K | Y | G | I |
| N | F | L | Y | C | R | K | F | S | S |
| N | F | L | Y | C | R | K | F | S | I |
| N | F | L | Y | C | R | K | F | G | S |
| N | F | L | Y | C | R | K | F | G | I |
| N | F | L | Y | C | R | N | Y | S | S |
| N | F | L | Y | C | R | N | Y | S | I |
| N | F | L | Y | C | R | N | Y | G | S |
| N | F | L | Y | C | R | N | Y | G | I |
| N | F | L | Y | C | R | N | F | S | S |
| N | F | L | Y | C | R | N | F | S | I |
| N | F | L | Y | C | R | N | F | G | S |
| N | F | L | Y | C | R | N | F | G | I |
| N | F | L | Y | Y | K | K | Y | S | S |
| N | F | L | Y | Y | K | K | Y | S | I |
| N | F | L | Y | Y | K | K | Y | G | S |
| N | F | L | Y | Y | K | K | Y | G | I |
| N | F | L | Y | Y | K | K | F | S | S |
| N | F | L | Y | Y | K | K | F | S | I |
| N | F | L | Y | Y | K | K | F | G | S |
| N | F | L | Y | Y | K | K | F | G | I |
| N | F | L | Y | Y | K | N | Y | S | S |
| N | F | L | Y | Y | K | N | Y | S | I |
| N | F | L | Y | Y | K | N | Y | G | S |
| N | F | L | Y | Y | K | N | Y | G | I |
| N | F | L | Y | Y | K | N | F | S | S |
| N | F | L | Y | Y | K | N | F | S | I |
| N | F | L | Y | Y | K | N | F | G | S |
| N | F | L | Y | Y | K | N | F | G | I |
| N | F | L | Y | Y | R | K | Y | S | S |
| N | F | L | Y | Y | R | K | Y | S | I |
| N | F | L | Y | Y | R | K | Y | G | S |
| N | F | L | Y | Y | R | K | Y | G | I |
| N | F | L | Y | Y | R | K | F | S | S |
| N | F | L | Y | Y | R | K | F | S | I |
| N | F | L | Y | Y | R | K | F | G | S |
| N | F | L | Y | Y | R | K | F | G | I |
| N | F | L | Y | Y | R | N | Y | S | S |
| N | F | L | Y | Y | R | N | Y | S | I |
| N | F | L | Y | Y | R | N | Y | G | S |
| N | F | L | Y | Y | R | N | Y | G | I |
| N | F | L | Y | Y | R | N | F | S | S |
| N | F | L | Y | Y | R | N | F | S | I |
| N | F | L | Y | Y | R | N | F | G | S |
| N | F | L | Y | Y | R | N | F | G | I |
| N | F | L | R | C | K | K | Y | S | S |
| N | F | L | R | C | K | K | Y | S | I |
| N | F | L | R | C | K | K | Y | G | S |
| N | F | L | R | C | K | K | Y | G | I |
| N | F | L | R | C | K | K | F | S | S |
| N | F | L | R | C | K | K | F | S | I |
| N | F | L | R | C | K | K | F | G | S |
| N | F | L | R | C | K | K | F | G | I |
| N | F | L | R | C | K | N | Y | S | S |
| N | F | L | R | C | K | N | Y | S | I |
| N | F | L | R | C | K | N | Y | G | S |
| N | F | L | R | C | K | N | Y | G | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | F | L | R | C | K | N | F | S | S |
| N | F | L | R | C | K | N | F | S | I |
| N | F | L | R | C | K | N | F | G | S |
| N | F | L | R | C | K | N | F | G | I |
| N | F | L | R | C | R | K | Y | S | S |
| N | F | L | R | C | R | K | Y | S | I |
| N | F | L | R | C | R | K | Y | G | S |
| N | F | L | R | C | R | K | Y | G | I |
| N | F | L | R | C | R | K | F | S | S |
| N | F | L | R | C | R | K | F | S | I |
| N | F | L | R | C | R | K | F | G | S |
| N | F | L | R | C | R | K | F | G | I |
| N | F | L | R | C | R | N | Y | S | S |
| N | F | L | R | C | R | N | Y | S | I |
| N | F | L | R | C | R | N | Y | G | S |
| N | F | L | R | C | R | N | Y | G | I |
| N | F | L | R | C | R | N | F | S | S |
| N | F | L | R | C | R | N | F | S | I |
| N | F | L | R | C | R | N | F | G | S |
| N | F | L | R | C | R | N | F | G | I |
| N | F | L | R | Y | K | K | Y | S | S |
| N | F | L | R | Y | K | K | Y | S | I |
| N | F | L | R | Y | K | K | Y | G | S |
| N | F | L | R | Y | K | K | Y | G | I |
| N | F | L | R | Y | K | K | F | S | S |
| N | F | L | R | Y | K | K | F | S | I |
| N | F | L | R | Y | K | K | F | G | S |
| N | F | L | R | Y | K | K | F | G | I |
| N | F | L | R | Y | K | N | Y | S | S |
| N | F | L | R | Y | K | N | Y | S | I |
| N | F | L | R | Y | K | N | Y | G | S |
| N | F | L | R | Y | K | N | Y | G | I |
| N | F | L | R | Y | K | N | F | S | S |
| N | F | L | R | Y | K | N | F | S | I |
| N | F | L | R | Y | K | N | F | G | S |
| N | F | L | R | Y | K | N | F | G | I |
| N | F | L | R | Y | R | K | Y | S | S |
| N | F | L | R | Y | R | K | Y | S | I |
| N | F | L | R | Y | R | K | Y | G | S |
| N | F | L | R | Y | R | K | Y | G | I |
| N | F | L | R | Y | R | K | F | S | S |
| N | F | L | R | Y | R | K | F | S | I |
| N | F | L | R | Y | R | K | F | G | S |
| N | F | L | R | Y | R | K | F | G | I |
| N | F | L | R | Y | R | N | Y | S | S |
| N | F | L | R | Y | R | N | Y | S | I |
| N | F | L | R | Y | R | N | Y | G | S |
| N | F | L | R | Y | R | N | Y | G | I |
| N | F | L | R | Y | R | N | F | S | S |
| N | F | L | R | Y | R | N | F | S | I |
| N | F | L | R | Y | R | N | F | G | S |
| N | F | L | R | Y | R | N | F | G | I |
| N | F | F | Y | C | K | K | Y | S | S |
| N | F | F | Y | C | K | K | Y | S | I |
| N | F | F | Y | C | K | K | Y | G | S |
| N | F | F | Y | C | K | K | Y | G | I |
| N | F | F | Y | C | K | K | F | S | S |
| N | F | F | Y | C | K | K | F | S | I |
| N | F | F | Y | C | K | K | F | G | S |
| N | F | F | Y | C | K | K | F | G | I |
| N | F | F | Y | C | K | N | Y | S | S |
| N | F | F | Y | C | K | N | Y | S | I |
| N | F | F | Y | C | K | N | Y | G | S |
| N | F | F | Y | C | K | N | Y | G | I |
| N | F | F | Y | C | K | N | F | S | S |
| N | F | F | Y | C | K | N | F | S | I |
| N | F | F | Y | C | K | N | F | G | S |
| N | F | F | Y | C | K | N | F | G | I |
| N | F | F | Y | C | R | K | Y | S | S |
| N | F | F | Y | C | R | K | Y | S | I |
| N | F | F | Y | C | R | K | Y | G | S |
| N | F | F | Y | C | R | K | Y | G | I |
| N | F | F | Y | C | R | K | F | S | S |
| N | F | F | Y | C | R | K | F | S | I |
| N | F | F | Y | C | R | K | F | G | S |
| N | F | F | Y | C | R | K | F | G | I |
| N | F | F | Y | C | R | N | Y | S | S |
| N | F | F | Y | C | R | N | Y | S | I |
| N | F | F | Y | C | R | N | Y | G | S |
| N | F | F | Y | C | R | N | Y | G | I |
| N | F | F | Y | C | R | N | F | S | S |
| N | F | F | Y | C | R | N | F | S | I |
| N | F | F | Y | C | R | N | F | G | S |
| N | F | F | Y | C | R | N | F | G | I |
| N | F | F | Y | Y | K | K | Y | S | S |
| N | F | F | Y | Y | K | K | Y | S | I |
| N | F | F | Y | Y | K | K | Y | G | S |
| N | F | F | Y | Y | K | K | Y | G | I |
| N | F | F | Y | Y | K | K | F | S | S |
| N | F | F | Y | Y | K | K | F | S | I |
| N | F | F | Y | Y | K | K | F | G | S |
| N | F | F | Y | Y | K | K | F | G | I |
| N | F | F | Y | Y | K | N | Y | S | S |
| N | F | F | Y | Y | K | N | Y | S | I |
| N | F | F | Y | Y | K | N | Y | G | S |
| N | F | F | Y | Y | K | N | Y | G | I |
| N | F | F | Y | Y | K | N | F | S | S |
| N | F | F | Y | Y | K | N | F | S | I |
| N | F | F | Y | Y | K | N | F | G | S |
| N | F | F | Y | Y | K | N | F | G | I |
| N | F | F | Y | Y | R | K | Y | S | S |
| N | F | F | Y | Y | R | K | Y | S | I |
| N | F | F | Y | Y | R | K | Y | G | S |
| N | F | F | Y | Y | R | K | Y | G | I |
| N | F | F | Y | Y | R | K | F | S | S |
| N | F | F | Y | Y | R | K | F | S | I |
| N | F | F | Y | Y | R | K | F | G | S |
| N | F | F | Y | Y | R | K | F | G | I |
| N | F | F | Y | Y | R | N | Y | S | S |
| N | F | F | Y | Y | R | N | Y | S | I |
| N | F | F | Y | Y | R | N | Y | G | S |
| N | F | F | Y | Y | R | N | Y | G | I |
| N | F | F | Y | Y | R | N | F | S | S |
| N | F | F | Y | Y | R | N | F | S | I |
| N | F | F | Y | Y | R | N | F | G | S |
| N | F | F | R | C | K | K | Y | S | S |
| N | F | F | R | C | K | K | Y | S | I |
| N | F | F | R | C | K | K | Y | G | S |
| N | F | F | R | C | K | K | Y | G | I |
| N | F | F | R | C | K | K | F | S | S |
| N | F | F | R | C | K | K | F | S | I |
| N | F | F | R | C | K | K | F | G | S |
| N | F | F | R | C | K | K | F | G | I |
| N | F | F | R | C | K | N | Y | S | S |
| N | F | F | R | C | K | N | Y | S | I |
| N | F | F | R | C | K | N | Y | G | S |
| N | F | F | R | C | K | N | Y | G | I |
| N | F | F | R | C | K | N | F | S | S |
| N | F | F | R | C | K | N | F | S | I |
| N | F | F | R | C | K | N | F | G | S |
| N | F | F | R | C | K | N | F | G | I |
| N | F | F | R | C | R | K | Y | S | S |
| N | F | F | R | C | R | K | Y | S | I |
| N | F | F | R | C | R | K | Y | G | S |
| N | F | F | R | C | R | K | Y | G | I |
| N | F | F | R | C | R | K | F | S | S |
| N | F | F | R | C | R | K | F | S | I |
| N | F | F | R | C | R | K | F | G | S |
| N | F | F | R | C | R | K | F | G | I |
| N | F | F | R | C | R | N | Y | S | S |
| N | F | F | R | C | R | N | Y | G | S |
| N | F | F | R | C | R | N | Y | G | I |
| N | F | F | R | C | R | N | F | S | S |
| N | F | F | R | C | R | N | F | G | S |
| N | F | F | R | C | R | N | F | G | I |
| N | F | F | R | Y | K | K | Y | S | S |
| N | F | F | R | Y | K | K | Y | S | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| N | F | F | R | Y | K | K | Y | G | S |
| N | F | F | R | Y | K | K | Y | G | I |
| N | F | F | R | Y | K | K | F | S | S |
| N | F | F | R | Y | K | K | F | S | I |
| N | F | F | R | Y | K | K | F | G | S |
| N | F | F | R | Y | K | K | F | G | I |
| N | F | F | R | Y | K | N | Y | S | S |
| N | F | F | R | Y | K | N | Y | S | I |
| N | F | F | R | Y | K | N | Y | G | S |
| N | F | F | R | Y | K | N | Y | G | I |
| N | F | F | R | Y | K | N | F | S | S |
| N | F | F | R | Y | K | N | F | S | I |
| N | F | F | R | Y | K | N | F | G | S |
| N | F | F | R | Y | K | N | F | G | I |
| N | F | F | R | Y | R | K | Y | S | S |
| N | F | F | R | Y | R | K | Y | S | I |
| N | F | F | R | Y | R | K | Y | G | S |
| N | F | F | R | Y | R | K | Y | G | I |
| N | F | F | R | Y | R | K | F | S | S |
| N | F | F | R | Y | R | K | F | S | I |
| N | F | F | R | Y | R | K | F | G | S |
| N | F | F | R | Y | R | K | F | G | I |
| N | F | F | R | Y | R | N | Y | S | S |
| N | F | F | R | Y | R | N | Y | S | I |
| N | F | F | R | Y | R | N | Y | G | S |
| N | F | F | R | Y | R | N | Y | G | I |
| N | F | F | R | Y | R | N | F | S | S |
| N | F | F | R | Y | R | N | F | S | I |
| N | F | F | R | Y | R | N | F | G | S |
| N | F | F | R | Y | R | N | F | G | I |
| T | V | L | Y | C | K | K | Y | S | S |
| T | V | L | Y | C | K | K | Y | S | I |
| T | V | L | Y | C | K | K | Y | G | S |
| T | V | L | Y | C | K | K | Y | G | I |
| T | V | L | Y | C | K | K | F | S | S |
| T | V | L | Y | C | K | K | F | S | I |
| T | V | L | Y | C | K | K | F | G | S |
| T | V | L | Y | C | K | K | F | G | I |
| T | V | L | Y | C | K | N | Y | S | S |
| T | V | L | Y | C | K | N | Y | S | I |
| T | V | L | Y | C | K | N | Y | G | S |
| T | V | L | Y | C | K | N | Y | G | I |
| T | V | L | Y | C | K | N | F | S | S |
| T | V | L | Y | C | K | N | F | S | I |
| T | V | L | Y | C | K | N | F | G | S |
| T | V | L | Y | C | K | N | F | G | I |
| T | V | L | Y | C | R | K | Y | S | S |
| T | V | L | Y | C | R | K | Y | S | I |
| T | V | L | Y | C | R | K | Y | G | S |
| T | V | L | Y | C | R | K | Y | G | I |
| T | V | L | Y | C | R | K | F | S | S |
| T | V | L | Y | C | R | K | F | S | I |
| T | V | L | Y | C | R | K | F | G | S |
| T | V | L | Y | C | R | K | F | G | I |
| T | V | L | Y | C | R | N | Y | S | S |
| T | V | L | Y | C | R | N | Y | S | I |
| T | V | L | Y | C | R | N | Y | G | S |
| T | V | L | Y | C | R | N | Y | G | I |
| T | V | L | Y | C | R | N | F | S | S |
| T | V | L | Y | C | R | N | F | S | I |
| T | V | L | Y | C | R | N | F | G | S |
| T | V | L | Y | C | R | N | F | G | I |
| T | V | L | Y | Y | K | K | Y | S | S |
| T | V | L | Y | Y | K | K | Y | S | I |
| T | V | L | Y | Y | K | K | Y | G | S |
| T | V | L | Y | Y | K | K | Y | G | I |
| T | V | L | Y | Y | K | K | F | S | S |
| T | V | L | Y | Y | K | K | F | S | I |
| T | V | L | Y | Y | K | K | F | G | S |
| T | V | L | Y | Y | K | K | F | G | I |
| T | V | L | Y | Y | K | N | Y | S | S |
| T | V | L | Y | Y | K | N | Y | S | I |
| T | V | L | Y | Y | K | N | Y | G | S |
| T | V | L | Y | Y | K | N | Y | G | I |
| T | V | L | Y | Y | K | N | F | S | S |
| T | V | L | Y | Y | K | N | F | G | S |
| T | V | L | Y | Y | K | N | F | G | I |
| T | V | L | Y | Y | R | K | Y | S | S |
| T | V | L | Y | Y | R | K | Y | S | I |
| T | V | L | Y | Y | R | K | Y | G | S |
| T | V | L | Y | Y | R | K | Y | G | I |
| T | V | L | Y | Y | R | K | F | S | S |
| T | V | L | Y | Y | R | K | F | S | I |
| T | V | L | Y | Y | R | K | F | G | S |
| T | V | L | Y | Y | R | K | F | G | I |
| T | V | L | Y | Y | R | N | Y | S | S |
| T | V | L | Y | Y | R | N | Y | S | I |
| T | V | L | Y | Y | R | N | Y | G | S |
| T | V | L | Y | Y | R | N | Y | G | I |
| T | V | L | Y | Y | R | N | F | S | S |
| T | V | L | Y | Y | R | N | F | S | I |
| T | V | L | Y | Y | R | N | F | G | S |
| T | V | L | Y | Y | R | N | F | G | I |
| T | V | L | R | C | K | K | Y | S | S |
| T | V | L | R | C | K | K | Y | S | I |
| T | V | L | R | C | K | K | Y | G | S |
| T | V | L | R | C | K | K | Y | G | I |
| T | V | L | R | C | K | K | F | S | S |
| T | V | L | R | C | K | K | F | S | I |
| T | V | L | R | C | K | K | F | G | S |
| T | V | L | R | C | K | K | F | G | I |
| T | V | L | R | C | K | N | Y | S | S |
| T | V | L | R | C | K | N | Y | S | I |
| T | V | L | R | C | K | N | Y | G | S |
| T | V | L | R | C | K | N | Y | G | I |
| T | V | L | R | C | K | N | F | S | S |
| T | V | L | R | C | K | N | F | S | I |
| T | V | L | R | C | K | N | F | G | S |
| T | V | L | R | C | K | N | F | G | I |
| T | V | L | R | C | R | K | Y | S | S |
| T | V | L | R | C | R | K | Y | S | I |
| T | V | L | R | C | R | K | Y | G | S |
| T | V | L | R | C | R | K | Y | G | I |
| T | V | L | R | C | R | K | F | S | S |
| T | V | L | R | C | R | K | F | S | I |
| T | V | L | R | C | R | K | F | G | S |
| T | V | L | R | C | R | K | F | G | I |
| T | V | L | R | C | R | N | Y | S | S |
| T | V | L | R | C | R | N | Y | S | I |
| T | V | L | R | C | R | N | Y | G | S |
| T | V | L | R | C | R | N | Y | G | I |
| T | V | L | R | C | R | N | F | S | S |
| T | V | L | R | C | R | N | F | S | I |
| T | V | L | R | C | R | N | F | G | S |
| T | V | L | R | C | R | N | F | G | I |
| T | V | L | R | Y | K | K | Y | S | S |
| T | V | L | R | Y | K | K | Y | S | I |
| T | V | L | R | Y | K | K | Y | G | S |
| T | V | L | R | Y | K | K | Y | G | I |
| T | V | L | R | Y | K | K | F | S | S |
| T | V | L | R | Y | K | K | F | S | I |
| T | V | L | R | Y | K | K | F | G | S |
| T | V | L | R | Y | K | K | F | G | I |
| T | V | L | R | Y | K | N | Y | S | S |
| T | V | L | R | Y | K | N | Y | S | I |
| T | V | L | R | Y | K | N | Y | G | S |
| T | V | L | R | Y | K | N | Y | G | I |
| T | V | L | R | Y | K | N | F | S | S |
| T | V | L | R | Y | K | N | F | S | I |
| T | V | L | R | Y | K | N | F | G | S |
| T | V | L | R | Y | K | N | F | G | I |
| T | V | L | R | Y | R | K | Y | S | S |
| T | V | L | R | Y | R | K | Y | S | I |
| T | V | L | R | Y | R | K | Y | G | S |
| T | V | L | R | Y | R | K | Y | G | I |
| T | V | L | R | Y | R | K | F | S | S |
| T | V | L | R | Y | R | K | F | S | I |
| T | V | L | R | Y | R | K | F | G | S |
| T | V | L | R | Y | R | K | F | G | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| T | V | L | R | Y | R | N | Y | S | S |
| T | V | L | R | Y | R | N | Y | S | I |
| T | V | L | R | Y | R | N | Y | G | S |
| T | V | L | R | Y | R | N | Y | G | I |
| T | V | L | R | Y | R | N | F | S | S |
| T | V | L | R | Y | R | N | F | S | I |
| T | V | L | R | Y | R | N | F | G | S |
| T | V | L | R | Y | R | N | F | G | I |
| T | V | F | Y | C | K | K | Y | S | S |
| T | V | F | Y | C | K | K | Y | S | I |
| T | V | F | Y | C | K | K | Y | G | S |
| T | V | F | Y | C | K | K | Y | G | I |
| T | V | F | Y | C | K | K | F | S | S |
| T | V | F | Y | C | K | K | F | S | I |
| T | V | F | Y | C | K | K | F | G | S |
| T | V | F | Y | C | K | K | F | G | I |
| T | V | F | Y | C | K | N | Y | S | S |
| T | V | F | Y | C | K | N | Y | S | I |
| T | V | F | Y | C | K | N | Y | G | S |
| T | V | F | Y | C | K | N | Y | G | I |
| T | V | F | Y | C | K | N | F | S | S |
| T | V | F | Y | C | K | N | F | S | I |
| T | V | F | Y | C | K | N | F | G | S |
| T | V | F | Y | C | K | N | F | G | I |
| T | V | F | Y | C | R | K | Y | S | S |
| T | V | F | Y | C | R | K | Y | S | I |
| T | V | F | Y | C | R | K | Y | G | S |
| T | V | F | Y | C | R | K | Y | G | I |
| T | V | F | Y | C | R | K | F | S | S |
| T | V | F | Y | C | R | K | F | S | I |
| T | V | F | Y | C | R | K | F | G | S |
| T | V | F | Y | C | R | K | F | G | I |
| T | V | F | Y | C | R | N | Y | S | S |
| T | V | F | Y | C | R | N | Y | S | I |
| T | V | F | Y | C | R | N | Y | G | S |
| T | V | F | Y | C | R | N | Y | G | I |
| T | V | F | Y | C | R | N | F | S | S |
| T | V | F | Y | C | R | N | F | S | I |
| T | V | F | Y | C | R | N | F | G | S |
| T | V | F | Y | C | R | N | F | G | I |
| T | V | F | Y | Y | K | K | Y | S | S |
| T | V | F | Y | Y | K | K | Y | S | I |
| T | V | F | Y | Y | K | K | Y | G | S |
| T | V | F | Y | Y | K | K | Y | G | I |
| T | V | F | Y | Y | K | K | F | S | S |
| T | V | F | Y | Y | K | K | F | S | I |
| T | V | F | Y | Y | K | K | F | G | S |
| T | V | F | Y | Y | K | K | F | G | I |
| T | V | F | Y | Y | K | N | Y | S | S |
| T | V | F | Y | Y | K | N | Y | S | I |
| T | V | F | Y | Y | K | N | Y | G | S |
| T | V | F | Y | Y | K | N | Y | G | I |
| T | V | F | Y | Y | K | N | F | S | S |
| T | V | F | Y | Y | K | N | F | S | I |
| T | V | F | Y | Y | K | N | F | G | S |
| T | V | F | Y | Y | K | N | F | G | I |
| T | V | F | Y | Y | R | K | Y | S | S |
| T | V | F | Y | Y | R | K | Y | S | I |
| T | V | F | Y | Y | R | K | Y | G | S |
| T | V | F | Y | Y | R | K | Y | G | I |
| T | V | F | Y | Y | R | K | F | S | S |
| T | V | F | Y | Y | R | K | F | S | I |
| T | V | F | Y | Y | R | K | F | G | S |
| T | V | F | Y | Y | R | K | F | G | I |
| T | V | F | Y | Y | R | N | Y | S | S |
| T | V | F | Y | Y | R | N | Y | S | I |
| T | V | F | Y | Y | R | N | Y | G | S |
| T | V | F | Y | Y | R | N | Y | G | I |
| T | V | F | Y | Y | R | N | F | S | S |
| T | V | F | Y | Y | R | N | F | S | I |
| T | V | F | Y | Y | R | N | F | G | S |
| T | V | F | Y | Y | R | N | F | G | I |
| T | V | F | R | C | K | K | Y | S | S |
| T | V | F | R | C | K | K | Y | S | I |
| T | V | F | R | C | K | K | Y | G | S |
| T | V | F | R | C | K | K | Y | G | I |
| T | V | F | R | C | K | K | F | S | S |
| T | V | F | R | C | K | K | F | S | I |
| T | V | F | R | C | K | K | F | G | S |
| T | V | F | R | C | K | K | F | G | I |
| T | V | F | R | C | K | N | Y | S | S |
| T | V | F | R | C | K | N | Y | S | I |
| T | V | F | R | C | K | N | Y | G | S |
| T | V | F | R | C | K | N | Y | G | I |
| T | V | F | R | C | K | N | F | S | S |
| T | V | F | R | C | K | N | F | S | I |
| T | V | F | R | C | K | N | F | G | S |
| T | V | F | R | C | K | N | F | G | I |
| T | V | F | R | C | R | K | Y | S | S |
| T | V | F | R | C | R | K | Y | S | I |
| T | V | F | R | C | R | K | Y | G | S |
| T | V | F | R | C | R | K | Y | G | I |
| T | V | F | R | C | R | K | F | S | S |
| T | V | F | R | C | R | K | F | S | I |
| T | V | F | R | C | R | K | F | G | S |
| T | V | F | R | C | R | K | F | G | I |
| T | V | F | R | C | R | N | Y | S | S |
| T | V | F | R | C | R | N | Y | S | I |
| T | V | F | R | C | R | N | Y | G | S |
| T | V | F | R | C | R | N | Y | G | I |
| T | V | F | R | C | R | N | F | S | S |
| T | V | F | R | C | R | N | F | S | I |
| T | V | F | R | C | R | N | F | G | S |
| T | V | F | R | C | R | N | F | G | I |
| T | V | F | R | Y | K | K | Y | S | S |
| T | V | F | R | Y | K | K | Y | S | I |
| T | V | F | R | Y | K | K | Y | G | S |
| T | V | F | R | Y | K | K | Y | G | I |
| T | V | F | R | Y | K | K | F | S | S |
| T | V | F | R | Y | K | K | F | S | I |
| T | V | F | R | Y | K | K | F | G | S |
| T | V | F | R | Y | K | K | F | G | I |
| T | V | F | R | Y | K | N | Y | S | S |
| T | V | F | R | Y | K | N | Y | S | I |
| T | V | F | R | Y | K | N | Y | G | S |
| T | V | F | R | Y | K | N | Y | G | I |
| T | V | F | R | Y | K | N | F | S | S |
| T | V | F | R | Y | K | N | F | S | I |
| T | V | F | R | Y | K | N | F | G | S |
| T | V | F | R | Y | K | N | F | G | I |
| T | V | F | R | Y | R | K | Y | S | S |
| T | V | F | R | Y | R | K | Y | S | I |
| T | V | F | R | Y | R | K | Y | G | S |
| T | V | F | R | Y | R | K | Y | G | I |
| T | V | F | R | Y | R | K | F | S | S |
| T | V | F | R | Y | R | K | F | S | I |
| T | V | F | R | Y | R | K | F | G | S |
| T | V | F | R | Y | R | K | F | G | I |
| T | V | F | R | Y | R | N | Y | S | S |
| T | V | F | R | Y | R | N | Y | S | I |
| T | V | F | R | Y | R | N | Y | G | S |
| T | V | F | R | Y | R | N | Y | G | I |
| T | V | F | R | Y | R | N | F | S | S |
| T | V | F | R | Y | R | N | F | S | I |
| T | V | F | R | Y | R | N | F | G | S |
| T | V | F | R | Y | R | N | F | G | I |
| T | F | L | Y | C | K | K | Y | S | S |
| T | F | L | Y | C | K | K | Y | S | I |
| T | F | L | Y | C | K | K | Y | G | S |
| T | F | L | Y | C | K | K | Y | G | I |
| T | F | L | Y | C | K | K | F | S | S |
| T | F | L | Y | C | K | K | F | S | I |
| T | F | L | Y | C | K | K | F | G | S |
| T | F | L | Y | C | K | K | F | G | I |
| T | F | L | Y | C | K | N | Y | S | S |
| T | F | L | Y | C | K | N | Y | S | I |
| T | F | L | Y | C | K | N | Y | G | S |
| T | F | L | Y | C | K | N | Y | G | I |
| T | F | L | Y | C | K | N | F | S | S |
| T | F | L | Y | C | K | N | F | S | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| T | F | L | Y | C | K | N | F | G | S |
| T | F | L | Y | C | K | N | F | G | I |
| T | F | L | Y | C | R | K | Y | S | S |
| T | F | L | Y | C | R | K | Y | S | I |
| T | F | L | Y | C | R | K | Y | G | S |
| T | F | L | Y | C | R | K | Y | G | I |
| T | F | L | Y | C | R | K | F | S | S |
| T | F | L | Y | C | R | K | F | S | I |
| T | F | L | Y | C | R | K | F | G | S |
| T | F | L | Y | C | R | K | F | G | I |
| T | F | L | Y | C | R | N | Y | S | S |
| T | F | L | Y | C | R | N | Y | S | I |
| T | F | L | Y | C | R | N | Y | G | S |
| T | F | L | Y | C | R | N | Y | G | I |
| T | F | L | Y | C | R | N | F | S | S |
| T | F | L | Y | C | R | N | F | S | I |
| T | F | L | Y | C | R | N | F | G | S |
| T | F | L | Y | C | R | N | F | G | I |
| T | F | L | Y | Y | K | K | Y | S | S |
| T | F | L | Y | Y | K | K | Y | S | I |
| T | F | L | Y | Y | K | K | Y | G | S |
| T | F | L | Y | Y | K | K | Y | G | I |
| T | F | L | Y | Y | K | K | F | S | S |
| T | F | L | Y | Y | K | K | F | S | I |
| T | F | L | Y | Y | K | K | F | G | S |
| T | F | L | Y | Y | K | K | F | G | I |
| T | F | L | Y | Y | K | N | Y | S | S |
| T | F | L | Y | Y | K | N | Y | S | I |
| T | F | L | Y | Y | K | N | Y | G | S |
| T | F | L | Y | Y | K | N | Y | G | I |
| T | F | L | Y | Y | K | N | F | S | S |
| T | F | L | Y | Y | K | N | F | S | I |
| T | F | L | Y | Y | K | N | F | G | S |
| T | F | L | Y | Y | K | N | F | G | I |
| T | F | L | Y | Y | R | K | Y | S | S |
| T | F | L | Y | Y | R | K | Y | S | I |
| T | F | L | Y | Y | R | K | Y | G | S |
| T | F | L | Y | Y | R | K | Y | G | I |
| T | F | L | Y | Y | R | K | F | S | S |
| T | F | L | Y | Y | R | K | F | S | I |
| T | F | L | Y | Y | R | K | F | G | S |
| T | F | L | Y | Y | R | K | F | G | I |
| T | F | L | Y | Y | R | N | Y | S | S |
| T | F | L | Y | Y | R | N | Y | S | I |
| T | F | L | Y | Y | R | N | Y | G | S |
| T | F | L | Y | Y | R | N | Y | G | I |
| T | F | L | Y | Y | R | N | F | S | S |
| T | F | L | Y | Y | R | N | F | S | I |
| T | F | L | Y | Y | R | N | F | G | S |
| T | F | L | Y | Y | R | N | F | G | I |
| T | F | L | R | C | K | K | Y | S | S |
| T | F | L | R | C | K | K | Y | S | I |
| T | F | L | R | C | K | K | Y | G | S |
| T | F | L | R | C | K | K | Y | G | I |
| T | F | L | R | C | K | K | F | S | S |
| T | F | L | R | C | K | K | F | S | I |
| T | F | L | R | C | K | K | F | G | S |
| T | F | L | R | C | K | K | F | G | I |
| T | F | L | R | C | K | N | Y | S | S |
| T | F | L | R | C | K | N | Y | S | I |
| T | F | L | R | C | K | N | Y | G | S |
| T | F | L | R | C | K | N | Y | G | I |
| T | F | L | R | C | K | N | F | S | S |
| T | F | L | R | C | K | N | F | S | I |
| T | F | L | R | C | K | N | F | G | S |
| T | F | L | R | C | K | N | F | G | I |
| T | F | L | R | C | R | K | Y | S | S |
| T | F | L | R | C | R | K | Y | S | I |
| T | F | L | R | C | R | K | Y | G | S |
| T | F | L | R | C | R | K | Y | G | I |
| T | F | L | R | C | R | K | F | S | S |
| T | F | L | R | C | R | K | F | S | I |
| T | F | L | R | C | R | K | F | G | S |
| T | F | L | R | C | R | K | F | G | I |
| T | F | L | R | C | R | N | Y | S | S |
| T | F | L | R | C | R | N | Y | S | I |
| T | F | L | R | C | R | N | Y | G | S |
| T | F | L | R | C | R | N | Y | G | I |
| T | F | L | R | C | R | N | F | S | S |
| T | F | L | R | C | R | N | F | S | I |
| T | F | L | R | C | R | N | F | G | S |
| T | F | L | R | C | R | N | F | G | I |
| T | F | L | R | Y | K | K | Y | S | S |
| T | F | L | R | Y | K | K | Y | S | I |
| T | F | L | R | Y | K | K | Y | G | S |
| T | F | L | R | Y | K | K | Y | G | I |
| T | F | L | R | Y | K | K | F | S | S |
| T | F | L | R | Y | K | K | F | S | I |
| T | F | L | R | Y | K | K | F | G | S |
| T | F | L | R | Y | K | K | F | G | I |
| T | F | L | R | Y | K | N | Y | S | S |
| T | F | L | R | Y | K | N | Y | S | I |
| T | F | L | R | Y | K | N | Y | G | S |
| T | F | L | R | Y | K | N | Y | G | I |
| T | F | L | R | Y | K | N | F | S | S |
| T | F | L | R | Y | K | N | F | S | I |
| T | F | L | R | Y | K | N | F | G | S |
| T | F | L | R | Y | K | N | F | G | I |
| T | F | L | R | Y | R | K | Y | S | S |
| T | F | L | R | Y | R | K | Y | S | I |
| T | F | L | R | Y | R | K | Y | G | S |
| T | F | L | R | Y | R | K | Y | G | I |
| T | F | L | R | Y | R | K | F | S | S |
| T | F | L | R | Y | R | K | F | S | I |
| T | F | L | R | Y | R | K | F | G | S |
| T | F | L | R | Y | R | K | F | G | I |
| T | F | L | R | Y | R | N | Y | S | S |
| T | F | F | Y | C | K | K | Y | S | S |
| T | F | F | Y | C | K | K | Y | S | I |
| T | F | F | Y | C | K | K | Y | G | S |
| T | F | F | Y | C | K | K | Y | G | I |
| T | F | F | Y | C | K | K | F | S | S |
| T | F | F | Y | C | K | K | F | S | I |
| T | F | F | Y | C | K | K | F | G | S |
| T | F | F | Y | C | K | K | F | G | I |
| T | F | F | Y | C | K | N | Y | S | S |
| T | F | F | Y | C | K | N | Y | S | I |
| T | F | F | Y | C | K | N | Y | G | S |
| T | F | F | Y | C | K | N | Y | G | I |
| T | F | F | Y | C | K | N | F | S | S |
| T | F | F | Y | C | K | N | F | S | I |
| T | F | F | Y | C | K | N | F | G | S |
| T | F | F | Y | C | K | N | F | G | I |
| T | F | F | Y | C | R | K | Y | S | S |
| T | F | F | Y | C | R | K | Y | S | I |
| T | F | F | Y | C | R | K | Y | G | S |
| T | F | F | Y | C | R | K | Y | G | I |
| T | F | F | Y | C | R | K | F | S | S |
| T | F | F | Y | C | R | K | F | S | I |
| T | F | F | Y | C | R | K | F | G | S |
| T | F | F | Y | C | R | K | F | G | I |
| T | F | F | Y | C | R | N | Y | S | S |
| T | F | F | Y | C | R | N | Y | S | I |
| T | F | F | Y | C | R | N | Y | G | S |
| T | F | F | Y | C | R | N | Y | G | I |
| T | F | F | Y | C | R | N | F | S | S |
| T | F | F | Y | C | R | N | F | S | I |
| T | F | F | Y | C | R | N | F | G | S |
| T | F | F | Y | C | R | N | F | G | I |
| T | F | F | Y | Y | K | K | Y | S | S |
| T | F | F | Y | Y | K | K | Y | S | I |
| T | F | F | Y | Y | K | K | Y | G | S |
| T | F | F | Y | Y | K | K | Y | G | I |

TABLE 6-continued

Exemplary Mutations of 1.140 (SEQ ID NO: 8) Light Chain to Germline at the indicated Residue Number

| 22 | 30 | 31 | 32 | 38 | 45 | 51 | 98 | 99 | 100 |
|---|---|---|---|---|---|---|---|---|---|
| T | F | F | Y | Y | K | K | F | S | S |
| T | F | F | Y | Y | K | K | F | S | I |
| T | F | F | Y | Y | K | K | F | G | S |
| T | F | F | Y | Y | K | K | F | G | I |
| T | F | F | Y | Y | K | N | Y | S | S |
| T | F | F | Y | Y | K | N | Y | S | I |
| T | F | F | Y | Y | K | N | Y | G | S |
| T | F | F | Y | Y | K | N | Y | G | I |
| T | F | F | Y | Y | K | N | F | S | S |
| T | F | F | Y | Y | K | N | F | S | I |
| T | F | F | Y | Y | K | N | F | G | S |
| T | F | F | Y | Y | K | N | F | G | I |
| T | F | F | Y | Y | R | K | Y | S | S |
| T | F | F | Y | Y | R | K | Y | S | I |
| T | F | F | Y | Y | R | K | Y | G | S |
| T | F | F | Y | Y | R | K | Y | G | I |
| T | F | F | Y | Y | R | K | F | S | S |
| T | F | F | Y | Y | R | K | F | S | I |
| T | F | F | Y | Y | R | K | F | G | S |
| T | F | F | Y | Y | R | K | F | G | I |
| T | F | F | Y | Y | R | N | Y | S | S |
| T | F | F | Y | Y | R | N | Y | S | I |
| T | F | F | Y | Y | R | N | Y | G | S |
| T | F | F | Y | Y | R | N | Y | G | I |
| T | F | F | Y | Y | R | N | F | S | S |
| T | F | F | Y | Y | R | N | F | S | I |
| T | F | F | Y | Y | R | N | F | G | S |
| T | F | F | Y | Y | R | N | F | G | I |
| T | F | F | R | C | K | K | Y | S | S |
| T | F | F | R | C | K | K | Y | S | I |
| T | F | F | R | C | K | K | Y | G | S |
| T | F | F | R | C | K | K | Y | G | I |
| T | F | F | R | C | K | K | F | S | S |
| T | F | F | R | C | K | K | F | S | I |
| T | F | F | R | C | K | K | F | G | S |
| T | F | F | R | C | K | K | F | G | I |
| T | F | F | R | C | K | N | Y | S | S |
| T | F | F | R | C | K | N | Y | S | I |
| T | F | F | R | C | K | N | Y | G | S |
| T | F | F | R | C | K | N | Y | G | I |
| T | F | F | R | C | K | N | F | S | S |
| T | F | F | R | C | K | N | F | S | I |
| T | F | F | R | C | K | N | F | G | S |
| T | F | F | R | C | K | N | F | G | I |
| T | F | F | R | C | R | K | Y | S | S |
| T | F | F | R | C | R | K | Y | S | I |
| T | F | F | R | C | R | K | Y | G | S |
| T | F | F | R | C | R | K | Y | G | I |
| T | F | F | R | C | R | K | F | S | S |
| T | F | F | R | C | R | K | F | S | I |
| T | F | F | R | C | R | K | F | G | S |
| T | F | F | R | C | R | K | F | G | I |
| T | F | F | R | C | R | N | Y | S | S |
| T | F | F | R | C | R | N | Y | S | I |
| T | F | F | R | C | R | N | Y | G | S |
| T | F | F | R | C | R | N | Y | G | I |
| T | F | F | R | C | R | N | F | S | S |
| T | F | F | R | C | R | N | F | S | I |
| T | F | F | R | C | R | N | F | G | S |
| T | F | F | R | C | R | N | F | G | I |
| T | F | F | R | Y | K | K | Y | S | S |
| T | F | F | R | Y | K | K | Y | S | I |
| T | F | F | R | Y | K | K | Y | G | S |
| T | F | F | R | Y | K | K | Y | G | I |
| T | F | F | R | Y | K | K | F | S | S |
| T | F | F | R | Y | K | K | F | S | I |
| T | F | F | R | Y | K | K | F | G | S |
| T | F | F | R | Y | K | K | F | G | I |
| T | F | F | R | Y | K | N | Y | S | S |
| T | F | F | R | Y | K | N | Y | S | I |
| T | F | F | R | Y | K | N | Y | G | S |
| T | F | F | R | Y | K | N | Y | G | I |
| T | F | F | R | Y | K | N | F | S | S |
| T | F | F | R | Y | K | N | F | S | I |
| T | F | F | R | Y | K | N | F | G | S |
| T | F | F | R | Y | R | K | Y | S | S |
| T | F | F | R | Y | R | K | Y | S | I |
| T | F | F | R | Y | R | K | Y | G | S |
| T | F | F | R | Y | R | K | Y | G | I |
| T | F | F | R | Y | R | K | F | S | S |
| T | F | F | R | Y | R | K | F | S | I |
| T | F | F | R | Y | R | K | F | G | S |
| T | F | F | R | Y | R | K | F | G | I |
| T | F | F | R | Y | R | N | Y | S | S |
| T | F | F | R | Y | R | N | Y | S | I |
| T | F | F | R | Y | R | N | Y | G | S |
| T | F | F | R | Y | R | N | Y | G | I |
| T | F | F | R | Y | R | N | F | S | S |
| T | F | F | R | Y | R | N | F | S | I |
| T | F | F | R | Y | R | N | F | G | S |
| T | F | F | R | Y | R | N | F | G | I |

Example 9

Inhibition of Heregulin-β Induced ErbB2 Phosphorylation and Cell Proliferation in ErbB2 Low Expressing MCF7 Cells As described in Example 4, the hybridoma supernatants could inhibit Heregulin-induced ErbB2 phosphorylation in MCF7 cells. Using purified monoclonal antibodies, the potency of the ErbB2 antibodies was determined, also compared to two inhibitory antibodies 2C4 and Herceptin®. Briefly, MCF7 cells were seeded at 20,000 cells/well in 96 well plates and cultured in full growth media (10% FCS) overnight. The next day, cell culture plates were washed once with PBS and culture medium was replaced with phenol red-free and serum-free medium. Cells were serum-starved overnight, and then were incubated with mAbs, Herceptin®, or 2C4 titrating 1:5 from 10 μg/ml in serum-free medium for 1 hour before being treated with 10 nM Heregulin-β for 10 minutes. Cell lysates were prepared as described in Example 4 and Phosphor-ErbB2 level was measured using an ELISA kit from RnD systems (human Phospho-ErbB2 DuoSet IC, Cat #DYC1768), according to the protocol provided. Percentage of inhibition was calculated based on the level of pErbB2 in un-stimulated cells and Heregulin-stimulated cells in the absence of antibodies. A dose response curve was plotted for each antibody using the PrismGraphpad software.

Figure 3:
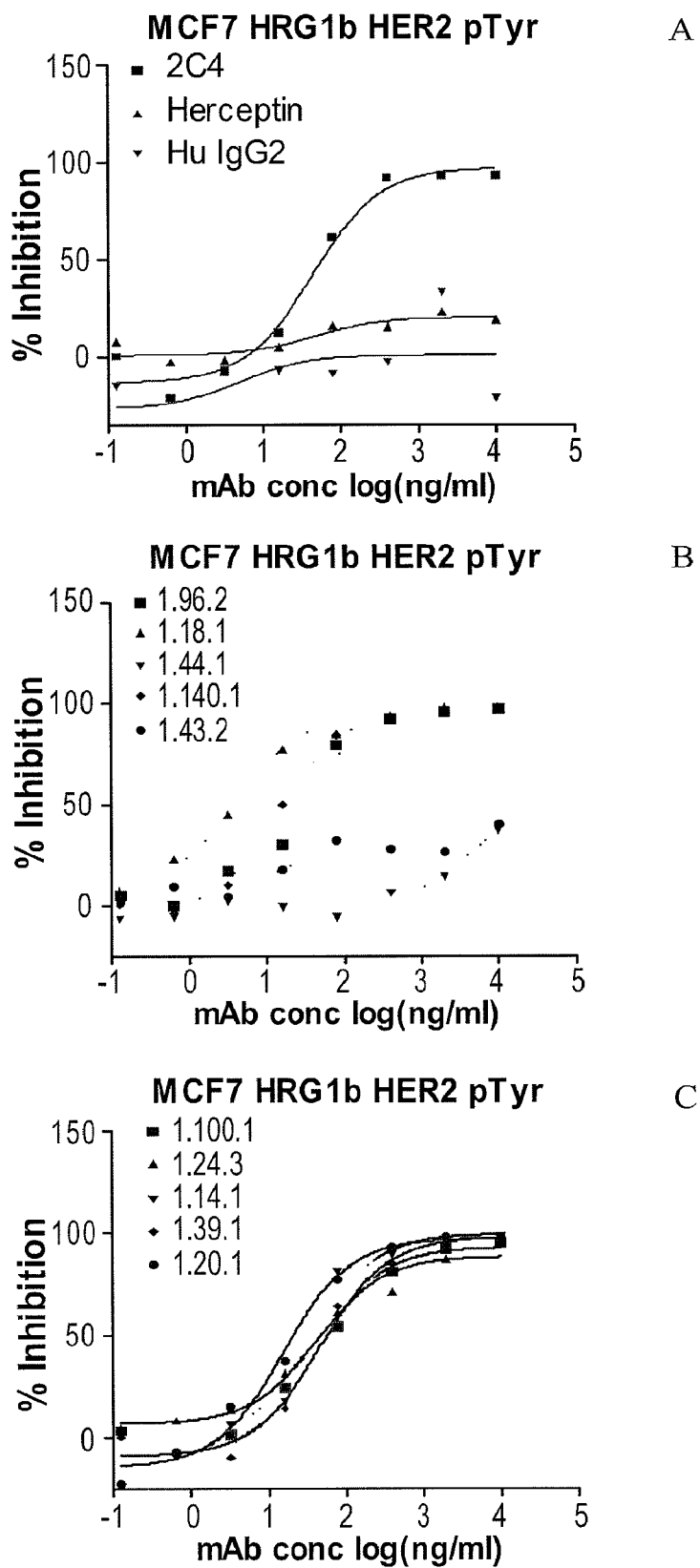
FIGS. 3A-3C show dose response curves for 10 anti-ErbB2 monoclonal antibodies of the invention (B and C) and control antibodies (A) in Heregulin-induced ErbB2 phosphorylation in MCF7 cells.

FIG. 3 illustrates the dose response curves from a representative experiment. EC50 values were derived from non-linear regression analysis, and shown in Table 7. 2C4 inhibited ErbB2 phosphorylation while Herceptin® had little effect. Eight out of 11 monoclonal antibodies of the invention tested showed inhibitory activity on ErbB2 phosphoryaltion in MCF7 cells. 1.18.1 appears to have better potency than 2C4.

TABLE 7

Potency of 10 purified mAbs of the invention at inhibiting Heregulin-induced ErbB2 phophorylation in MCF7 cells.

| mAbs | EC50 (ng/ml) n1 | EC50 (ng/ml) n2 |
|---|---|---|
| 2C4 | 43.6 | 14.6 |
| Herceptin ® | >10,000 | >10,000 |
| 1.18.1 | 4.2 | 10.8 |

TABLE 7-continued

Potency of 10 purified mAbs of the invention at inhibiting Heregulin-induced ErbB2 phophorylation in MCF7 cells.

| mAbs | EC50 (ng/ml) n1 | EC50 (ng/ml) n2 |
|---|---|---|
| 1.20.1 | 15.5 | 17.4 |
| 1.140.1 | 14.65 | 22.9 |
| 1.96.2 | 28.8 | 34 |
| 1.100.1 | 39.9 | 33.7 |
| 1.14.1 | 33.7 | 22.9 |
| 1.39.1 | 46.9 | 26.3 |
| 1.24.3 | 42.9 | 20.4 |
| 1.43.1 | >10,000 | >10,000 |
| 1.44.1 | >10,000 | >10,000 |
| 1.71.3 | >10,000 | nd |

The effect of the monoclonal antibodies on Heregulin-induced cell proliferation was also examined. MCF7 cells were seeded at 6000 cell/well in 96 well plates in Phenol red free DMEM media with 10% FCS, NaPyruvate, L-Glutamine, and allowed to grow overnight at 37° C. The next day, cells were washed once with cold PBS and culture media was replaced with 100 µl of FCS/phenol red free media plus NaPyruvate and incubated for 4 hours at 37° C. Then, FCS-free media was removed and 50 µl of titrated mAbs and 50 µl of 2 nM Heregulin-β were added to cells. After incubating cells with antibodies and Heregulin for three days at 37° C., 25 µl of CellTiter-Glo luminescent reagent (Promega, catalog #07570) was added to each well. Plates were agitated for 5 minutes and then incubated for 10 minutes at room temperature. Luminescence was read out on a microtiterplate luminometer (Tecan GENios Pro). Percentage of inhibition was calculated based on the level of luminescence in unstimulated cells and Heregulin-stimulated cells in the absence of antibodies.

Figure 4:
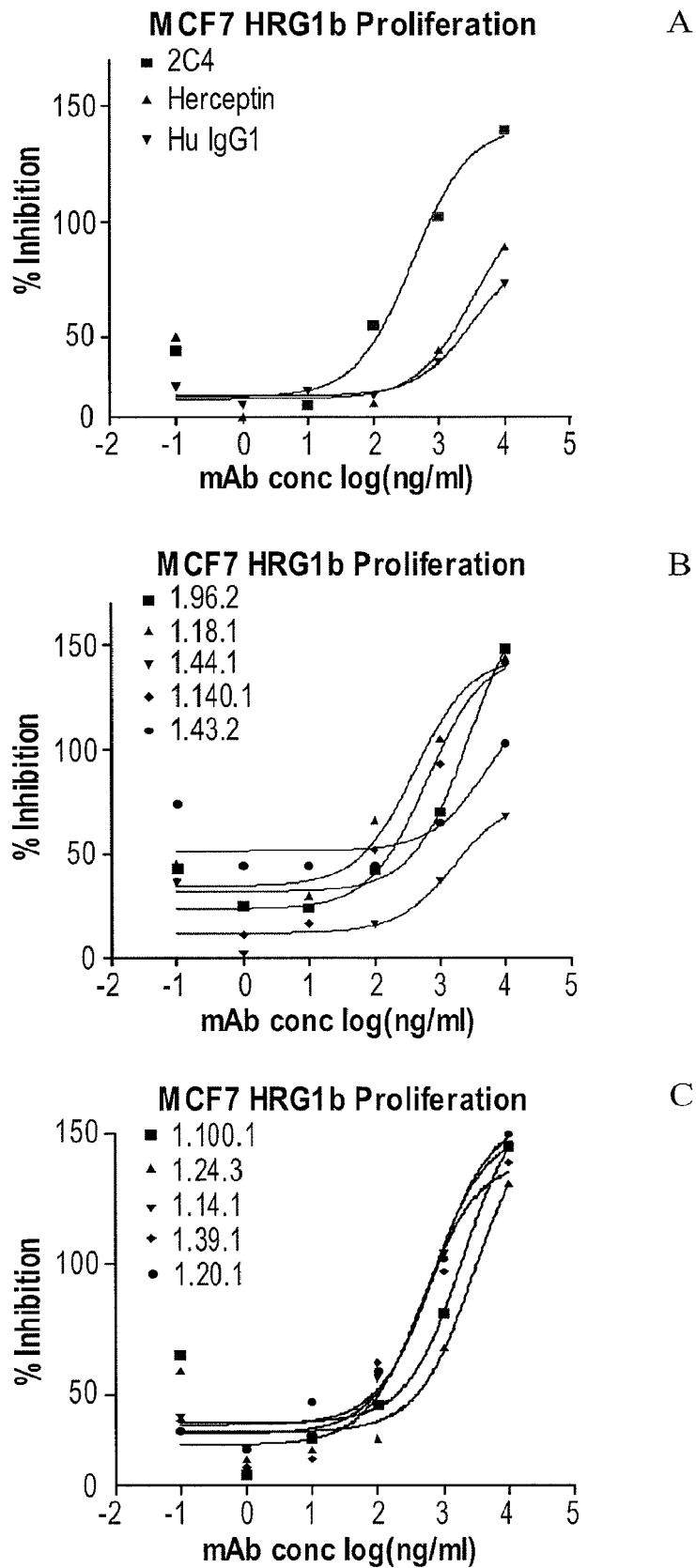
FIGS. 4A-4C show dose response curves for 10 anti-ErbB2 monoclonal antibodies of the invention (B and C) and control antibodies (A) in Heregulin-induced proliferation of MCF7 cells.

As shown in FIG. 4, a dose response curve was plotted for each antibody using the PrismGraphpad software. EC50 values were derived from nonlinear regression analysis, and listed in Table 8. As exhibited in the ErbB2 phosphorylation assay, 2C4 and the same 8 antibodies of the invention that were effective at inhibiting ErbB2 phosphorylation showed dose-dependent inhibition of Heregulin-induced MCF7 cell proliferation while Herceptin® and the 3 antibodies ineffective at blocking ErbB2 phosphorylation did not.

TABLE 8

Potency and efficacy of 10 purified mAbs of the invention at inhibiting Heregulin-induced MCF7 cell proliferation

| mAbs | EC50 (ng/ml) | % Inhibition @10 µg/ml |
|---|---|---|
| 2C4 | 404.5 | 90 |
| Herceptin® | >10,000 | 39 |
| 1.18.1 | 414.8 | 94 |
| 1.20.1 | 770.1 | 100 |
| 1.140.1 | 633.3 | 91 |
| 1.96.2 | 2832 | 98 |
| 1.100.1 | 2043 | 95 |
| 1.14.1 | 640 | 96 |
| 1.39.1 | 479.3 | 89 |
| 1.24.3 | 3017 | 81 |
| 1.43.1 | ~10,000 | 53 |
| 1.44.1 | >10,000 | 18 |
| 1.71.3 | >10,000 | nd |

Example 10

Inhibition of Proliferation of BT474 and SKBR3 Cells

The 8 neutralizing antibodies effective on ErbB2-low expressing cells (MCF7) were also examined for their ability to inhibit ErbB2-high expressing cells in a 4-day cell proliferation assay. Five thousand cells (BT474 or SKBR3) in 50 µl of growth media with 10% FCS were seeded in 96 well plates and incubated at 37° C. for 4 hours in order to attach to plates. Monoclonal antibodies were titrated 1:5 in growth media at 2× final concentrations starting from 40 µg/ml. Fifty (50) of 2C4, Herceptin® and 8 anti-ErbB2 mAbs of the invention were added to the plates and cells were cultured with antibodies for 4 days. Twenty-five (25) µl of CellTiter-glo reagent was added to each well. Plates were agitated for 5 minutes and incubated for 10 minutes at room temperature. Luminescence was read out on a microtiterplate luminometer (Teem GENios Pro). Percentage of inhibition was calculated based on the level of luminescence signal on day 4 and day 0 in the absence of antibodies. A dose response curve was plotted for each antibody using the PrismGraphpad software, and EC50 values were derived from nonlinear regression analysis.

Figure 5:
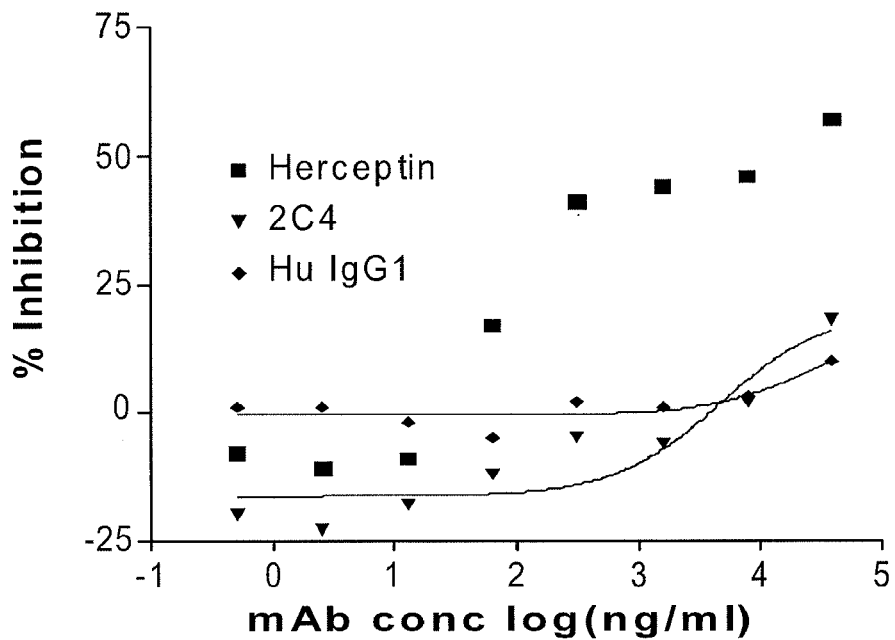
FIGS. 5A and 5B show dose response curves for 8 anti-ErbB2 monoclonal antibodies of the invention (B) and control antibodies (A) in a BT474 cell proliferation assay.
Figure 5:
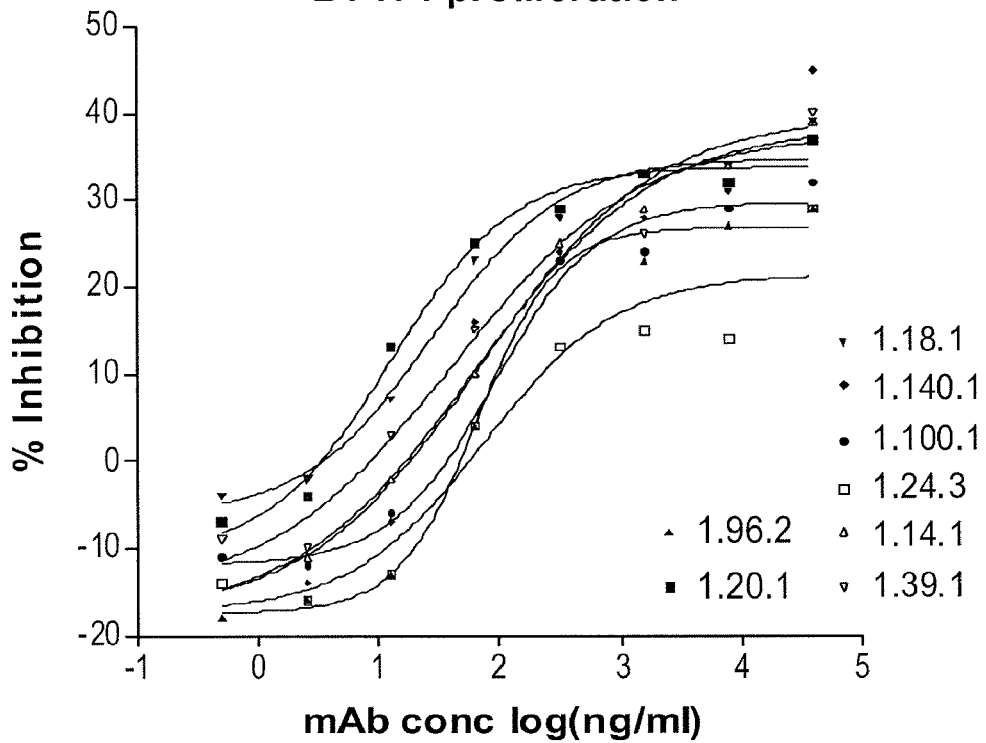
Figure 6:
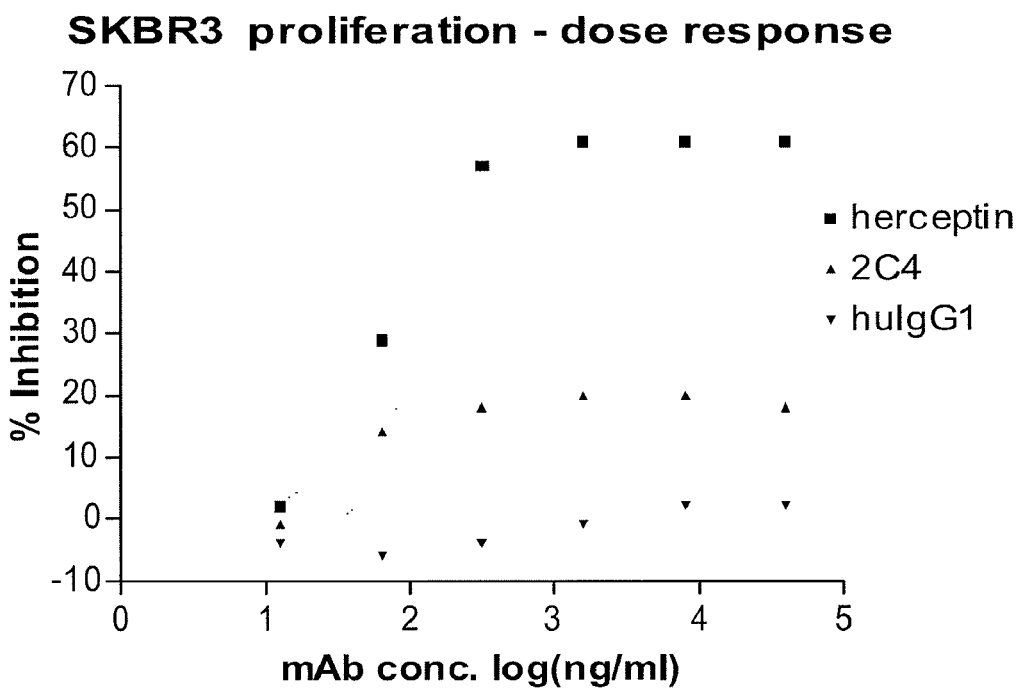
FIGS. 6A and 6B show dose response curves for 8 anti-ErbB2 monoclonal antibodies of the invention (B) and control antibodies (A) in an SKBR3 cell proliferation assay.
Figure 6:
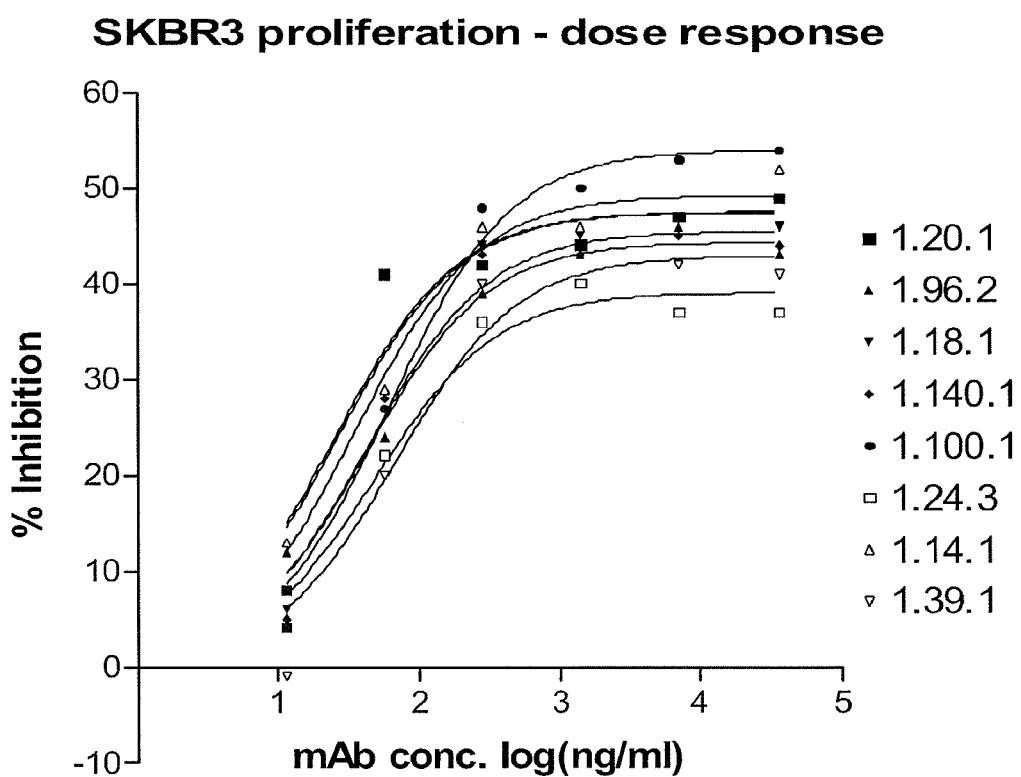

FIGS. 5 and 6 illustrate data from a representative experiment. Both EC50 and maximum percentage of inhibition are listed in Table 9 and 10. As reported, Herceptin® showed dose-dependent inhibition of both BT474 and SKBR3 cell proliferation while 2C4 had little effect. All of the monoclonal antibodies of the invention tested exhibited dose-dependent inhibition of BT474 and SKBR3 cell proliferation with comparable potency to Herceptin®.

TABLE 9

Potency and efficacy of 8 antibodies of the invention at inhibiting BT474 cell proliferation

| Abs | N1 EC50 (ng/ml) | N1% Inhibition @40 µg/ml | N2 EC50 (ng/ml) | N2% Inhibition @40 µg/ml |
|---|---|---|---|---|
| Herceptin® | 144.8 | 61 | 81.8 | 57 |
| 2C4 | >40,000 | −9 | 4750.0 | 18 |
| hIgG1 | >40,000 | −2 | >40,000 | 10 |
| 1.96.2 | 131.3 | 35 | 66.3 | 29 |
| 1.20.1 | 85.3 | 40 | 12.8 | 37 |
| 1.140.1 | 299.8 | 39 | 70.9 | 45 |
| 1.18.1 | 38.1 | 34 | 28.2 | 39 |
| 1.100.1 | 169.4 | 35 | 91.1 | 32 |
| 1.24.3 | 198.3 | 24 | 74.4 | 29 |
| 1.14.1 | 135.7 | 38 | 63.0 | 39 |
| 1.39.1 | 156.4 | 29 | 42.3 | 40 |

TABLE 10

Potency and efficacy of 8 antibodies of the invention at inhibiting SKBR3 cell proliferation

| Abs | EC50 (ng/ml) | % inhibition @36 µg/ml |
|---|---|---|
| Herceptin® | 54.5 | 59 |
| 2C4 | >36,000 | 18 |
| hIgG1 | >36,000 | 2 |
| 1.96.2 | 41.7 | 43 |
| 1.20.1 | 25.2 | 49 |
| 1.140.1 | 42.7 | 44 |
| 1.18.1 | 26.3 | 46 |
| 1.100.1 | 61.3 | 54 |
| 1.24.3 | 48.5 | 37 |
| 1.14.1 | 35.7 | 52 |
| 1.39.1 | 68.9 | 41 |

Example 11

Inhibition of ErbB2 Phosphorylation in BT474 Cells

To identify the mechanism of action of these antibodies in ErbB2-high expressing cell lines, an antibody of the invention 1.18.1, was tested for effect on constitutive ErbB2 phosphorylation in BT474 cells along with Herceptin® and 2C4. BT474 cells were seeded into 96 well culture plates in complete culture media at 5000 cells/well on day 1, 10000 cells/well on day 2 and day 3, or at 20000 cells/well on day 4. Cells were incubated at 37° C. for 3-4 hours and allowed to attach to plates. Monoclonal antibodies were titrated 1:5 in complete media starting from 10 µg/ml for 6 points and then added to cells. Cells were incubated with monoclonal antibodies for 1-4 days. On day 5, cells were lysed in buffer supplemented with protease and phosphatase inhibitors as previously described. Phospho-ErbB2 levels in cell lysates were determined by ELISA. Cell proliferation was measured by CyQuant (Invitrogen). Percentage of inhibition was calculated according to the pErB2 level in the absence of antibodies. Phosphor-ErbB2/cell was also calculated by normalizing phosphor-ErbB2 levels to cell numbers. A dose response curve was plotted for each antibody using the PrismGraphpad software, and EC50 values were derived from nonlinear regression analysis.

Figure 7:
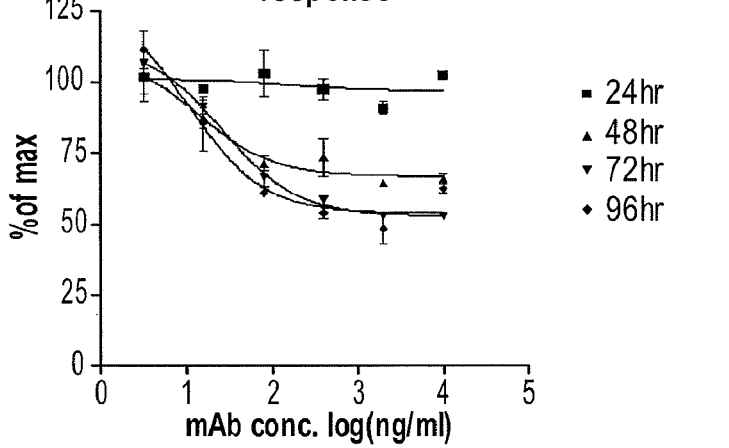
FIGS. 7A-7C show dose-dependent response of total ErbB2 phosphorylation to mAb 1.18.1 (A), Herceptin® (B) and 2C4 (C) after incubating cells with mAbs for 24, 48, 72, or 96 hours.
Figure 7:
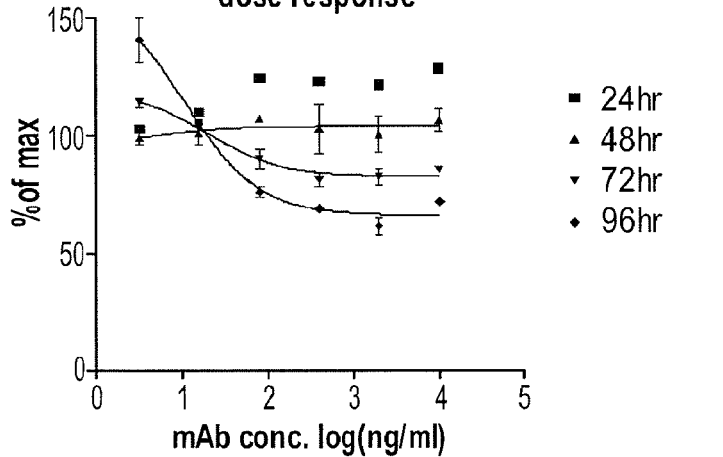
Figure 7:
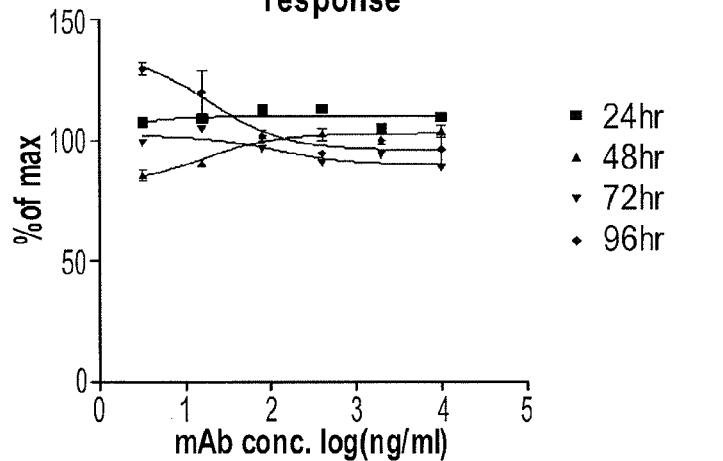
Figure 8:
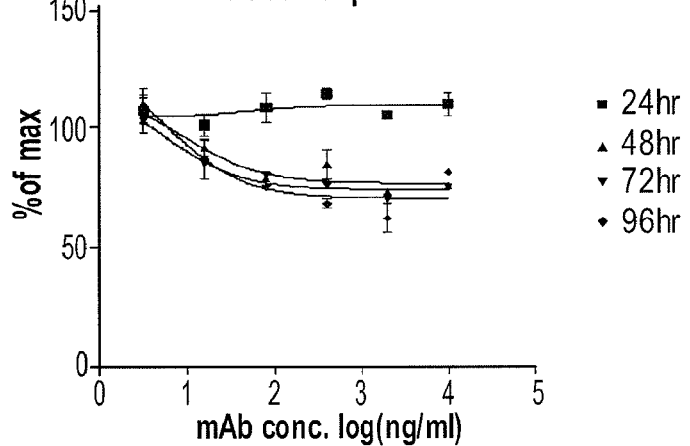
FIGS. 8A-8C show dose-dependent response of normalized ErbB2 phosphorylation to mAb 1.18.1 (A), Herceptin® (B) and 2C4 (C) after incubating cells with mAbs for 24, 48, 72, or 96 hours
Figure 8:
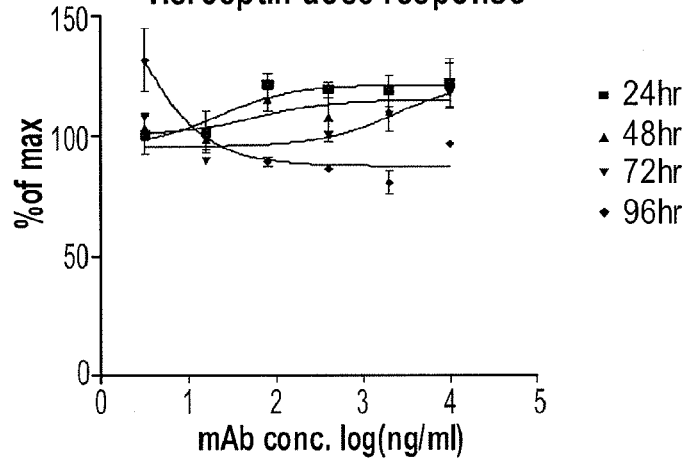
Figure 8:
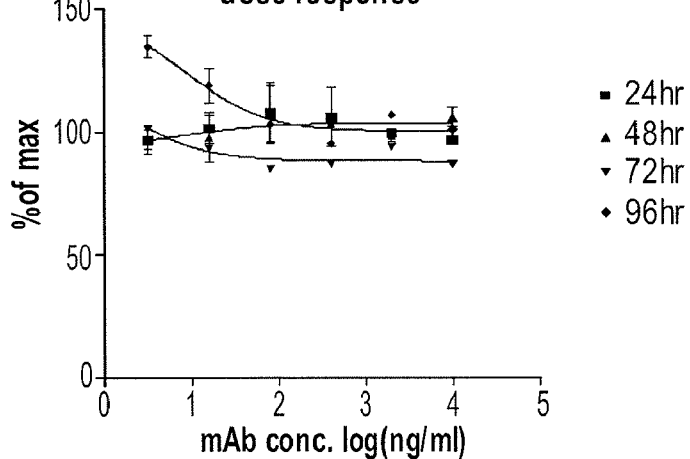

FIGS. 7 and 8 illustrate the dose response at different time points. Both EC50 and maximum percentage of inhibition were listed in Table 11. Monoclonal Ab 1.18.1 started to show inhibition of pErB2 at 48 hrs and reached the maximal inhibition at 72 hours. However, Herceptin® did not show a significant effect until 72 hrs while 2C4 had little effect. Interestingly, when phosphor-ErbB2 levels were normalized by cell number, inhibition of ErbB2 phosphorylation by 1.18.1 reached maximum at 48 hours; while Herceptin® did not appear to inhibit phosphorylation of ErbB2, as previously published.

Next, the effect of 7 of the antibodies on constitutive ErbB2 phosphorylation in BT474 cells after 48 hours was investigated. Briefly, 10,000 BT474 cells in 50 µl of complete culture media was seeded in 96 well plates and cultured for 3-4 hours at 37° C. to attach to the plates. Then 50 µl of 20 ug/ml 2C4, Herceptin® and anti-ErbB2 monoclonal antibodies of the invention, prepared at 2× final concentrations in complete culture media, was added to the plates and incubated with cells for 48 hours. Cell lysates were prepared and phosphor-ErbB2 levels were measured by ELISA as described in Example 4. Percentage of inhibition was calculated according to the pErB2 level in the absence of antibodies. As listed in Table 11, all 7 mAbs of the invention exhibited dose-dependent inhibition of ErbB2 phosphorylation in BT474 cells at 48 hours. In comparison, Herceptin®, and 2C4 had little effect.

TABLE 11

Potency of 7 antibodies of the invention at inhibiting ErbB2 phosphorylation in BT474 cell at 48 hours

| Abs | % Inhibition @10 µg/ml (n1) | % Inhibition @10 µg/ml (n2) |
|---|---|---|
| Herceptin ® | 5 | 10 |
| 2C4 | 10 | 7 |
| 1.96.2 | 37 | 30 |
| 1.20.1 | 21 | 28 |
| 1.140.1 | 31 | 33 |
| 1.18.1 | 24 | 33 |
| 1.100.1 | 37 | 26 |
| 1.14.1 | 37 | 45 |
| 1.39.1 | 37 | 26 |

Example 12

Determination of Anti-ErbB2 Antibody Affinity Using

(A) Medium Resolution Biacore Analysis

The binding affinity of eight of the anti-ErbB2 antibodies was measured by medium resolution Biacore. All experiments were performed using a Biacore 2000 instrument.

First, 12 high-density goat α-human IgG antibody surfaces over three CM5 Biacore chips were prepared using routine amine coupling. Then, mAbs were diluted in HBS-P running buffer containing 100 µg/ml Bovine serum albumin (BSA), specifically mAb 1.18.1 to 11 µg/mL, mAb 1.20.1 to 9.9 µg/mL, mAb 1.100.1 to 11 µg/mL, mAb 1.96.2 to 9.3 µg/mL, mAb 1.140.1 to 9.2 µg/mL, mAb 1.14.1 to 9.3 µg/mL, mAb 1.39.1 to 10 µg/mL, and mAb 1.24.3 to 10 µg/mL. Before each antigen injection cycle, each mAb was captured for six to nine seconds at a 100 µL/min flow rate. A 2-minute wash step followed each capture injection to stabilize each mAb baseline. Purified human ErbB2(ECD)-cMyc/His was injected for 90 seconds at a concentration range of 307-4.80 nM (2× serial dilution) for all mAbs, followed by a 15 minute dissociation except for mAbs 1.39.1 and 1.24.3 where dissociation was followed for 20 mins. All samples were randomly injected with several mAb capture/buffer inject cycles interspersed for double referencing. The high-density goat α-human antibody surfaces were regenerated with one 12-second pulse of 146 mM phosphoric acid (pH 1.5) after each cycle. A flow rate of 100 µL/min. was used for all injection cycles. The data was fit to a 1:1 interaction model using CLAMP. The resulting binding constants are listed in the table below. MAbs are listed in order from highest to lowest affinity.

TABLE 12(a)

Binding affinities of 8 antibodies of the invention against human ErbB2 by Medium resolution Biacore analysis

| mAbs | $R_{max}$ | $k_a$ $(M^{-1}s^{-1})$ | $k_d$ $(s^{-1})$ | $K_D$ (nM) |
|---|---|---|---|---|
| 1.39.1 | 57 | $1.15 \times 10^5$ | $2.36 \times 10^{-4}$ | 2.0 |
| 1.14.1 | 70 | $1.02 \times 10^5$ | $2.56 \times 10^{-4}$ | 2.5 |
| 1.96.2 | 51 | $1.03 \times 10^5$ | $2.73 \times 10^{-4}$ | 2.6 |
| 1.100.1 | 100 | $1.04 \times 10^5$ | $3.01 \times 10^{-4}$ | 2.9 |
| 1.18.1 | 157 | $1.00 \times 10^5$ | $3.02 \times 10^{-4}$ | 3.0 |
| 1.140.1 | 66 | $0.94 \times 10^5$ | $3.33 \times 10^{-4}$ | 3.5 |
| 1.20.1 | 56 | $0.95 \times 10^5$ | $3.44 \times 10^{-4}$ | 3.6 |
| 1.24.3 | 65 | $1.28 \times 10^5$ | $6.55 \times 10^{-4}$ | 5.1 |

(B) High Resolution Biacore Analysis

All experiments were performed using a Biacore T100 instrument. First, a high-density goat α human IgG antibody (Caltag H10500) surface was prepared over two CM5 Biacore chips using routine amine coupling. Each mAb was diluted in HBS-P running buffer containing 100 µg/ml Bovine serum albumin (BSA). MAb 1.140 was diluted to 5 µg/mL, mAb 1.96.2 to 5.9 µg/mL, mAb 1.39.1 to 8.7 µg/mL, mAb 2C4 to 2 µg/mL, and herceptin to 4 µg/mL.

A capture level protocol was developed for all five mAbs. Before each antigen injection cycle, each mAb was captured for 15 to 30 seconds at a 20 µL/min flow rate. A 5-minute wash step followed each capture injection to stabilize each mAb baseline. Antigen hHer-2(ECD)cMyc (Lot #452) was injected for 4 minutes at a concentration range of 369-5.76 nM (2× serial dilution) for mAbs 1.140, 1.96.2, and 1.39.1 followed by a 15 minute dissociation, and a concentration range of 650-10.2 nM (2× serial dilution) for mAb 2C4 and herceptin followed by a 25 minute dissociation. The samples were prepared in the running buffer described above. All samples were randomly injected with several mAb capture/buffer inject cycles interspersed for double referencing. The high-density goat α-human antibody surfaces were regenerated with one 15-second pulse of 146 mM phosphoric acid (pH 1.5) after each cycle. A flow rate of 50 µL/min. was used for all injection cycles.

All sensorgram data were fit to a 1:1 interaction model using CLAMP. The resulting binding constants are listed in the table below. MAbs are listed in order from highest to lowest affinity.

TABLE 12(b)

Binding affinities of 3 antibodies of the invention against human ErbB2 by high resolution Biacore analysis

| Sample | $R_{max}$ | $k_a$ (M$^{-1}$s$^{-1}$) | $k_d$ (s$^{-1}$) | $K_D$ (nM) |
|---|---|---|---|---|
| 2C4 | 105, 88 | $1.21 \times 10^4$ | $3.91 \times 10^{-5}$ | 3.2 |
| herceptin | 60 | $2.34 \times 10^4$ | $9.50 \times 10^{-5}$ | 4.2 |
| 1.140 | 110 | $1.64 \times 10^4$ | $1.73 \times 10^{-4}$ | 10.6 |
| 1.96.2 | 93 | $1.68 \times 10^4$ | $1.94 \times 10^{-4}$ | 11.6 |
| 1.39.1 | 120 | $1.60 \times 10^4$ | $2.14 \times 10^{-4}$ | 13.4 |

Example 13

Competition Binning of Antibodies

2C4 reportedly binds to the dimerization domain on ErbB2 while Herceptin® binds to the C-terminal domain in the extracellular region of ErbB2 (see Franklin et al., Cancer Cell. 2004 April; 5(4):317-28 and Cho et al., Nature. 2003 Feb. 13; 421(6924):756-60, hereby incorporated by reference). To determine if the binding epitopes of 8 of the antibodies overlap with the epitopes for 2C4 or Herceptin®, competitive binning ELISA was performed.

Figure 9:
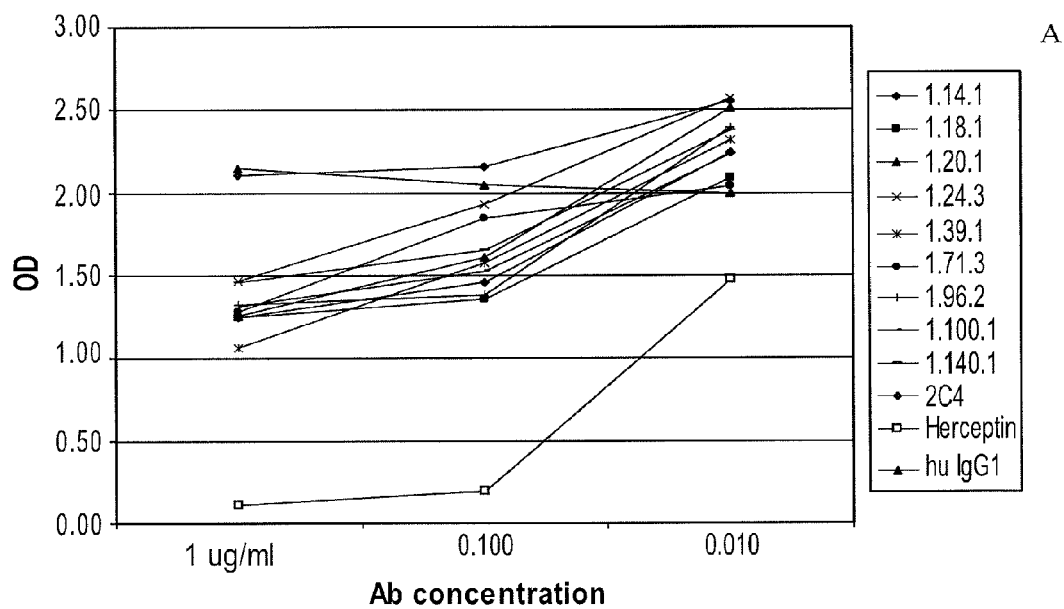
FIGS. 9A and 9B show the results of competition binning indicating that the tested antibodies of the invention do not compete with 2C4 (B) or Herceptin® (A) for ErbB2 binding in an ELISA.
Figure 9:
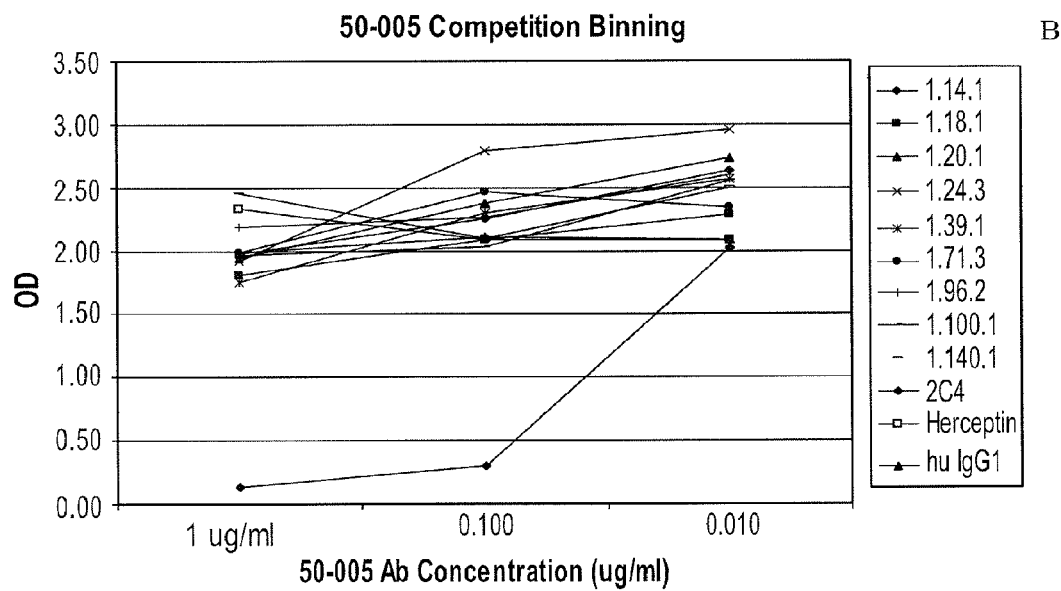

Costar 3695 medium binding 96 well plates were coated with 0.5 µg/ml. Herceptin® or 2 µg/ml 2C4 in PBS overnight at 4° C. Coated plates were washed and then blocked with 1% milk/PBS for 30 minutes at room temperature (RT). Antibodies were titrated to 1000 ng/ml, 100 ng/ml, and 10 ng/ml and pre-incubated with 30 ng/ml hErbB2 (ECD) for 2 hours. The antibody/ErbB2 mixture was transferred to blocked plates and incubated for 1 hour at RT. To detect bound ErbB2, the plates were and washed and incubated with 1 µg/ml goat anti-ErbB2 (R&D systems, catalog #AF1129) for 1 hour at RT. Secondary antibody rabbit anti-goat IgG Fc POD (Pierce catalog #31433, 400 ng/ml) was added to the plates and incubated for 1 hour at RT. After extensive washing, substrate TMB (Neogen) was added and incubated with the plates for 10-18 minutes at RT. The enzyme reaction was stopped by the addition of 1N HCl, and optical density at 450 nm was read on a microplate reader. FIG. 9 illustrates the binding ability of ErbB2 to Herceptin® (A) and 2C4 (B) in the presence of 8 anti-ErbB2 antibodies of the invention, mAb 1.71.3, or an irrelevant isotype control mAb generated in-house. None of the anti-ErbB2 antibodies of the invention block ErbB2 binding to 2C4 or Herceptin®, suggesting that the antibodies belong to a different bin than 2C4 or Herceptin®.

All publications, patents and patent applications herein are incorporated by reference to the same extent as if each individual publication or patent application was specifically and individually indicated to be incorporated by reference. The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art. Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A monoclonal antibody or an antigen-binding fragment thereof that specifically binds ErbB2 wherein the antibody or antigen binding fragment thereof comprises:
   (a) heavy chain CDR1, CDR2 and CDR3 amino acid sequences of SEQ ID NO: 34; and
   (b) light chain CDR1, CDR2 and CDR3 amino acid sequences of SEQ ID NO: 36, wherein there are one to three amino acid substitutions among said CDRs selected from the group consisting of:
      (i) substitution of a cysteine residue with a non-cysteine amino acid residue;
      (ii) substitution of a methionine to eliminate a potential oxidation site; and
      (iii) substitution of a light chain non-germline residue with a corresponding light chain germline residue.

2. The monoclonal antibody or an antigen-binding fragment thereof of claim 1, wherein the heavy chain CDR1 comprises the substitution of a methionine to eliminate a potential oxidation site.

3. The, monoclonal antibody or an antigen-binding fragment thereof of claim 1, wherein the light chain CDR1 comprises the substitution of a cysteine residue with a non-Cysteine amino acid residue.

4. The monoclonal antibody or antigen-binding fragment thereof of claim 1, wherein the antibody or antigen-binding fragment thereof is selected from the group consisting of a chimeric antibody, human antibody and humanized antibody.

5. The monoclonal antibody or antigen-binding fragment thereof of claim 2, wherein the antibody or antigen-binding fragment thereof is selected from the group consisting of a chimeric antibody, human antibody and humanized antibody.

6. The monoclonal antibody or antigen-binding fragment thereof of claim 3, wherein the antibody or antigen-binding fragment thereof is selected from the group consisting of a chimeric antibody, human antibody and humanized antibody.

7. A composition comprising the monoclonal antibody or antigen-binding fragment thereof of claim 1 and a pharmaceutically acceptable carrier.

8. A composition comprising the monoclonal antibody or antigen-binding fragment thereof of claim 2 and a pharmaceutically acceptable carrier.

9. A composition comprising the monoclonal antibody or antigen-binding fragment thereof of claim 3 and a pharmaceutically acceptable carrier.

10. A composition comprising the monoclonal antibody or antigen-binding fragment thereof of claim 4 and a pharmaceutically acceptable carrier.

11. A composition comprising the monoclonal antibody or antigen-binding fragment thereof of claim 5 and a pharmaceutically acceptable carrier.

12. A composition comprising the monoclonal antibody or antigen-binding fragment thereof of claim 6 and a pharmaceutically acceptable carrier.

* * * * *

SEQUENCE LISTING

```
<160> NUMBER OF SEQ ID NOS: 59

<210> SEQ ID NO 1
<211> LENGTH: 387
<212> TYPE: DNA
<213> ORGANISM: Homo sapiens

<400> SEQUENCE: 1
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt ggatacatct attacagtgg gagcacctac     180
tacaacccgt ccctcaagag tcgagttacc atatcagtag acacgtctaa gaaccagttc     240
```

```
tccctgaagc tgagctctgt gactgccgcg gacacggccg tgtattactg tgcgagagag    300
ggcccgatta ctattgttcg gggagtttac tactacttct acggtatgga cgtctggggc    360
caagggacca cggtcaccgt ctcctca                                        387
```

<210> SEQ ID NO 2
<211> LENGTH: 129
<212> TYPE: PRT
<213> ORGANISM: Homo sapiens

<400> SEQUENCE: 2

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Pro Ile Thr Ile Val Arg Gly Val Tyr Tyr Tyr
            100                 105                 110

Phe Tyr Gly Met Asp Val Trp Gly Gln Gly Thr Thr Val Thr Val Ser
        115                 120                 125

Ser
```

<210> SEQ ID NO 3
<211> LENGTH: 336
<212> TYPE: DNA
<213> ORGANISM: Homo sapiens

<400> SEQUENCE: 3

```
gatattgtga tgacccagac tccactctct ctgtccgtca cccctggaca gccggcctcc     60
atctcctgca agtctagtca gagcctcctg catagtgatg gaaagaccta tttgtattgg    120
tacctgcaga agccaggcca gcctccacag cccctgatct atgaagtttc caaccggttc    180
tctggagtgc cagataggtt cagtggcagc gggtcaggga cagatttcac actgaaaatc    240
agccgagtgg aggctgagga tgttggggatt tattactgca tgcaaagtaa acagcttcct    300
cggacgttcg gccaagggac caaggtggaa atcaaa                              336
```

<210> SEQ ID NO 4
<211> LENGTH: 112
<212> TYPE: PRT
<213> ORGANISM: Homo sapiens

<400> SEQUENCE: 4

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Pro Leu Ile Tyr Glu Val Ser Asn Arg Phe Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ser
                 85                  90                  95

Lys Gln Leu Pro Arg Thr Phe Gly Gln Gly Thr Lys Val Glu Ile Lys
            100                 105                 110

<210> SEQ ID NO 5
<211> LENGTH: 363
<212> TYPE: DNA
<213> ORGANISM: Homo sapiens

<400> SEQUENCE: 5
gaggtgcagc tggtggagtc tgggggaggc ctggtcaagc ctgggggtc cctgagactc      60 tcctgtgcag cctctggatt caccttcagt agctatagca tgaactgggt ccgccaggct    120
ccacggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagaggagga    300
gatggctaca attactacta ctttgactac tggggccagg gaaccctggt caccgtctcc    360
tca                                                                  363

<210> SEQ ID NO 6
<211> LENGTH: 121
<212> TYPE: PRT
<213> ORGANISM: Homo sapiens

<400> SEQUENCE: 6

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Arg Lys Gly Leu Glu Trp Val
         35                  40                  45

Ser Ser Ile Ser Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Gly Tyr Asn Tyr Tyr Tyr Phe Asp Tyr Trp Gly
            100                 105                 110

Gln Gly Thr Leu Val Thr Val Ser Ser
            115                 120

<210> SEQ ID NO 7
<211> LENGTH: 339
<212> TYPE: DNA
<213> ORGANISM: Homo sapiens

<400> SEQUENCE: 7
gacatcgtga tgacccagtc tccagactcc ctggctgtgt ctctgggcga gagggccacc      60
atcacctgca gtccagcca gagtgtcttt ttccgctcca acaataagaa ctgcttagct      120
tggtaccagc agagaccagg acagcctcct aatttgctca tttactgggc atctacccgg    180
gaatccgggg tccctgaccg attcagtggc agcgggtctg ggacagattt cactctcacc    240
```

```
atcagcagcc tgcaggctga agatgtggca gtttattact gtcagcaata ttttggttct    300
ccattcactt tcggccctgg gaccaaagtg gatatcaaa                           339
```

<210> SEQ ID NO 8
<211> LENGTH: 113
<212> TYPE: PRT
<213> ORGANISM: Homo sapiens

<400> SEQUENCE: 8

```
Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Val Phe Phe Arg
            20                  25                  30

Ser Asn Asn Lys Asn Cys Leu Ala Trp Tyr Gln Gln Arg Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys
```

<210> SEQ ID NO 9
<211> LENGTH: 351
<212> TYPE: DNA
<213> ORGANISM: Homo sapiens

<400> SEQUENCE: 9

```
gaggtgcagc tggtggagtc tgggggaggc ttggtccagc ctggggggtc cctgagactc    60
tcctgtgcag cctctggatt cacctttagt agctattgga tgcactgggt ccgccagact   120
ccagggaagg ggctggagtg ggtggccaac ataaagcagg atggaagtga aaatactat    180 gtggactctg tgaagggccg attcaccatc tccagagaca acgccaagaa ctcactgcat   240
ctgcaaatga acagcctgag agccgaggac acggctgcgt attactgtgc gagtttccgg   300
gactacggta tggacgtctg gggccaaggg accacggtca ccgtctcctc a            351
```

<210> SEQ ID NO 10
<211> LENGTH: 117
<212> TYPE: PRT
<213> ORGANISM: Homo sapiens

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Thr Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu His
65                  70                  75                  80
```

-continued

```
Leu Gln Met Asn Ser Leu Arg Ala Glu Asp Thr Ala Ala Tyr Tyr Cys
                85                  90                  95
Ala Ser Phe Arg Asp Tyr Gly Met Asp Val Trp Gly Gln Gly Thr Thr
            100                 105                 110
Val Thr Val Ser Ser
        115

<210> SEQ ID NO 11
<211> LENGTH: 321
<212> TYPE: DNA
<213> ORGANISM: Homo sapiens

<400> SEQUENCE: 11
gacatccaga tgacccagtc tccatcctca ctgtctgcat ctgtaggaga cagagtcacc     60
atcacttgtc gggcgagtca gggcattagc aatcatttag cctggtttca gcagaaacca    120
gggaaagccc ctaagtccct gatctatggt gcatccagtt tgcaaaccgg ggtcccatca    180
aagttcagcg gcagtggatc tgggacagat ttcactctca ccatcagcag cctgcagcct    240
gaagattttg caagttattt ctgccaacag tataaaggtt acccgatcac cttcggccaa    300
gggacacgac tggagattaa a                                              321

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn His
            20                  25                  30
Leu Ala Trp Phe Gln Gln Lys Pro Gly Lys Ala Pro Lys Ser Leu Ile
        35                  40                  45
Tyr Gly Ala Ser Ser Leu Gln Thr Gly Val Pro Ser Lys Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Ser Tyr Phe Cys Gln Gln Tyr Lys Gly Tyr Pro Ile
                85                  90                  95
Thr Phe Gly Gln Gly Thr Arg Leu Glu Ile Lys
            100                 105

<210> SEQ ID NO 13
<211> LENGTH: 363
<212> TYPE: DNA
<213> ORGANISM: Homo sapiens

<400> SEQUENCE: 13
gaggtgcagc tggtggagtc tgggggaggc ctggtcaagc ctgggggtc cctgagactc      60 tcctgtgcag cctctggatt caccttcagt agctatagca tgaactgggt ccgccaggct    120
ccagggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagaggagga    300
gatggctaca attactacta ctttgactac tggggccagg gaaccctggt caccgtctcc    360
tca                                                                  363
```

<210> SEQ ID NO 14
<211> LENGTH: 121
<212> TYPE: PRT
<213> ORGANISM: Homo sapiens

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Tyr Tyr Tyr Phe Asp Tyr Trp Gly
            100                 105                 110

Gln Gly Thr Leu Val Thr Val Ser Ser
        115                 120

<210> SEQ ID NO 15
<211> LENGTH: 339
<212> TYPE: DNA
<213> ORGANISM: Homo sapiens

<400> SEQUENCE: 15
gacatcgtga tgacccagtc tccagactcc ctggctgtgt ctctgggcga gagggccacc    60
atcacctgca gtccagccag agtgttttt tccgctccaa acaataagaa ctgcttaact   120
tggtaccagc agagaccggg acagcctcct aacctgctca tttactgggc atctacccgg   180
gaatccgggg tccctgaccg attcagtggc agcgggtctg ggacagattt cactctcacc   240
atcaacaacc tgcaggctga agatgtggca gtttattact gtcagcaata ttttggttct   300
ccattcactt tcggccctgg gaccaaagtg gatatcaaa                           339

<210> SEQ ID NO 16
<211> LENGTH: 113
<212> TYPE: PRT
<213> ORGANISM: Homo sapiens

<400> SEQUENCE: 16

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Val Phe Phe Arg
            20                  25                  30

Ser Asn Asn Lys Asn Cys Leu Thr Trp Tyr Gln Gln Arg Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Val Tyr Tyr Cys Gln Gln
                85                  90                  95

Tyr Phe Gly Ser Pro Phe Thr Phe Gly Pro Gly Thr Lys Val Asp Ile
                100                 105                 110

Lys

<210> SEQ ID NO 17
<211> LENGTH: 363
<212> TYPE: DNA
<213> ORGANISM: Homo sapiens

<400> SEQUENCE: 17
gaggtgcagc tggtggagtc tgggggaggc tggtcaagc ctggggggtc cctgagactc    60
tcctgtgcag cctctggatt caccttcagt agctatagca tgaactgggt ccgccaggct   120
ccagggaagg ggctggagtg ggtctcatcc attagtagta gtagtagtta catatactac   180
gcagactcag tgaagggccg attcaccatc tccagagaca cgccaagaa ctcactgtat    240 ctgcaaatga acagcctgag agccgaggac acggctgtgt attactgtgc gagaggagga   300
gatggctaca attactacta ctttgactac tggggccagg gaaccctggt caccgtctcc   360
tca                                                                363

<210> SEQ ID NO 18
<211> LENGTH: 121
<212> TYPE: PRT
<213> ORGANISM: Homo sapiens

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Tyr Tyr Phe Asp Tyr Trp Gly
                100                 105                 110

Gln Gly Thr Leu Val Thr Val Ser Ser
            115                 120

<210> SEQ ID NO 19
<211> LENGTH: 339
<212> TYPE: DNA
<213> ORGANISM: Homo sapiens

<400> SEQUENCE: 19
gacatcgtga tgacccagtc tccagactcc ctggctgtgt ctctgggcga gagggccacc    60
atcacctgca gtccagcca gagtgttttt ttccgctcca acaataagaa ctgcttagct    120
tggtaccagc agagaccagg acagcctcct aacctgctca tttactgggc atctacccgg   180
gagtccgggg tccctgaccg attcagtggc agcgggtgtg gacagatttt cactctcacc   240
atcagcagcc tgcaggctga agatgtggca gtttattact gtcagcaata ttttggttct   300
ccattcactt tcggccctgg gaccaaagtg gatatcaaa                          339

<210> SEQ ID NO 20
<211> LENGTH: 113
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Val Phe Phe Arg
            20                  25                  30

Ser Asn Asn Lys Asn Cys Leu Ala Trp Tyr Gln Gln Arg Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Cys Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys

<210> SEQ ID NO 21
<211> LENGTH: 363
<212> TYPE: DNA
<213> ORGANISM: Homo sapiens

<400> SEQUENCE: 21
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg gctgagtg gtctcatcc attagtagta gtagtagtta catatactac        180
gcagactcag tgaagggccg attcaccatc tccagagaca acgccaagaa ctcactgtat     240
ctgcaaatga acagcctgag agccgaggac acggctgtgt attactgtgc gagaggagga     300
gatggctaca attactacta ctttgactac tggggccagg gaaccctggt caccgtctcc     360
tca                                                                    363

<210> SEQ ID NO 22
<211> LENGTH: 121
<212> TYPE: PRT
<213> ORGANISM: Homo sapiens

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Tyr Tyr Phe Asp Tyr Trp Gly
                100                 105                 110

Gln Gly Thr Leu Val Thr Val Ser Ser
        115                 120

<210> SEQ ID NO 23
<211> LENGTH: 339
<212> TYPE: DNA
<213> ORGANISM: Homo sapiens

<400> SEQUENCE: 23

```
gacatcgtga tgacccagtc tccagactcc ctggctgtgt ctctgggcga gagggccacc    60
atcacctgca agtccagcca gagtgttttt ttccgctcca acaataagaa ctgcttagct   120
tggtaccagc agagaccagg acagcctcct aacctcctct tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttttggttct   300
ccattcactc tcggccctgg gaccaaagtg gatatcaaa                          339
```

<210> SEQ ID NO 24
<211> LENGTH: 113
<212> TYPE: PRT
<213> ORGANISM: Homo sapiens

<400> SEQUENCE: 24

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Val Phe Phe Arg
            20                  25                  30

Ser Asn Asn Lys Asn Cys Leu Ala Trp Tyr Gln Gln Arg Pro Gly Gln
        35                  40                  45

Pro Pro Asn Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Gly Ser Pro Phe Thr Leu Gly Pro Gly Thr Lys Val Asp Ile
            100                 105                 110

Lys

<210> SEQ ID NO 25
<211> LENGTH: 363
<212> TYPE: DNA
<213> ORGANISM: Homo sapiens

<400> SEQUENCE: 25

```
gaggtgcagc tggtggagtc tgggggaggc ctggtcaagc ctggggggtc cctgagactc    60
tcctgtgcag cctctggatt caccttcagt agctatagca tgaactgggt ccgccaggct   120
ccagggaagg gactggagtg ggtctcatcc attagtagta gtagtagtta catttactac   180
gcagactcag tgaagggccg attcaccatc tccagagaca cgccaagaa ctcactgtat   240
ctgcaaatga acagcctgag cgccgaggac acggctgtgt attcctgtgc gagaggagga   300
gatggctaca attactacta ctttgactac tggggccagg gaaccctggt caccgtctcc   360
tca                                                                363
```

<210> SEQ ID NO 26
<211> LENGTH: 121
<212> TYPE: PRT
<213> ORGANISM: Homo sapiens

<400> SEQUENCE: 26

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Ser Ala Glu Asp Thr Ala Val Tyr Ser Cys
                85                  90                  95

Ala Arg Gly Gly Asp Gly Tyr Asn Tyr Tyr Tyr Phe Asp Tyr Trp Gly
            100                 105                 110

Gln Gly Thr Leu Val Thr Val Ser Ser
        115                 120
```

<210> SEQ ID NO 27
<211> LENGTH: 339
<212> TYPE: DNA
<213> ORGANISM: Homo sapiens

<400> SEQUENCE: 27

```
gacatcgtga tgacccagtc tccaggctcc ctggttgtgt ctctgggcga gagggccacc    60
atcacctgca gtccagcca gagtgttttt ttccgctcca acaataagaa ctgcttagct   120
tggtaccagc agagaccagg acagtctcct aacctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttttggttct   300
ccattcactt tcggccctgg gaccaaagtg gatatcaaa                         339
```

<210> SEQ ID NO 28
<211> LENGTH: 113
<212> TYPE: PRT
<213> ORGANISM: Homo sapiens

<400> SEQUENCE: 28

```
Asp Ile Val Met Thr Gln Ser Pro Gly Ser Leu Val Val Ser Leu Gly
 1               5                  10                  15

Glu Arg Ala Thr Ile Thr Cys Lys Ser Ser Gln Ser Val Phe Phe Arg
            20                  25                  30

Ser Asn Asn Lys Asn Cys Leu Ala Trp Tyr Gln Arg Pro Gly Gln
        35                  40                  45

Ser Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Gly Ser Pro Phe Thr Phe Gly Pro Gly Thr Lys Val Asp Ile
```

Lys

<210> SEQ ID NO 29
<211> LENGTH: 363
<212> TYPE: DNA
<213> ORGANISM: Homo sapiens

<400> SEQUENCE: 29

```
gaggtgcagc tggtggagtc tgggggaggc ctggtcaagc ctggggggtc cctgagactc      60
tcctgtgcag cctctggatt caccttcagt agctataccca tgaactgggt ccgccaggct    120
ccagggaagg ggctggagtg ggtctcatcc attagtagta gtagtagtta catttactac    180
gcagactcag tgaagggccg attcaccatc tccagagaca acgccaagaa ctcactgtat    240
ctgcaaatga acagcctgag cgccgaggac acggctgtgt attcctgtgc gagaggagga    300
gatggctaca attactacta ctttgactac tggggccagg gaaccctggt caccgtctcc    360
tca                                                                   363
```

<210> SEQ ID NO 30
<211> LENGTH: 121
<212> TYPE: PRT
<213> ORGANISM: Homo sapiens

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Ser Ala Glu Asp Thr Ala Val Tyr Ser Cys
                85                  90                  95

Ala Arg Gly Gly Asp Gly Tyr Asn Tyr Tyr Tyr Phe Asp Tyr Trp Gly
            100                 105                 110

Gln Gly Thr Leu Val Thr Val Ser Ser
        115                 120

<210> SEQ ID NO 31
<211> LENGTH: 339
<212> TYPE: DNA
<213> ORGANISM: Homo sapiens

<400> SEQUENCE: 31

```
gacatcgtga tgacccagtc tccaggctcc ctggttgtgt ctctgggcga gagggccacc     60
atcacctgca gtccagcca gagtgttttt ttccgctcca acaataagaa ctgcttagct    120
tggtaccagc agagaccagg acagtctcct aacctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttttggttct    300
ccattcactt tcggccctgg gaccaaagtg gatatcaaa                           339
```

<210> SEQ ID NO 32
<211> LENGTH: 113
<212> TYPE: PRT
<213> ORGANISM: Homo sapiens

<400> SEQUENCE: 32

Asp Ile Val Met Thr Gln Ser Pro Gly Ser Leu Val Val Ser Leu Gly
1               5                   10                  15

Glu Arg Ala Thr Ile Thr Cys Lys Ser Ser Gln Ser Val Phe Phe Arg
            20                  25                  30

Ser Asn Asn Lys Asn Cys Leu Ala Trp Tyr Gln Gln Arg Pro Gly Gln
        35                  40                  45

Ser Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys

<210> SEQ ID NO 33
<211> LENGTH: 363
<212> TYPE: DNA
<213> ORGANISM: Homo sapiens

<400> SEQUENCE: 33
gaggtgcagc tggtggagtc tgggggaggc ctggtcaagc ctgggggggtc cctgagactc     60 tcctgtgcag cctctggatt caccttcagt agctatagca tgaactgggt ccgccaggct    120
ccagggaagg ggctggagtg ggtctcatcc attagtagta gtagtagtta catatactac    180
gcagactcag tgaagggccg attcaccatc tccagagaca cgccaagaa ctcactgtat     240 ctgcaaatga acagcctgag agccgaggac acggctgtgt attactgtgc gagaggagga    300
gatggctaca attactacta ctttgactac tggggccagg gaaccctggt caccgtctcc    360
tca                                                                  363

<210> SEQ ID NO 34
<211> LENGTH: 121
<212> TYPE: PRT
<213> ORGANISM: Homo sapiens

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Tyr Tyr Tyr Phe Asp Tyr Trp Gly

```
              100                 105                 110
Gln Gly Thr Leu Val Thr Val Ser Ser
            115                 120
```

<210> SEQ ID NO 35
<211> LENGTH: 339
<212> TYPE: DNA
<213> ORGANISM: Homo sapiens

<400> SEQUENCE: 35

```
gacatcgtga tgacccagtc tccagactcc ctggctgtgt ctctgggcga gagggccacc      60
atcacctgca gtccagcca gagtgttttt ttccgctcca acaataagaa ctgcttagct     120
tggtaccagc agagaccagg acagcctcct aacctactca tttactgggc atcttcccgg    180
gaatccgggg tccctgaccg gttcagtggc agcgggtctg ggacagattt cgctctcacc    240
atcagcagcc tgcagactga ggatgtggca gtttattact gtcagcaata ttttggttct    300
ccattcactt tcggccctgg gaccaaagtg gatatcaaa                           339
```

<210> SEQ ID NO 36
<211> LENGTH: 113
<212> TYPE: PRT
<213> ORGANISM: Homo sapiens

<400> SEQUENCE: 36

```
Asp Ile Val Met Thr Gln Ser Pro Asp Ser Leu Ala Val Ser Leu Gly
1               5                   10                  15
Glu Arg Ala Thr Ile Thr Cys Lys Ser Ser Gln Ser Val Phe Phe Arg
            20                  25                  30
Ser Asn Asn Lys Asn Cys Leu Ala Trp Tyr Gln Gln Arg Pro Gly Gln
        35                  40                  45
Pro Pro Asn Leu Leu Ile Tyr Trp Ala Ser Ser Arg Glu Ser Gly Val
    50                  55                  60
Pro Asp Arg Phe Ser Gly Ser Gly Ser Gly Thr Asp Phe Ala Leu Thr
65                  70                  75                  80
Ile Ser Ser Leu Gln Thr Glu Asp Val Ala Val Tyr Tyr Cys Gln Gln
                85                  90                  95
Tyr Phe Gly Ser Pro Phe Thr Phe Gly Pro Gly Thr Lys Val Asp Ile
            100                 105                 110
Lys
```

<210> SEQ ID NO 37
<211> LENGTH: 363
<212> TYPE: DNA
<213> ORGANISM: Homo sapiens

<400> SEQUENCE: 37

```
gaggtgcagc tggtggagtc tgggggaggc ctggtcaagc ctggggggtc cctgagactc      60
tcctgtgcag cctctggatt caccttcagt agctatagca tgaactgggt ccgccaggct    120
ccagggaagg gctggagtg gtctcatcc attagtagta gtagtagtta catatactac      180
gcagactcag tgaagggccg attcaccatc tccagagaca cgccaagaa ctcactgtat     240
ctgcaaatga acagcctgag agccgaggac acggctgtgt attactgtgc gagaggagga    300
gatggctaca attactacta ctttgactac tggggccagg gaaccctggt caccgtctcc    360
tca                                                                  363
```

```
<210> SEQ ID NO 38
<211> LENGTH: 121
<212> TYPE: PRT
<213> ORGANISM: Homo sapiens

<400> SEQUENCE: 38

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Tyr Tyr Phe Asp Tyr Trp Gly
            100                 105                 110

Gln Gly Thr Leu Val Thr Val Ser Ser
        115                 120

<210> SEQ ID NO 39
<211> LENGTH: 339
<212> TYPE: DNA
<213> ORGANISM: Homo sapiens

<400> SEQUENCE: 39
gacatcgtga tgacccagtt tccagactcc ctggctgtgt ctctggacga aagggccacc      60
atcaactgca agtccagtca gagtgttttt ttccgctcca acaataagaa ctgcttagct     120
tggtaccagc agaaaccagg acagcctcct aatctgctca tttactgggc atctacccgg     180
gaatccgggg tccctgaccg attcagtggc agcgggtctg ggacagattt cactctcacc     240
atcagcagcc tgcaggctga agatgtggct ttttattact gtcagcaata ttatagttct     300
ccattcactt tcggccctgg gaccaaagtg gatatcaaa                            339

<210> SEQ ID NO 40
<211> LENGTH: 113
<212> TYPE: PRT
<213> ORGANISM: Homo sapiens

<400> SEQUENCE: 40

Asp Ile Val Met Thr Gln Phe Pro Asp Ser Leu Ala Val Ser Leu Asp
1               5                   10                  15

Glu Arg Ala Thr Ile Asn Cys Lys Ser Ser Gln Ser Val Phe Phe Arg
            20                  25                  30

Ser Asn Asn Lys Asn Cys Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Phe Tyr Tyr Cys Gln Gln
                85                  90                  95

Tyr Tyr Ser Ser Pro Phe Thr Phe Gly Pro Gly Thr Lys Val Asp Ile
            100                 105                 110
```

Lys

<210> SEQ ID NO 41
<211> LENGTH: 369
<212> TYPE: DNA
<213> ORGANISM: Homo sapiens

<400> SEQUENCE: 41

```
gaggtgcagc tggtggagtc tgggggaggc ttggttcagc ctgggggtc  cctgagactc    60
tcctgtacag cctctggatt ccccttcagt agctacgaca tgcactgggt ccgccaagct   120
acaggaaaag gtctggagtg gtctcagct attggtactg ctggtgacac attctatcca    180
ggctccgtga agggccgatt caccatctcc agagaaaatg ccaagaactc cttgtatctt   240
caaatgaaca gcctgagagc cggggacacg gctgtgtatt actgtgcaag agaggggtat   300
agcagtgggc gctacttcta ctacggtatg gacgtctggg gccaagggac cacggtcacc   360
gtctcctca                                                           369
```

<210> SEQ ID NO 42
<211> LENGTH: 123
<212> TYPE: PRT
<213> ORGANISM: Homo sapiens

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Pro Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Phe Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Tyr Ser Ser Gly Arg Tyr Phe Tyr Tyr Gly Met Asp Val
            100                 105                 110

Trp Gly Gln Gly Thr Thr Val Thr Val Ser Ser
        115                 120
```

<210> SEQ ID NO 43
<211> LENGTH: 336
<212> TYPE: DNA
<213> ORGANISM: Homo sapiens

<400> SEQUENCE: 43

```
gatgttgtga tgactcagtc tccactctcc ctgcccgtca cccttggaca gccggcctcc    60
atatcctgca ggtctagtca aagcctcgta tacagtgatg gaaacaccta cttgaattgg   120
tttcagcaga ggccaggcca atctccaagg cgcctaattt ataaggtttc taactgggac   180
tctggggtcc cagacagatt cagcggcagt gggtcaggca ctgatttcac actgaaaatc   240
agcagggtgg aggctgagga tgttggggtt tattactgca tgcaaggtac acactggccg   300
ctcactttcg gcggagggac caaggtggag atcaaa                            336
```

<210> SEQ ID NO 44

```
<211> LENGTH: 112
<212> TYPE: PRT
<213> ORGANISM: Homo sapiens

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110

<210> SEQ ID NO 45
<211> LENGTH: 1255
<212> TYPE: PRT
<213> ORGANISM: Homo sapiens

<400> SEQUENCE: 45

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240
```

-continued

```
Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655
```

-continued

```
Ala Val Val Gly Ile Leu Leu Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
        690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
        770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
        835                 840                 845
Arg Asn Val Leu Val Lys Ser Pro Asn His Val Lys Ile Thr Asp Phe
        850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Glu Arg Leu Pro Gln Pro
        930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
        995                 1000                1005
Leu Glu Asp Asp Asp Met Gly Asp Leu Val Asp Ala Glu Glu Tyr
        1010                1015                1020
Leu Val Pro Gln Gln Gly Phe Phe Cys Pro Asp Pro Ala Pro Gly
        1025                1030                1035
Ala Gly Gly Met Val His His Arg His Arg Ser Ser Ser Thr Arg
        1040                1045                1050
Ser Gly Gly Gly Asp Leu Thr Leu Gly Leu Glu Pro Ser Glu Glu
        1055                1060                1065
Glu Ala Pro Arg Ser Pro Leu Ala Pro Ser Glu Gly Ala Gly Ser
```

|   |   |   |   |   |   |   |   |   |   |
|---|---|---|---|---|---|---|---|---|---|
| | | | 1070 | | | 1075 | | | 1080 |
| Asp | Val | Phe | Asp | Gly | Asp | Leu | Gly | Met | Gly | Ala | Ala | Lys | Gly | Leu |
| | | | 1085 | | | 1090 | | | 1095 |

Asp Val Phe Asp Gly Asp Leu Gly Met Gly Ala Ala Lys Gly Leu
        1085            1090            1095

Gln Ser Leu Pro Thr His Asp Pro Ser Pro Leu Gln Arg Tyr Ser
        1100            1105            1110

Glu Asp Pro Thr Val Pro Leu Pro Ser Glu Thr Asp Gly Tyr Val
        1115            1120            1125

Ala Pro Leu Thr Cys Ser Pro Gln Pro Glu Tyr Val Asn Gln Pro
        1130            1135            1140

Asp Val Arg Pro Gln Pro Pro Ser Pro Arg Glu Gly Pro Leu Pro
        1145            1150            1155

Ala Ala Arg Pro Ala Gly Ala Thr Leu Glu Arg Pro Lys Thr Leu
        1160            1165            1170

Ser Pro Gly Lys Asn Gly Val Val Lys Asp Val Phe Ala Phe Gly
        1175            1180            1185

Gly Ala Val Glu Asn Pro Glu Tyr Leu Thr Pro Gln Gly Gly Ala
        1190            1195            1200

Ala Pro Gln Pro His Pro Pro Ala Phe Ser Pro Ala Phe Asp
        1205            1210            1215

Asn Leu Tyr Tyr Trp Asp Gln Asp Pro Pro Glu Arg Gly Ala Pro
        1220            1225            1230

Pro Ser Thr Phe Lys Gly Thr Pro Thr Ala Glu Asn Pro Glu Tyr
        1235            1240            1245

Leu Gly Leu Asp Val Pro Val
        1250            1255

<210> SEQ ID NO 46
<211> LENGTH: 1624
<212> TYPE: DNA
<213> ORGANISM: Homo sapiens

<400> SEQUENCE: 46

```
gcgtgctgat caggactgca cacagagaac tcaccatgga atttgggctg cgctgggttt      60
tccttgttgc tattttaaaa gatgtccagt gtgacgtgca actggtggag tccggggag     120
gcttagttca gcctgggggg tccctgagac tctcctgcgc agcctctgga ttcgcctaca    180
gtagttttg gatgcactgg gtccgccaag ctccagggag gggtctggtg tgggtctcac    240
gtattaatcc tgatgggaga atcacagtct acgcggacgc cgtaaagggc cgattcacca    300
tctccagaga caacgccaag aacacgctct atctccaaat gaacaacctg agagccgagg    360
acacggctgt ttattactgt gcaagaggga cacgatttct ggagttgact tctaggggac    420
aaatggacca gtggggccag ggaaccctgg tcactgtctc ctcagcctcc accaagggcc    480
catcggtctt ccccctggca ccctcctcca agagcacctc tgggggcaca gcggccctgg    540
gctgcctggt caaggactac ttccccgaac cggtgacggt gtcgtggaac tcaggcgccc    600
tgaccagcgg cgtgcacacc ttcccggctg tcctacagtc ctcaggactc tactccctca    660
gcagcgtggt gaccgtgccc tccagcagct gggcaccca gacctacatc tgcaacgtga    720
atcacaagcc cagcaacacc aaggtggaca agaaagttga gcccaaatct tgtgacaaaa    780
ctcacacatg cccaccgtgc ccagcacctg aactcctggg gggaccgtca gtcttcctct    840
tccccccaaa acccaaggac accctcatga tctcccggac ccctgaggtc acatgcgtgg    900
tggtggacgt gagccacgaa gaccctgagg tcaagttcaa ctggtacgtg gacggcgtgg    960
aggtgcataa tgccaagaca aagccgcggg aggagcagta caacagcacg taccgtgtgg   1020
```

```
tcagcgtcct caccgtcctg caccaggact ggctgaatgg caaggagtac aagtgcaagg    1080
tctccaacaa agcccctcca gcccccatcg agaaaaccat ctccaaagcc aaagggcagc    1140
cccgagaacc acaggtgtac accctgcccc catcccggga tgagctgacc aagaaccagg    1200
tcagcctgac ctgcctggtc aaaggcttct atcccagcga catcgccgtg gagtgggaga    1260
gcaatgggca gccggagaac aactacaaga ccacgcctcc cgtgctggac tccgacggct    1320
ccttcttcct ctacagcaag ctcaccgtgg acaagagcag gtggcagcag gggaacgtct    1380
tctcatgctc cgtgatgcat gaggctctgc acaaccacta cacgcagaag agcctctccc    1440
tgtctccggg taaatgagtg cgacggccgg caagcccccg ctccccgggc tctcgcggtc    1500
gcacgaggat gcttggcacg taccccgtgt acatacttcc cgggcgccca gcatggaaat    1560
aaagcaccca gcgctgccct ggaaaaaaaa aaaaaaaaa aaaaaaaaa aaaaaaaaa    1620 aaaa                                                                 1624

<210> SEQ ID NO 47
<211> LENGTH: 938
<212> TYPE: DNA
<213> ORGANISM: Homo sapiens

<400> SEQUENCE: 47
ggtcaggaca cagcatggac atgagggtcc ccgctcagct cctggggctc ctgctactct      60
ggctccgagg tgccagatgt gacatccagt tgacccagtc tccatcctcc ctgtctgcag     120
ctgtaggaga cagagtcacc atcgcttgcc gggcaagtca gagcattgcc gactatttaa     180
attggtatca gcagaaacca gggaaagccc ctaaactcct gatctatggt tcatccagtt     240
tgcaaagcgg ggtcccatca aggttcagtg gcagtggatc tgggacagat ttcactctct     300
ccatcagcag tctacaacct ggagattttg caacttacta ctgtcaacag agtcacactt     360 ccccttttcac ttttggcgga gggaccaagg tgcagatgaa agcgaactgt gctgcaccat     420
ctgtcttcat cttcccgcca tctgatgagc agttgaaatc tggaactgcc tctgttgtgt     480
gcctgctgaa taacttctat cccagagagg ccaaagtaca gtggaaggtg gataacgccc     540
tccaatcggg taactcccag gagagtgtca cagagcagga cagcaaggac agcacctaca     600
gcctcagcag caccctgacg ctgagcaaag cagactacga gaaacacaaa gtctacgcct     660
gcgaagtcac ccatcagggc ctgagctcgc ccgtcacaaa gagcttcaac aggggagagt     720
gttagaggga gaagtgcccc cacctgctcc tcagttccag cctgaccccc tcccatcctt     780
tggcctctga cccttttttcc acaggggacc taccccctatt gcggtcctcc agctcatctt     840
tcacctcacc cccctcctcc tccttggctt taattatgct aatgttggag gagaatgaat     900
aaataaagtg aatctttgca cctaaaaaaa aaaaaaaa                             938

<210> SEQ ID NO 48
<211> LENGTH: 8
<212> TYPE: PRT
<213> ORGANISM: Homo sapiens

<400> SEQUENCE: 48

Gln Gln Tyr Ser Ser Pro Phe Thr
 1               5

<210> SEQ ID NO 49
<211> LENGTH: 8
<212> TYPE: PRT
<213> ORGANISM: Homo sapiens
```

```
<400> SEQUENCE: 49

Gln Gln Tyr Tyr Ser Pro Phe Thr
1               5

<210> SEQ ID NO 50
<211> LENGTH: 107
<212> TYPE: PRT
<213> ORGANISM: Homo sapiens

<400> SEQUENCE: 50

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 51
<211> LENGTH: 113
<212> TYPE: PRT
<213> ORGANISM: Homo sapiens

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys

<210> SEQ ID NO 52
<211> LENGTH: 112
<212> TYPE: PRT
<213> ORGANISM: Homo sapiens

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30
```

```
Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Ile Gln Leu Pro Arg Thr Phe Gly Gln Gly Thr Lys Val Glu Ile Lys
            100                 105                 110

<210> SEQ ID NO 53
<211> LENGTH: 112
<212> TYPE: PRT
<213> ORGANISM: Homo sapiens
<220> FEATURE:
<221> NAME/KEY: misc_feature
<222> LOCATION: (100)..(101)
<223> OTHER INFORMATION: Xaa can be any naturally occurring amino acid

<400> SEQUENCE: 53

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Xaa Xaa Thr Phe Gly Gly Gly Thr Lys Val Glu Ile Lys
            100                 105                 110

<210> SEQ ID NO 54
<211> LENGTH: 121
<212> TYPE: PRT
<213> ORGANISM: Homo sapiens
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid

<400> SEQUENCE: 54

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Xaa Xaa Asp Gly Tyr Asn Tyr Xaa Tyr Phe Asp Tyr Trp Gly
            100                 105                 110

Gln Gly Thr Leu Val Thr Val Ser Ser
            115                 120

<210> SEQ ID NO 55
<211> LENGTH: 121
<212> TYPE: PRT
<213> ORGANISM: Homo sapiens

<400> SEQUENCE: 55

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Ser Ala Glu Asp Thr Ala Val Tyr Ser Cys
                 85                  90                  95

Ala Arg Gly Gly Asp Gly Tyr Asn Tyr Tyr Tyr Phe Asp Tyr Trp Gly
            100                 105                 110

Gln Gly Thr Leu Val Thr Val Ser Ser
            115                 120

<210> SEQ ID NO 56
<211> LENGTH: 123
<212> TYPE: PRT
<213> ORGANISM: Homo sapiens
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (103)..(104)
<223> OTHER INFORMATION: Xaa can be any naturally occurring amino acid

<400> SEQUENCE: 56

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95
```

-continued

Arg Xaa Gly Tyr Ser Ser Xaa Xaa Tyr Tyr Tyr Gly Met Asp Val
            100                 105                 110

Trp Gly Gln Gly Thr Thr Val Thr Val Ser Ser
        115                 120

<210> SEQ ID NO 57
<211> LENGTH: 117
<212> TYPE: PRT
<213> ORGANISM: Homo sapiens
<220> FEATURE:
<221> NAME/KEY: misc_feature
<222> LOCATION: (98)..(101)
<223> OTHER INFORMATION: Xaa can be any naturally occurring amino acid

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Xaa Xaa Xaa Xaa Tyr Gly Met Asp Val Trp Gly Gln Gly Thr Thr
            100                 105                 110

Val Thr Val Ser Ser
        115

<210> SEQ ID NO 58
<211> LENGTH: 117
<212> TYPE: PRT
<213> ORGANISM: Homo sapiens
<220> FEATURE:
<221> NAME/KEY: misc_feature
<222> LOCATION: (98)..(99)
<223> OTHER INFORMATION: Xaa can be any naturally occurring amino acid

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Xaa Xaa Arg Asp Tyr Gly Met Asp Val Trp Gly Gln Gly Thr Thr
            100                 105                 110

Val Thr Val Ser Ser
        115

```
<210> SEQ ID NO 59
<211> LENGTH: 129
<212> TYPE: PRT
<213> ORGANISM: Homo sapiens
<220> FEATURE:
<221> NAME/KEY: misc_feature
<222> LOCATION: (100)..(102)
<223> OTHER INFORMATION: Xaa can be any naturally occurring amino acid

<400> SEQUENCE: 59

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Xaa Xaa Xaa Ile Thr Met Val Arg Gly Val Tyr Tyr Tyr
            100                 105                 110

Tyr Tyr Gly Met Asp Val Trp Gly Gln Gly Thr Thr Val Thr Val Ser
        115                 120                 125

Ser
```